United States Patent [19]

Staskawicz et al.

[11] Patent Number: 5,859,351
[45] Date of Patent: Jan. 12, 1999

[54] PRF PROTEIN AND NUCLEIC ACID SEQUENCES: COMPOSITIONS AND METHODS FOR PLANT PATHOGEN RESISTANCE

[75] Inventors: Brian S. Staskawicz, Castro Valley; Giles Edward Oldroyd, San Francisco, both of Calif.; John M. Salmeron, Hillsborough, N.C.; Caius Rommens, Chesterfield, Mo.

[73] Assignee: The Regents of the University of California, Berkeley, Calif.

[21] Appl. No.: 680,327

[22] Filed: Jul. 11, 1996

Related U.S. Application Data

[63] Continuation-in-part of Ser. No. 310,912, Sep. 22, 1994, which is a continuation-in-part of Ser. No. 227,360, Apr. 13, 1994, abandoned.
[51] Int. Cl.⁶ .............................. A01H 5/00; C07H 21/04; C12N 5/14; C12N 15/29
[52] U.S. Cl. ...................... 800/301; 435/320.1; 435/419; 435/468; 536/23.6; 536/24.3; 800/278
[58] Field of Search ........................ 536/23.6; 435/172.3, 435/320.1, 419; 800/205

[56] References Cited

PUBLICATIONS

Stam M, et al. "The silence of genes in transgenic plants". Ann. Bot. 79: 3–12, 1997.
Koziel MG, et al. "Optimizing expression of transgenes with an emphasis on post–transcriptional events." Plants Mol. Biol. 32: 393–405, 1996.
Smith CJS, et al. "Antisense RNA inhibition of polygalacturonase gene expression in transgenic tomatoes." Nature 334: 724–726, Aug. 25, 1988.
Hongyong F, et al. "Sink–and vascular–associated sucrose synthase functions are encoded by different gene classes in potato." Plant Cell 7: 1369–1385, Sep. 1995.
Waldron C, et al. "Chracterization of a genomic sequence coding for potato multicystatin, an eight–domain cysteine proteinase inhibitor." Plant Mol. Biol. 23: 801–812, 1993.
De Block M. "The cell biology of plant transformation: Current state, problems, prospects and the implications for the plant breeding." Euphytica 71: 1–14, 1993.
Martin et al., "High–resolution linkage analysis and physical characterization of the Pto bacterial resistance locus in tomato," *Molecular Plant–Microbe Interactions* 6:26–34, 1993.
Pitblado et al., "Genetic basis of resistance to *Pseudomonas syringae* pv. tomato in field tomatoes," *Canadian Journal of Plant Pathology* 5:251–255, 1983.
Saraste et al., "The P–loop —a common motif in ATP–and GTP–binding proteins," *Trends Biochem. Sci.* 15:430–434, 1990.
Song et al., "A receptor kinase–like protein encoded by the rice disease resistance gene, Xa21," *Science* 270:1804–1806, 1995.

Stotz et al., "Structure and expression of an inhibitor of fungal polygalacturonases from tomato." *Plant Molecular Biology* 25:607–617, 1994.
van Kan et al., "Cloning and characterization of cDNA of avirulence gene avr9 of the fungal pathogen *Cladosporium fulvum*, causal agent of tomato leaf mold," *Molecular Plant–Microbe Interactions* 4:52–59, 1991.
Ariat et al., "PopA1, a protein which induces a hypersensitivity–like response on specific petunia genotypes, is secreted via the Hrp pathway of *Pseudomonas Solarscaarum*," *EMBO J.* 13:543–553, 1994.
Dong et al., "Induction of Arabidopsis defense genes by virulent and avirulent *Pseudomonas syringae* strains and by a cloned avirulence gene," *The Plant Cell* 3:61–72, 1991.
Ellingboe, "Changing concepts in host–pathogen genetics," *Ann. Rev. Phytopathol* 19:125–143, 1981.
Flor, "Current status of the gene–for–gene concept." *Ann. Rev. Phytopathol* 9:275–296, 1971.
Gabriel et al., "Gene–for gene interactions of five cloned avirulence genes from *Xanthomonas campestria* pv. malvacearun with specific resistance genes in cotton," *Proc. Natl. Acad. Sci. USA* 83:6415–6419, 1986.
Gabriel, "Working models of specific recognition in plant–microbe interactions," *Annu. Rev. Phytopathl* 28:365–391, 1990.
Hahn et al., "Cultivar–specific elicitation of barley defense reactions by the phytotoxic peptide NIP1 from *Phynchosporium Secalis*," *Molecular Plant–Microbe Interactions* 6:745–754, 1993.
Innes et al., "Molecular analysis of avirulence gene avrRpt2 and indentification of a putative regulatory sequence common to all known *Pseudomonas syringae* avirulance genes," *J. Bacteriol.* 175:4859–4869, 1993.
Johel et al., "Reductase activity encoded by the HM1 disease resistance gene in maize," *Science* 258:985–987, 1992.
Joosten et al., "Host resistance to a fungal tomato pathogen lost by a single base–pair change in an avirulence gene," *Nature* 367:384–386, 1994.
Keen, "Host range determinants in plant pathogens and symbiants," *Ann. Rev. Microbiol.* 42:421–440, 1988.
Keen, "Plant disease resistance genes: interactions with pathogens and their improved utilization to control plant diseases," *Biotechnology in Plant Disease Control*, 65–88, 1993.

(List continued on next page.)

*Primary Examiner*—Douglas W. Robinson
*Assistant Examiner*—Amy J. Nelson
*Attorney, Agent, or Firm*—Klarquist Sparkman Campbell Leigh & Whinston

[57] ABSTRACT

The Prf gene of tomato has been cloned and analyzed. Prf encodes a protein with leucine-rich repeat, nucleotide binding, and leucine zipper motifs, identifying it as a member of the resistance gene class that includes RPS2, RPM1, N and L6. When expressed in transgenic plants, Prf confers Fenthion sensitivity and resistance to a wide variety of phytopathogens, including not only *Pseudomonas syringae* but also unrelated pathogens such as *Xanthomonas campestris*.

25 Claims, 34 Drawing Sheets

OTHER PUBLICATIONS

Kobayashi et al., "A gene from *Pseudomonas syringae* pv. glycinea with homology to avirulence gene D from P. s. pv. tomato but oevoid to the avirulence phenotype," *Molecular Plant–Microbe Interactions* 3:103–111, 1990.

Kobayashi et al., "Molecular characterization of avirulence gene D from *Pseudomonas syringae* pv. tomato," Molecular Plant–Microbe Interactions 3:94–102, 1990.

Kunkel et al., "RPS2, an Arabidopsis desease resistance locus specifying recognition of *Pseudomonas syringae* strains expressing the avirulence gene avrRpt2," *The Plant Cell* 5:865–875, 1993.

Lister et al., "Recombinant inbred lines for mapping RFLP and phenotypic markers in *Arabidopsis thaliana*," *The Plant Journal* 4:745–750, 1993.

Martin et al., "Map–based cloning of a protein kinase gene conferring disease resistance in tomato," *Science* 262:1432–1436, 1993.

Midland et al., "The structures of syringolides 1 and 2, Novel c–glycosidic elicitors from *Pseudomonas syringae* pv. tomato," *J. Org. Chem.* 58:2940–2945, 1993.

Staskowicz et al., "Molecular characterization of cloned avirulence genes from race 0 and race 1 of *Pseudomonas syringae* pv. *glycinea*," *J. Bacterial.* 169:5789–5794, 1987.

Van den Ackerveken et al., "Molecular analysis of the avirulence gene avr9 of the fungal tomato pathogen *Cladosporuim fulvum* fully supports the gene–for gene hypothesis," *The Plant Journal* 2:359–366, 1992.

Wanner et al., "Recognition of the avirulence gene avrB from *Pseudomonas syringae* pv. *glycinea* by *Arabidopsis thaliana*," *Molecular Plant–Microbe Interactions* 6:582–591, 1993.

Whalen et al., "Indentification of *Pseudomonas syringae* pathogens of Arabidopsis and a bacterial locus determining avirulence on both Arabidopsis and soybean," *The Plant Cell* 3:49–59, 1991.

Yu et al., "Arabidopsis mutations at the RPS2 locus results in loss of resistance to *Pseudomonas syringae* strains expressing the avirulence gene avrRpt2," *Molecular Plant–Microbe Interactions* 6:434–443, 1993.

Bent et al., *Science* 265:1856–1860, 1994.

Bunz et al., *Proc. Natl. Acad. Sci. USA* 90:11014–11018, 1993.

Burbelo et al., *Proc. Natl. Acad. Sci. USA* 90:11543–11547, 1993.

Dalrymple et al., "Cloning and characterisation of cDNA clones encoding two *Babesia bovis* proteins with homologous amino–and carboxy–terminal domains," *Molecular and Biochemical Parasitology* 59:181–190, 1993.

Dean, "Advantages of Arabidopsis for cloning plant genes," *Phil. Trans. R. Soc. Lond.* 342:189–195, 1993.

Lu et al., *Biochemical and Biophysical Research Communications* 193 (2):779–786, 1993.

Mindrinos et al., *Cell* 78:1089–1099, 1994.

Kearney et al., "Molecular basis for evasion of plant host defence in bacterial spot disease of pepper," *Nature,* 332:541–543, 1988.

Lawrence et al., "The L6 gene for flax rust resistance is related to the Arabidopsis bacterial gene RPS2 and the tobacco viral resistance gene N," *The Plant Cell,* 7:1195–1206, 1995.

Whitham et al., "The product of the tobacco mosaic virus resistance gene N: Similarity to toll and the interleukin–1 receptor," *Cell* , 78:1101–1115, 1994.

Newman et al., "Genes galore: A summary of methods for accessing results from large–scale partial sequencing of anonymous Arabidopsis cDNA clones," *Plant Physiology* 106:1241–1255, 1994.

Kobayashi et al., *Molecular Plant —Microbe Interactions* 3(2):103–111, 1990.

Kobayashi et al., *Molecular Plant —Microbe Interactions* 3(2):94–102, 1990.

Kunkel, et al., *The Plant Cell* 5:865–875, 1993.

Bisgrove et al., "A disease resistance gene in Arabidopsis with specificity for two different pathogen avirulence genes," *Plant Cell* 6:927–933, 1994.

Boyes and Nasrallah, "Physical linkage of the SLG and SRK genes at the self–incompatibility locus of *Brassica oleracea,*" *Mol. Gen. Genet.* 236:369–373, 1993.

Braun et al., "Amino–terminal leucine–rich repeats in gonadotropin receptors determine hormone selectivity," *EMBO J.* 10:1885–1890, 1991.

Carland and Staskawicz, "Genetic characterization of the Pto locus of tomato: semi–dominance and cosegregation of resistance to *Pseudomonas syringae* pathovar tomato and sensitivity to the insecticide Fenthion," *Mol. Gen. Genet.* 239:17–27, 1993.

Dangl, "Piece de rësistance: novel classes of plant disease resistance genes," *Cell* 80:363–366, 1995.

Gabriel et al., "Gene–for–gene interactions of five cloned avirulence genes from *Xanthomonas campestris* pv. malvacearum with specific resistance genes in cotton," *Proc. Natl. Acad. Sci. USA* 83:6415–6419, 1986.

Grant et al., "Structure of the Arabidopsis RPM1 gene enabling dual specificity disease resistance," *Science* 269:843–846, 1995.

Hashimoto et al., "The Toll gene of *Drosophila* , required for dorsal–ventral embryonic polarity, appears to encode a transmembrane protein," *Cell* 52, 269–279, 1988.

He et al., "*Pseudomonas syringae* pv. syringae Harpin$_{pss}$: A protein that is secreted via the Hrp pathway and elicits the hypersensitive response in plants," *Cell* 73:1255–1266, 1993.

Hëbert et al., "Partial functional mapping of the human interleukin–8 type A receptor," *J. Biol. Chem.* 268:18549–18553, 1993.

Hunter, "Protein kinases and phosphatases: the yin and yang of protein phosphorylation and signaling," *Cell* 80:225–236, 1995.

Jones et al., "Isolation of the tomato Cf–9 gene for resistance to *Cladosporium fulvum* by transposon tagging," *Science* 266:789–792, 1994.

Kataoka et al., "DNA sequence and charcaterization of the S. cerevisiae gene encoding adenylate cyclase," *Cell* 43:493–505, 1985.

Keen, "Gene–for–gene complementarity in plant–pathogen interactions," *Annu. Rev. Genet* . 24:447–463, 1990.

Kobe and Deisenhofer, "The leucine–rich repeat: a versatile binding motif," *Trends Biochem. Sci.* 19:415–421, 1994.

Long and Staskawicz, "Prokaryotic plant parasites," *Cell* 73:921–935, 1993.

Martin et al., "A member of the tomato Pto gene family confers sensitivity to Fenthion resulting in rapid cell death," *Plant Cell* 6:1543–1552, 1994.

Rodrigues and Park, "Dimerization mediated through a leucine zipper activates the oncogenic potential of the met receptor tyrosine kinase," *Mol. Cell. Biol.* 13:6711–6722, 1993.

Rommens et al., "Use of a gene expression system based on potato virus X to rapidly identify and characterize a tomato Pto homolog that controls Fenthion sensitivity," *Plant Cell* 7:249–257, 1995.

Ronald et al., "The cloned avirulence gene avrPto induces disease resistance in tomato cultivars containing the Pto resistance gene," *J. Bacteriol.* 174:1604–1611, 1992.

Ryals et al., "Signal transduction in systemic acquired resistance," *Proc. Natl. Acad. Sci. USA* 92:4202–4205, 1995.

Salmeron and Staskawicz, "Molecular characterization and hrp dependence of the avirulence gene avrPto from *Pseudomonas syringae* pv. tomato," *Mol. Gen. Genet.* 239:6–16, 1993.

Salmeron et al., "Tomato mutants altered in bacterial disease resistance provide evidence for a new locus controlling pathogen recognition." *Plant Cell* 6:511–520, 1994.

Staskawicz et al., "Molecular genetics of plant disease resistance," *Science* 268:661–667, 1995.

Stein et al., "Molecular cloning of a putative receptor protein kinase gene encoded at the self–incompatibility locus of *Brassica oleracea*," *Proc. Natl. Acad. Sci. USA* 88:8816–8820, 1991.

Sudupak et al., "Unequal exchange and meiotic instability of disease–resistance genes in the Rp1 region of maize," *Genetics* 133:119–125, 1993.

Wei et al., "Harpin, elicitor of the hypersensitive response produced by the plant pathogen *Erwinia amylovora*," *Science* 257:85–88, 1992.

Zhou et al., "The tomato gene Pti1 encodes a serine/threonine kinase that is phosphorylated by Pto and is involved in the hypersensitive response," *Cell* 83:925–935, 1995.

6.2 kb →
5.1 kb →

```
          10        20        30        40        50        60
           *         *         *         *         *         *
ATGGCCAAGGAGTGTCGCGATGCAATAGGTACTATAAACCTTGTGAAGGGCCAGCATTTA 70        80        90       100       110       120
           *         *         *         *         *         *
GACAGAAGGACCACTAATCAATTGGAGGATGCTATAAAGCACCTAACACATGTTGCTGTA 130       140       150       160       170       180
           *         *         *         *         *         *
TTTCTCACAAATCTGGAGAAGCGTCACCCTGCTAATGGAATATCTATACATCTTAGGCCT 190       200       210       220       230       240
           *         *         *         *         *         *
CTATTTTAGAAGCTCATGATGGCTTTTCTCTGATGTGTTCTCATCCTCCTCGTTCTCAG 250       260       270       280       290       300
           *         *         *         *         *         *
TTTACCGTTAAACTGGATAACATTGCTGAGAAATTCAAATCTTCAAAGGCGTCAAGATCA 310       320       330       340       350       360
           *         *         *         *         *         *
ACAAGGCAAGTGATCCCAGAGCTGCTGCAAATAATTGAACCCGAGAATATTGCTAAGCGA 370       380       390       400       410       420
           *         *         *         *         *         *
ATCAAAGCTTCAAAGCCATCAAGATCATCTAGCCCAATCACTGTGGATATGGTGGGGTTT 430       440       450       460       470       480
           *         *         *         *         *         *
ATCGAATCCTTGCTTGGTTCTGTTCATCGTGCATTGTTCTTTATCAGTGCAGGGCCTCCT 490       500       510       520       530       540
           *         *         *         *         *         *
GTGTCTATGCTTGACAAGAAGCTTCGACATCTACAAGTCTTCTTTAGACTAATTTCAAAG 550       560       570       580       590       600
           *         *         *         *         *         *
CGGGGCATTGAGCATGAGAGTATGAAGGATCTCTTCTACCATGTTGAGGATGTAGCTTAC 610       620       630       640       650       660
           *         *         *         *         *         *
ACTGCAGCACAACTATGTGTCTTGGGGTCGAGCTGCCATATGGATGACGAGTTCTCTAAA 670       680       690       700       710       720
           *         *         *         *         *         *
TTTCTGGAAAGGATAAGTCGTCCTTTTAGCCCAGGATTGAGGCAGGTTTATCTCAATGCC 730       740       750       760       770       780
           *         *         *         *         *         *
TTGATAGGGTTAAATTCATCAAGATCAAAGACTACAATGAATGCCAAATATATGCTTGAT 790       800       810       820       830       840
           *         *         *         *         *         *
TTTGTTAGTGCTCTCCAAGATGATCTGAGACTAAGATGTGATAATCGAATTCGATGGCTC
```

```
       850        860        870        880        890        900
        *          *          *          *          *          *
CAACGAGGACTTTCTTACCTTTGTCGATTCCTCAGGGACATAGAATCTTATCCTGTTTCA 910        920        930        940        950        960
        *          *          *          *          *          *
CATCGACAACTGATTTCTCTTCAATTGAATATGGAAGATCTGGCTATTGGGTCTGCAAAT 970        980        990       1000       1010       1020
        *          *          *          *          *          *
GCCATCTACTCCTATGATGAGGATATGGATAAGACTAGTGAAATAGACCATGAGCTTTTT 1030       1040       1050       1060       1070       1080
        *          *          *          *          *          *
CATTTGCAAATGAAGTTTAATTATGTTAAAGTAGAGGTTGATCTGATTCGTCTACAAAAC 1090       1100       1110       1120       1130       1140
        *          *          *          *          *          *
ATTCAAGGCACCATAATAGTTCCTATGAAAGATCTGATCGACTATGTTTGGGAAGAGCTG 1150       1160       1170       1180       1190       1200
        *          *          *          *          *          *
ATGTTCTTTAGAAGTTATTTCATGGATGCATTCGACCAGTTTAAAGAGCAGACCAGGATA 1210       1220       1230       1240       1250       1260
        *          *          *          *          *          *
ACTGTTATTTTGAACTATATTCAGTCTGCAGTTAGTCAAGCATGGTCAGTCTGTGATTCT 1270       1280       1290       1300       1310       1320
        *          *          *          *          *          *
CTTTGTCATGACTTGAATCAAAATGACTTGGCCAGGGAAATTAATTGCTTGCATTTTCAA 1330       1340       1350       1360       1370       1380
        *          *          *          *          *          *
TTGCTTCTTAAGTTCAAGTTTATCAAGGTCGCTATTAGACAGATGTGTCCCAGCATTTCT 1390       1400       1410       1420       1430       1440
        *          *          *          *          *          *
GCATCATCAACACCAGACCATCCAATGATAGATCTGCTGAACTTTCTTCCCATGAACTTT 1450       1460       1470       1480       1490       1500
        *          *          *          *          *          *
GAGGCCATTGATTCCTATTCCAGCATGCTAAAAGCCTCCTGTCCATCTTCCTCACATCGT 1510       1520       1530       1540       1550       1560
        *          *          *          *          *          *
CCTAATAGGGATGCGGAATCCCCCAATACATCATTCTTATGTGGTCCCAATACAGATGTG 1570       1580       1590       1600       1610       1620
        *          *          *          *          *          *
TACTCCTTCTATTCATCATCCTCACGTATTCCCAAGATGGATGAGATATTGAAGAGGTTT 1630       1640       1650       1660       1670       1680
        *          *          *          *          *          *
CATGAATATATTCTTGTCAATCTGCTACGGAAGGATGAAACCAATTTGACATTTACTATT
```

```
     1690        1700        1710        1720        1730        1740
       *           *           *           *           *           *
GCAGATGAGGTCAAAAGTTTTATGAAGGGTTGTTGCTCATGGTTACATATCTTATTGAA 1750        1760        1770        1780        1790        1800
       *           *           *           *           *           *
CCTCCAGTTCCTCACACTGAATGCAGGAAGCAAAATGATCTCTCAATGCGACATGAAGCT 1810        1820        1830        1840        1850        1860
       *           *           *           *           *           *
GTTGCAATTGAGGCGGAATCTGCTGTGTGTTTACATTATGAGGATAATATGAATAACAAC 1870        1880        1890        1900        1910        1920
       *           *           *           *           *           *
AGTAGGGAGATCAATCAGGTACTTCAGTTTTGACTGTGACTTTCTGGCTTATCAAGTCT 1930        1940        1950        1960        1970        1980
       *           *           *           *           *           *
GAGGGTAACTTGATGGATCTACTGAAGCACAAATCCACTTTGGGAAATCAAGTTCTAGAT 1990        2000        2010        2020        2030        2040
       *           *           *           *           *           *
CTGATTGAGAGTGCTCATGAAGAGCTTATTCTCCTTAGATCTATTCTCATGGATCTTCTT 2050        2060        2070        2080        2090        2100
       *           *           *           *           *           *
AGGAAAAAGCTTTACAGATTGGATGATCTCTTAATGCATGCTGAGGTGACTGCAAAAGG 2110        2120        2130        2140        2150        2160
       *           *           *           *           *           *
TTAGCAATATTCAGTGGTTCTTGTTATGAATATTTCATGAACGGAAGCAGCACTGAGAAA 2170        2180        2190        2200        2210        2220
       *           *           *           *           *           *
ATGAGGCCCTTGTTATCTGATTTTCTGCAAGAGATTGAGTCTGTCAAGGTAGAGTTCAGA 2230        2240        2250        2260        2270        2280
       *           *           *           *           *           *
AATGTTTGCTTGCAAGTTCTGGATATATCACCTTTTTCCCTGACAGATGGAGAAGGCCTT 2290        2300        2310        2320        2330        2340
       *           *           *           *           *           *
GTTAATTTCTTATTAAAAAACCAGGCCAAGGTGCCGAATGATGATGCTGTTTCTTCTGAT 2350        2360        2370        2380        2390        2400
       *           *           *           *           *           *
GGAAGTTTAGAGGATGCAAGCAGCACTGAGAAAATGGGACTTCCATCTGATTTTCTCCGA 2410        2420        2430        2440        2450        2460
       *           *           *           *           *           *
GAGATTGAGTCTGTTGAGATAAAGGAGGCCAGAAAATTATATGATCAAGTTTTGGATGCA 2470        2480        2490        2500        2510        2520
       *           *           *           *           *           *
ACACATTGTGAGACGAGTAAGACAGATGGAAAAAGCTTTATCAACATTATGTTAACCCAA
```

```
     2530      2540      2550      2560      2570      2580
      *         *         *         *         *         *
CAGGACAAGTTGCCGGACTATGATGCTGGTTCAGTCTCTTATCTTCTTAACCAAATATCA 2590      2600      2610      2620      2630      2640
      *         *         *         *         *         *
GTAGTTAAAGACAAATTATTGCACATTGGCTCTTTACTTGTAGATATTGTACAGTACCGG 2650      2660      2670      2680      2690      2700
      *         *         *         *         *         *
AATATGCATATAGAACTTACAGATCTCGCTGAACGTGTTCAAGATAAAAACTACATTTGT 2710      2720      2730      2740      2750      2760
      *         *         *         *         *         *
TTCTTCTCTGTCAAGGGTTATATTCCTGCTTGGTATTACACACTATATCTCTCTGATGTC 2770      2780      2790      2800      2810      2820
      *         *         *         *         *         *
AAGCAATTGCTTAAGTTTGTTGAGGCAGAGGTAAAGATTATTTGTCTGAAAGTACCAGAT 2830      2840      2850      2860      2870      2880
      *         *         *         *         *         *
TCTTCAAGTTATAGCTTCCCTAAGACAAATGGATTAGGATATCTCAATTGCTTTTTAGGC 2890      2900      2910      2920      2930      2940
      *         *         *         *         *         *
AAATTGGAGGAGCTTTTACGTTCTAAGCTCGATTTGATAATCGACTTAAAACATCAGATT 2950      2960      2970      2980      2990      3000
      *         *         *         *         *         *
GAATCAGTCAAGGAGGGCTTATTGTGCCTAAGATCATTCATTGATCATTTTTCAGAAAGC 3010      3020      3030      3040      3050      3060
      *         *         *         *         *         *
TATGATGAGCATGATGAAGCTTGTGGTCTTATAGCAAGAGTTTCTGTAATGGCATACAAG 3070      3080      3090      3100      3110      3120
      *         *         *         *         *         *
GCTGAGTATGTCATTGACTCATGCTTGGCCTATTCTCATCCACTCTGGTACAAAGTTCTT 3130      3140      3150      3160      3170      3180
      *         *         *         *         *         *
TGGATTTCTGAAGTTCTTGAGAATATTAAGCTTGTAAATAAAGTTGTTGGTGAGACATGT 3190      3200      3210      3220      3230      3240
      *         *         *         *         *         *
GAAAGAAGGAACATTGAAGTTACTGTGCATGAAGTTGCAAAGACTACCACTTATGTAGCA 3250      3260      3270      3280      3290      3300
      *         *         *         *         *         *
CCATCTTTTTCAGCTTATACTCAAAGAGCAAACGAAGAAATGGAGGGTTTTCAGGATACA 3310      3320      3330      3340      3350      3360
      *         *         *         *         *         *
ATAGATGAATTAAAGGATAAACTACTTGGAGGATCACCTGAGCTTGATGTCATCTCAATC
```

```
       3370        3380        3390        3400        3410        3420
         *           *           *           *           *           *
GTTGGCATGCCAGGATTGGGCAAGACTACACTAGCAAAGAAGATTTACAATGATCCAGAA 3430        3440        3450        3460        3470        3480
         *           *           *           *           *           *
GTCACCTCTCGCTTCGATGTCCATGCTCAATGTGTTGTGACTCAATTATATTCATGGAGA 3490        3500        3510        3520        3530        3540
         *           *           *           *           *           *
GAGTTGTTGCTCACCATTTTGAATGATGTCCTTGAGCCTTCTGATCGCAATGAAAAAGAA 3550        3560        3570        3580        3590        3600
         *           *           *           *           *           *
GATGGTGAAATAGCTGATGAGTTACGCCGATTTTGTTGACCAAGAGATTCTTGATTCTC 3610        3620        3630        3640        3650        3660
         *           *           *           *           *           *
ATTGATGATGTGTGGGACTATAAAGTGTGGGACAATCTATGTATGTGCTTCAGTGATGTT 3670        3680        3690        3700        3710        3720
         *           *           *           *           *           *
TCAAATAGGAGTAGAATTATCCTAACAACCCGCTTGAATGATGTCGCCGAATATGTCAAA 3730        3740        3750        3760        3770        3780
         *           *           *           *           *           *
TGTGAAAGTGATCCCCATCATCTTCGTTTATTCAGAGATGACGAGAGTTGGACATTATTA 3790        3800        3810        3820        3830        3840
         *           *           *           *           *           *
CAGAAAGAAGTCTTTCAAGGAGAGAGCTGTCCACCTGAACTTGAAGATGTGGGATTTGAA 3850        3860        3870        3880        3890        3900
         *           *           *           *           *           *
ATATCAAAAGTTGTAGAGGGTTGCCTCTCTCAGTTGTGTTAGTAGCTGGTGTTCTGAAA 3910        3920        3930        3940        3950        3960
         *           *           *           *           *           *
CAGAAAAAGAAGACACTAGATTCATGGAAAGTAGTAGAACAAAGTCTAAGTTCCCAGAGG 3970        3980        3990        4000        4010        4020
         *           *           *           *           *           *
ATTGGCAGCTTGGAAGAGAGCATATCTATAATTGGATTCAGTTACAAGAATTTACCACAC 4030        4040        4050        4060        4070        4080
         *           *           *           *           *           *
TATCTTAAGCCTTGTTTTCTCTATTTTGGAGGATTTTTGCAGGGAAAGGATATTCATGTC 4090        4100        4110        4120        4130        4140
         *           *           *           *           *           *
TCAAAAATGACCAAGTTGTGGGTAGCTGAAGGGTTTGTACAAGCAAACAACGAAAAAGGA 4150        4160        4170        4180        4190        4200
         *           *           *           *           *           *
CAAGAAGATACCGCACAAGGTTTCTTGGACGATCTTATTGGTAGGAATGTAGTGATGGCC
```

```
        4210        4220        4230        4240        4250        4260
          *           *           *           *           *           *
ATGGAGAAGAGACCTAATACCAAGGTGAAAACGTGCCGCATTCATGATTTGTTGCATAAA 4270        4280        4290        4300        4310        4320
          *           *           *           *           *           *
TTCTGCATGGAAAAGGCCAAACAAGAGGATTTTCTTCTCCAAATCAATAGTGGAGAAGGT 4330        4340        4350        4360        4370        4380
          *           *           *           *           *           *
GTATTTCCTGAACGATTGGAGGAATACCGATTGTTCGTTCATTCTTACCAAGATGAAATT 4390        4400        4410        4420        4430        4440
          *           *           *           *           *           *
GATCTGTGGCGCCCATCTCGCTCTAATGTCCGATCTTTACTATTCAATGCAATTGATCCA 4450        4460        4470        4480        4490        4500
          *           *           *           *           *           *
GATAACTTGTTATGGCCGCGTGATATCTCCTTCATTTTTGAGAGCTTCAAGCTTGTTAAA 4510        4520        4530        4540        4550        4560
          *           *           *           *           *           *
GTGTTGGATTTGGAATCATTCAACATTGGTGGTACTTTTCCCACTGAAATACAATATCTA 4570        4580        4590        4600        4610        4620
          *           *           *           *           *           *
ATTCAGATGAAGTACTTTGCGGCCCAAACTGATGCAAATTCAATTCCTTCATCTATAGCT 4630        4640        4650        4660        4670        4680
          *           *           *           *           *           *
AAGCTTGAAAATCTTGAGACTTTTGTCGTAAGAGGATTGGGAGGAGAGATGATATTACCT 4690        4700        4710        4720        4730        4740
          *           *           *           *           *           *
TGTTCACTTCTGAAGATGGTGAAATTGAGGCATATACATGTAAATGATCGGGTTTCTTTT 4750        4760        4770        4780        4790        4800
          *           *           *           *           *           *
GGTTTGCATGAGAACATGGATGTTTTAACTGGTAACTCACAATTACCTAATTTGGAAACC 4810        4820        4830        4840        4850        4860
          *           *           *           *           *           *
TTTTCTACTCCACGTCTCTTTTATGGTAAAGACGCAGAGAAGGTTTTGAGGAAGATGCCA 4870        4880        4890        4900        4910        4920
          *           *           *           *           *           *
AAATTGAGAAAATTGAGTTGCATATTTTCAGGGACATTTGGTTATTCAAGGAAATTGAAG 4930        4940        4950        4960        4970        4980
          *           *           *           *           *           *
GGTAGGTGTGTTCGTTTTCCCAGATTAGATTTTCTAAGTCACCTTGAGTCCCTCAAGCTG 4990        5000        5010        5020        5030        5040
          *           *           *           *           *           *
GTTTCGAACAGCTATCCAGCCAAACTTCCTCACAAGTTCAATTTCCCCTCGCAACTAAGG
```

```
       5050       5060       5070       5080       5090       5100
         *          *          *          *          *          *
GAACTGACTTTATCAAAGTTCCGTCTACCTTGGACCCAAATTTCGATCATTGCAGAACTG 5110       5120       5130       5140       5150       5160
         *          *          *          *          *          *
CCCAACTTGGTAATTCTTAAGTTATTGCTCAGAGCCTTTGAAGGGGATCACTGGGAAGTG 5170       5180       5190       5200       5210       5220
         *          *          *          *          *          *
AAAGATTCAGAGTTCCTAGAACTCAAATACTTAAAACTGGACAACCTCAAAGTTGTACAA 5230       5240       5250       5260       5270       5280
         *          *          *          *          *          *
TGGTCCATCTCTGATGATGCTTTTCCTAAGCTTGAACATTTGGTTTTAACGAAATGTAAG 5290       5300       5310       5320       5330       5340
         *          *          *          *          *          *
CATCTTGAGAAAATCCCTTCTCGTTTTGAAGATGCTGTTTGCCTAAATAGAGTTGAGGTG 5350       5360       5370       5380       5390       5400
         *          *          *          *          *          *
AACTGGTGCAACTGGAATGTTGCCAATTCAGCCCAAGATATTCAAACTATGCAACATGAA 5410       5420       5430       5440       5450       5460
         *          *          *          *          *          *
GTTATAGCAAATGATTCATTCACAGTTACTATACAGCCTCCAGATTGGTCTAAAGAACAG

5470
         *
CCCCTTGACTCTTAG
```

```
         10         20         30         40         50         60
          *          *          *          *          *          *
AATATTATAACTGTTGGAAAATGAACTCAACCATTCATCAATTATCTCAAGAAGAAGACC 70         80         90        100        110        120
          *          *          *          *          *          *
AGTATGAACTCTAAGCTTATGGGTAAGTAATTTCTCTCTGATTTTCATAAAATGAAAGAA 130        140        150        160        170        180
          *          *          *          *          *          *
GAAATTGCAAGTATTTACCTTCATTTGCTTTGTTAATTGCAGGCAGCTAGGACTTAAAAA 190        200        210        220        230        240
          *          *          *          *          *          *
AAAATCATTGAAGAAAGAGTTTTCTGTTAGATTTCAACCATCAAACACTAAACGAAAAG 250        260        270        280        290        300
          *          *          *          *          *          *
TAGTAAGTTGTTTATTTTCCTCTCATTACTCAATATTCTTAACTATAAACTAATTGC 310        320        330        340        350        360
          *          *          *          *          *          *
ATCTTATAACACAGATCTGCATCCGTTTTTGTTTTTAAATTTTGAGAAAATGGTTAAAGC 370        380        390        400        410        420
          *          *          *          *          *          *
CCCCTCCAATTACAAGCTCGTACTTCACGGGTGTCCTATCACTTTCCTGAACTGTTTAAT 430        440        450        460        470        480
          *          *          *          *          *          *
GCAAGAATTATTACACTCCTAAAACGTCATAACCACATCTATGCTAATGAGTGAGACTCA 490        500        510        520        530        540
          *          *          *          *          *          *
CTCTTTGCAGAAATTTTATTTAAAACTTTTTTTAATTCATTTTCCTTTTTGATTTATTAT 550        560        570        580        590        600
          *          *          *          *          *          *
TTAAAAAACAATTTAATATCAAAAAGTTAAAGTTTATGAATGTATTTTGTATCTTCAATT 610        620        630        640        650        660
          *          *          *          *          *          *
TGAAACATATTGTTGATAACATAGATGGTTGTTAATTATTTGAAGTTGAATATATTGAAT 670        680        690        700        710        720
          *          *          *          *          *          *
TTATGAATGTGATATTCAAATTAAAGAGACGCCCGAAATTTTATGGAAATCGATAAGCTT 730        740        750        760        770        780
          *          *          *          *          *          *
GAAATAACAATTTGACTTGCCACAAATGACCACCATTTTGAGTGGGTAATATATCAAAAA 790        800        810        820        830        840
          *          *          *          *          *          *
GTTGGAAACACTGAGAGAAGCTTATATCTAAAATTTAAGGAAATCTGGAGATGATTTAGG
```

```
         850        860        870        880        890        900
          *          *          *          *          *          *
GTGGTTTTGCATCAAATTTCAAAGCAATGGAATGAAGAAGATGAAGAACATAAACTAACT 910        920        930        940        950        960
          *          *          *          *          *          *
TTTCAGATGCGTAGGAAAAGGAAAAGTTATTAAAATTAGTCATGGATTTGTTGGGTATTA 970        980        990       1000       1010       1020
          *          *          *          *          *          *
AATATAAGATAAAAATTTATCTTAATATTCAAAGTTTATTGAAGAAAATCATTTGGGTGT 1030       1040       1050       1060       1070       1080
          *          *          *          *          *          *
TCATATATTTTTTAAAAAAAAATTGGTGCATATATCAAAGATTTTTTATATACAGTTCT 1090       1100       1110       1120       1130       1140
          *          *          *          *          *          *
TGATTTTGGAGAGTAATGGATGAAATTGCTATAAATAATTTTGGTGTATCAATTAAAGTA 1150       1160       1170       1180       1190       1200
          *          *          *          *          *          *
GTGATAGGAATGATTTCAAGATGGTGAAGAACTTTGGTGGTGCCATATTTATGTTGTGAA 1210       1220       1230       1240       1250       1260
          *          *          *          *          *          *
GTTGAAAGAAAATTAATAACTAAAAATACACATTTATTATTTGTGTTGGTTCAAACTCTA 1270       1280       1290       1300       1310       1320
          *          *          *          *          *          *
TTACCGAGAGTGAGATACACTCACTATACCACAATGTGCCACGTAAGCGTCTAGGGAGTA 1330       1340       1350       1360       1370       1380
          *          *          *          *          *          *
AATTATTTTTAGTTTTAAATAATTCAGGGAGTGATAGGACATCCGTGAAGTTGAAGTATG 1390       1400       1410       1420       1430       1440
          *          *          *          *          *          *
TAGTTGAGATTTCGGGTATAGATTGGGGGGCTTTAGACCATTGGATTTGATCTAAGTATC 1450       1460       1470       1480       1490       1500
          *          *          *          *          *          *
TATTTCAATTTATATGATGTAATTTGACTTGACACGAAATTTAAGACGAAGAAAAAAGA 1510       1520       1530       1540       1550       1560
          *          *          *          *          *          *
CTAAGTACTTCCACTGTCAAACAATATTTGTCCACTACTATTTTACACAATTAGTAAGAA 1570       1580       1590       1600       1610       1620
          *          *          *          *          *          *
ACTATACCCTTTGAATTTAATAAATACAATCTCTTGAAAAATGTAATAGTGAAATGACTA 1630       1640       1650       1660       1670       1680
          *          *          *          *          *          *
TAATTAATGATAAAAGTACATCAGGAACTAAGTGTAAAATTATCAATTCATTTTATAAAG
```

```
        1690        1700        1710        1720        1730        1740
          *           *           *           *           *           *
TAGACAAGTATTGTTGGACATCCTAAAATAGTATAGTTGACAACTATTATTGAATAGAGG 1750        1760        1770        1780        1790        1800
          *           *           *           *           *           *
GAGTATCTCTGTGTGACTATACATTTTTTAAAATTAAAATTACTAAATATAGAGAATTA 1810        1820        1830        1840        1850        1860
          *           *           *           *           *           *
AAAATGTGTTATTTCCCCCTTTTTAGAATGATTAAAAAGAAATCCGAGTCTTATTTTAGA 1870        1880        1890        1900        1910        1920
          *           *           *           *           *           *
GAGATTTAAATTGTTTCACTAAATTTTTATCAAGTTAAAAATGCTTATTTTAGAGAGTTG 1930        1940        1950        1960        1970        1980
          *           *           *           *           *           *
AGTTATTTGGCCATGTTTTTAGAAAAAAAAGTGATTGTGAGTATTGAGAGAAACTATTT 1990        2000        2010        2020        2030        2040
          *           *           *           *           *           *
TTCAATAGTTACAAAAAAATTTGGTTTAGTTTTTACTGTGTTTTTCCTCCATGGTTTCCA 2050        2060        2070        2080        2090        2100
          *           *           *           *           *           *
ACACTTGACTCTAGGCTTCTGTGCTATTTCGAAGCACTCTATAGTCTGTATCAGGGGCGG 2110        2120        2130        2140        2150        2160
          *           *           *           *           *           *
AGCCAGCTTGAATCCCTTCGGCGAAAAATATAACTATTTCTATATCGTAAAAATTATTCT 2170        2180        2190        2200        2210        2220
          *           *           *           *           *           *
TTATGTATTTATAGTAGATATTTAACCCCCCTCGGTTAGTCCGTGTGTTTAGTTCTTCAG 2230        2240        2250        2260        2270        2280
          *           *           *           *           *           *
ATTTTGAACCCCCCTAAATCCGCCACTGGTCTATACGCTTGATGTCAACTTGGTAACCTC 2290        2300        2310        2320        2330        2340
          *           *           *           *           *           *
CATTATCAAAGGTGTCTTCTTGAACTAAGATAACCAATGCTTCAAAGTGAAGATCACATA 2350        2360        2370        2380        2390        2400
          *           *           *           *           *           *
TTACACCATTGATTATATGATCATTAGGTGAAACTAAGCCACCCCGATTTCTAGATTTT 2410        2420        2430        2440        2450        2460
          *           *           *           *           *           *
GATACATTCCCTCAAGCACAAAGACACACACAATCATGCATAAGAAGAAAATAGTAGTGA 2470        2480        2490        2500        2510        2520
          *           *           *           *           *           *
AAAGTTCATGATTACATTTATGCCCGATACTTCTATAACCTACTGCAAATTATACACTTT
```

```
     2530       2540       2550       2560       2570       2580
       *          *          *          *          *          *
TATGGTATAGGCTATAGCCAAGTATCATGATAAACAACAAATACTGAAGTTCGCAACAAC 2590       2600       2610       2620       2630       2640
       *          *          *          *          *          *
CACAATAAGTTGGTTAGGAGGAAGATAATAATCACTAAGACTATAACTGTCGTCGAACTT 2650       2660       2670       2680       2690       2700
       *          *          *          *          *          *
CCAAATGTAAGCAACTTTATGATAAGCTAGTCATCACAACATTCAATAAAGATCAATATC 2710       2720       2730       2740       2750       2760
       *          *          *          *          *          *
CCAAGAGAGTTAGTATGCAATTGGATTAGAAGACGAACAGTATCTGATAAAATAAAGGAG 2770       2780       2790       2800       2810       2820
       *          *          *          *          *          *
CCTATAAATTCAAAAGACAATGCTTGTATGCTCATATTATCCCTATTACCTTTTTGCGCT 2830       2840       2850       2860       2870       2880
       *          *          *          *          *          *
AAAACACACTTCCAACTCAAGTTGTTGGATATAATTCATTTTGCAAGATTCACAAGAAAT 2890       2900       2910       2920       2930       2940
       *          *          *          *          *          *
GTCAATTTTGAGCTACCAAACTAGTCCATCATCTCGTTGGTTATCTTCCATTTATCAAAC 2950       2960       2970       2980       2990       3000
       *          *          *          *          *          *
AAAGAATCACATCCCCCGGATCAAATACAAATCAAACCCCAAACATCTCTAAGAGCTCCA 3010       3020       3030       3040       3050       3060
       *          *          *          *          *          *
ACAATCACTTCACATAGCATCTCAAATGGCAAGTTTTAAGAATAAACACAAGTCATCACA 3070       3080       3090       3100       3110       3120
       *          *          *          *          *          *
TAGTTGCTGCAACAAGTCTTAAGATCGAGGGACTTAACCTTCATAGCTTTAGAAAGCTCA 3130       3140       3150       3160       3170       3180
       *          *          *          *          *          *
AGCATAAGTGTCAACCATTCATACAATACAATCTTGAACGTAGAATATATTAAATAGTAA 3190       3200       3210       3220       3230       3240
       *          *          *          *          *          *
ATCCTAATGTATCCCAAGATAGTGCCTCCAAACTTCTTACTTCCTTGTAGTCTTTCCTGT 3250       3260       3270       3280       3290       3300
       *          *          *          *          *          *
GATGAACCTTGATAATGAGTCTGTAAGTTTTGGTTCCAAAACTGTACGTTCTTATTCATC 3310       3320       3330       3340       3350       3360
       *          *          *          *          *          *
TGTAGTGGTACAAATTTATAGTAGAGAGATATAAACTAGCAATCAGATTTCCTTAATTCA
```

```
     3370      3380      3390      3400      3410      3420
       *         *         *         *         *         *
AGGAGATTTGAGCATCAAGGGAAGCTCTAATTTCCTAAACTATTTGATAGCATATTAAAG 3430      3440      3450      3460      3470      3480
       *         *         *         *         *         *
CTAATTTTGTCAGATCTATTTATATCCTATAAAATCAGATCTGATCCTAGCCAGATATTT 3490      3500      3510      3520      3530      3540
       *         *         *         *         *         *
ACAAATCAACACTCCCCTTCAAGTTGACATGTAAGTATTTATCATGCCTAACTTGCTTAC 3550      3560      3570      3580      3590      3600
       *         *         *         *         *         *
AAGAATTTCACATTTTGGTTCAAACAAGCCTTTTATGAAAATATCCACAATTTGCTGGTC 3610      3620      3630      3640      3650      3660
       *         *         *         *         *         *
TGTTGGGACGAAAGACATACACACTTCATTTTTCAATCTTCGTTTTTATGAAGTTTCT 3670      3680      3690      3700      3710      3720
       *         *         *         *         *         *
ATCATGTTGAACTGGATTGGGAACAATACTTATGGCGGCTTTGTTGTCACATTACAACTT 3730      3740      3750      3760      3770      3780
       *         *         *         *         *         *
TATTGGTAGAGAAAATTTTCAGTCCATCTTCTTGAGCCAGTTCATTTCGTAGATCTGTAT 3790      3800      3810      3820      3830      3840
       *         *         *         *         *         *
TCAACTTTAGCAATGCTACAAGCGACATTCGGACGATACTGATTCATTACTTGCAGGATT 3850      3860      3870      3880      3890      3900
       *         *         *         *         *         *
TATTAACAATCACAGGAAACTTAAAAGGTGGAAGGGAGATGGCCAAGGAGTGTCGCGATG 3910      3920      3930      3940      3950      3960
       *         *         *         *         *         *
CAATAGGTACTATAAACCTTGTGAAGGGCCAGCATTTAGACAGAAGGACCACTAATCAAT 3970      3980      3990      4000      4010      4020
       *         *         *         *         *         *
TGGAGGATGCTATAAAGCACCTAACACATGTTGCTGTATTTCTCACAAATCTGGAGAAGC 4030      4040      4050      4060      4070      4080
       *         *         *         *         *         *
GTCACCCTGCTAATGGAATATCTATACATCTTAGGCCTCTATTTTTAGAAGCTCATGATG 4090      4100      4110      4120      4130      4140
       *         *         *         *         *         *
GCTTTTCTCTGATGTGTTCTCATCCTCCTCGTTCTCAGTTTACCGTTAAACTGGATAACA 4150      4160      4170      4180      4190      4200
       *         *         *         *         *         *
TTGCTGAGAAATTCAAATCTTCAAAGGCGTCAAGATCAACAAGGCAAGTGATCCCAGAGC
```

```
         4210       4220       4230       4240       4250       4260
           *          *          *          *          *          *
TGCTGCAAATAATTGAACCCGAGAATATTGCTAAGCGAATCAAAGCTTCAAAGCCATCAA 4270       4280       4290       4300       4310       4320
           *          *          *          *          *          *
GATCATCTAGCCCAATCACTGTGGATATGGTGGGGTTTATCGAATCCTTGCTTGGTTCTG 4330       4340       4350       4360       4370       4380
           *          *          *          *          *          *
TTCATCGTGCATTGTTCTTTATCAGTGCAGGGCCTCCTGTGTCTATGCTTGACAAGAAGC 4390       4400       4410       4420       4430       4440
           *          *          *          *          *          *
TTCGACATCTACAAGTCTTCTTTAGACTAATTTCAAAGCGGGGCATTGAGCATGAGAGTA 4450       4460       4470       4480       4490       4500
           *          *          *          *          *          *
TGAAGGATCTCTTCTACCATGTTGAGGATGTAGCTTACACTGCAGCACAACTATGTGTCT 4510       4520       4530       4540       4550       4560
           *          *          *          *          *          *
TGGGGTCGAGCTGCCATATGGATGACGAGTTCTCTAAATTTCTGGAAAGGATAAGTCGTC 4570       4580       4590       4600       4610       4620
           *          *          *          *          *          *
CTTTTAGCCCAGGATTGAGGCAGGTTTATCTCAATGCCTTGATAGGGTTAAATTCATCAA 4630       4640       4650       4660       4670       4680
           *          *          *          *          *          *
GATCAAAGACTACAATGAATGCCAAATATATGCTTGATTTGTTAGTGCTCTCCAAGATG 4690       4700       4710       4720       4730       4740
           *          *          *          *          *          *
ATCTGAGACTAAGATGTGATAATCGAATTCGATGGCTCCAACGAGGACTTTCTTACCTTT 4750       4760       4770       4780       4790       4800
           *          *          *          *          *          *
GTCGATTCCTCAGGGACATAGAATCTTATCCTGTTTCACATCGACAACTGATTTCTCTTC 4810       4820       4830       4840       4850       4860
           *          *          *          *          *          *
AATTGAATATGGAAGATCTGGCTATTGGGTCTGCAAATGCCATCTACTCCTATGATGAGG 4870       4880       4890       4900       4910       4920
           *          *          *          *          *          *
ATATGGATAAGACTAGTGAAATAGACCATGAGCTTTTTCATTTGCAAATGAAGTTTAATT 4930       4940       4950       4960       4970       4980
           *          *          *          *          *          *
ATGTTAAAGTAGAGGTTGATCTGATTCGTCTACAAAACATTCAAGGCACCATAATAGTTC 4990       5000       5010       5020       5030       5040
           *          *          *          *          *          *
CTATGAAAGATCTGATTGACTATGTTTGGGAAGAGCTGATGTTCTTTAGAAGTTATTTCA
```

```
      5050        5060        5070        5080        5090        5100
        *           *           *           *           *           *
TGGATGCATTCGACCAGTTTAAAGAGCAGACCAGGATAACTGTTATTTTGAACTATATTC 5110        5120        5130        5140        5150        5160
        *           *           *           *           *           *
AGTCTGCAGTTAGTCAAGCATGGTCAGTCTGTGATTCTCTTTGTCATGACTTGAATCAAA 5170        5180        5190        5200        5210        5220
        *           *           *           *           *           *
ATGACTTGGCCAGGGAAATTAATTGCTTGCATTTTCAATTGCTTCTTAAGTTCAAGTTTA 5230        5240        5250        5260        5270        5280
        *           *           *           *           *           *
TCAAGGTCGCTATTAGACAGATGTGTCCCAGCATTTCTGCATCATCAACACCAGACCATC 5290        5300        5310        5320        5330        5340
        *           *           *           *           *           *
CAATGATAGATCTGCTGAACTTTCTTCCCATGAACTTTGAGGCCATTGATTCCTATTCCA 5350        5360        5370        5380        5390        5400
        *           *           *           *           *           *
GCATGCTAAAAGCCTCCTGTCCATCTTCCTCACATCGTCCTAATAGGGATGCGGAATCCC 5410        5420        5430        5440        5450        5460
        *           *           *           *           *           *
CCAATACATCATTCTTATGTGGTCCCAATACAGATGTGTACTCCTTCTATTCATCATCCT 5470        5480        5490        5500        5510        5520
        *           *           *           *           *           *
CACGTATTCCCAAGATGGATGAGATATTGAAGAGGTTTCATGAATATATTCTTGTCAATC 5530        5540        5550        5560        5570        5580
        *           *           *           *           *           *
GTCTACGGAAGGATGAAACCAATTTGACATTTACTATTGCAGATGAGGTCAAAAAGTTTT 5590        5600        5610        5620        5630        5640
        *           *           *           *           *           *
ATGATGGGTTGTTGCTCATGGTTACATATCTTATTGAACCTCCAGTTCCTCACACTGAAT 5650        5660        5670        5680        5690        5700
        *           *           *           *           *           *
GCAGGAAGCAAAATGATCTCTCAATGCGACATGAAGCTGTTGCAATTGAGGCGGAATCTG 5710        5720        5730        5740        5750        5760
        *           *           *           *           *           *
CTGTGTGTTTACATTATGAGGATAATATGAATAACAACAGTAGGGAGATCAATCAGGTAC 5770        5780        5790        5800        5810        5820
        *           *           *           *           *           *
TTCAGTTTTTGACTGTGACTTTCTGGCTTATCAAGTCTGAGGGTAACTTGATGGATCTAC 5830        5840        5850        5860        5870        5880
        *           *           *           *           *           *
TGAAGCACAAATCCACTTTGGGAAATCAAGTTCTAGATCTGATTGAGAGTGCTCATGAAG
```

```
      5890        5900        5910        5920        5930        5940
        *           *           *           *           *           *
AGCTTATTCTCCTTAGATCTATTCTCATGGATCTTCTTAGGAAAAAGCTTTACAGATTGG 5950        5960        5970        5980        5990        6000
        *           *           *           *           *           *
ATGATCTCTTAATGCATGCTGAGGTGACTGCAAAAAGGTTAGCAATATTCAGTGGTTCTT 6010        6020        6030        6040        6050        6060
        *           *           *           *           *           *
GTTATGAATATTTCATGAACGGAAGCAGCACTGAGAAAATGAGGCCCTTGTTATCTGATT 6070        6080        6090        6100        6110        6120
        *           *           *           *           *           *
TTCTGCAAGAGATTGAGTCTGTCAAGGTAGAGTTCAGAAATGTTTGCTTGCAAGTTCTGG 6130        6140        6150        6160        6170        6180
        *           *           *           *           *           *
ATATATCACCTTTTTCCCTGACAGATGGAGAAGGCCTTGTTAATTTCTTATTAAAAAACC 6190        6200        6210        6220        6230        6240
        *           *           *           *           *           *
AGGCCAAGGTGCCGAATGATGATGCTGTTTCTTCTGATGGAAGTTTAGAGGATGCAAGCA 6250        6260        6270        6280        6290        6300
        *           *           *           *           *           *
GCACTGAGAAAATGGGACTTCCATCTGATTTTCTCCGAGAGATTGAGTCTGTTGAGATAA 6310        6320        6330        6340        6350        6360
        *           *           *           *           *           *
AGGAGGCCAGAAAATTATATGATCAAGTTTTGGATGCAACACATTGTGAGACGAGTAAGA 6370        6380        6390        6400        6410        6420
        *           *           *           *           *           *
CAGATGGAAAAAGCTTTATCAACATTATGTTAACCCAACAGGACAAGTTGCCGGACTATG 6430        6440        6450        6460        6470        6480
        *           *           *           *           *           *
ATGCTGGTTCAGTCTCTTATCTTCTTAACCAAATATCAGTAGTTAAAGACAAACTATTGC 6490        6500        6510        6520        6530        6540
        *           *           *           *           *           *
ACATTGGCTCTTTACTTGTAGATATTGTACAGTACCGGAATATGCATATAGAACTTACAG 6550        6560        6570        6580        6590        6600
        *           *           *           *           *           *
ATCTCGCTGAACGTGTTCAAGATAAAAACTACATTTGTTTCTTCTCTGTCAAGGGTTATA 6610        6620        6630        6640        6650        6660
        *           *           *           *           *           *
TTCCTGCTTGGTATTACACACTATATCTCTCTGATGTCAAGCAATTGCTTAAGTTTGTTG 6670        6680        6690        6700        6710        6720
        *           *           *           *           *           *
AGGCAGAGGTAAAGATTATTTGTCTGAAAGTACCAGATTCTTCAAGTTATAGCTTCCCTA
```

```
      6730      6740      6750      6760      6770      6780
        *         *         *         *         *         *
AGACAAATGGATTAGGATATCTCAATTGCTTTTAGGCAAATTGGAGGAGCTTTTACGTT 6790      6800      6810      6820      6830      6840
        *         *         *         *         *         *
CTAAGCTCGATTTGATAATCGACTTAAAACATCAGATTGAATCAGTCAAGGAGGGCTTAT 6850      6860      6870      6880      6890      6900
        *         *         *         *         *         *
TGTGCCTAAGATCATTCATTGATCATTTTCAGAAAGCTATGATGAGCATGATGAAGCTT 6910      6920      6930      6940      6950      6960
        *         *         *         *         *         *
GTGGTCTTATAGCAAGAGTTTCTGTAATGGCATACAAGGCTGAGTATGTCATTGACTCAT 6970      6980      6990      7000      7010      7020
        *         *         *         *         *         *
GCTTGGCCTATTCTCATCCACTCTGGTACAAAGTTCTTTGGATTTCTGAAGTTCTTGAGA 7030      7040      7050      7060      7070      7080
        *         *         *         *         *         *
ATATTAAGCTTGTAAATAAAGTTGTTGGTGAGACATGTGAAAGAAGGAACATTGAAGTTA 7090      7100      7110      7120      7130      7140
        *         *         *         *         *         *
CTGTGCATGAAGTTGCAAAGACTACCACTTATGTAGCACCATCTTTTTCAGCTTATACTC 7150      7160      7170      7180      7190      7200
        *         *         *         *         *         *
AAAGAGCAAACGAAGAAATGGAGGGTTTTCAGGATACAATAGATGAATTAAAGGATAAAC 7210      7220      7230      7240      7250      7260
        *         *         *         *         *         *
TACTTGGAGGATCACCTGAGCTTGATGTCATCTCAATCGTTGGCATGCCAGGATTGGGCA 7270      7280      7290      7300      7310      7320
        *         *         *         *         *         *
AGACTACACTAGCAAAGAAGATTTACAATGATCCAGAAGTCACCTCTCGCTTCGATGTCC 7330      7340      7350      7360      7370      7380
        *         *         *         *         *         *
ATGCTCAATGTGTTGTGACTCAATTATATTCATGGAGAGTTGTTGCTCACCATTTTGA 7390      7400      7410      7420      7430      7440
        *         *         *         *         *         *
ATGATGTCCTTGAGCCTTCTGATCGCAATGAAAAGAAGATGGTGAAATAGCTGATGAGT 7450      7460      7470      7480      7490      7500
        *         *         *         *         *         *
TACGCCGATTTTTGTTGACCAAGAGATTCTTGATTCTCATTGATGATGTGTGGGACTATA 7510      7520      7530      7540      7550      7560
        *         *         *         *         *         *
AAGTGTGGGACAATCTATGTATGTGCTTCAGTGATGTTTCAAATAGGAGTAGAATTATCC
```

```
      7570        7580        7590        7600        7610        7620
        *           *           *           *           *           *
TAACAACCCGCTTGAATGATGTCGCCGAATATGTCAAATGTGAAAGTGATCCCCATCATC 7630        7640        7650        7660        7670        7680
        *           *           *           *           *           *
TTCGTTTATTCAGAGATGACGAGAGTTGGACATTATTACAGAAAGAAGTCTTTCAAGGAG 7690        7700        7710        7720        7730        7740
        *           *           *           *           *           *
AGAGCTGTCCACCTGAACTTGAAGATGTGGGATTTGAAATATCAAAAGTTGTAGAGGGT 7750        7760        7770        7780        7790        7800
        *           *           *           *           *           *
TGCCTCTCTCAGTTGTGTTAGTAGCTGGTGTTCTGAAACAGAAAAAGAAGACACTAGATT 7810        7820        7830        7840        7850        7860
        *           *           *           *           *           *
CATGGAAAGTAGTAGAACAAAGTCTAAGTTCCCAGAGGATTGGCAGCTTGGAAGAGAGCA 7870        7880        7890        7900        7910        7920
        *           *           *           *           *           *
TATCTATAATTGGATTCAGTTACAAGAATTTACCACACTATCTTAAGCCTTGTTTTCTCT 7930        7940        7950        7960        7970        7980
        *           *           *           *           *           *
ATTTTGGAGGATTTTTGCAGGGAAAGGATATTCATGTCTCAAAAATGACCAAGTTGTGGG 7990        8000        8010        8020        8030        8040
        *           *           *           *           *           *
TAGCTGAAGGGTTTGTACAAGCAAACAACGAAAAAGGACAAGAAGATACCGCACAAGGTT 8050        8060        8070        8080        8090        8100
        *           *           *           *           *           *
TCTTGGACGATCTTATTGGTAGGAATGTAGTGATGGCCATGGAGAAGAGACCTAATACCA 8110        8120        8130        8140        8150        8160
        *           *           *           *           *           *
AGGTGAAAACGTGCCGCATTCATGATTTGTTGCATAAATTCTGCATGGAAAAGGCCAAAC 8170        8180        8190        8200        8210        8220
        *           *           *           *           *           *
AAGAGGATTTTCTTCTCCAAATCAATAGGTAAAAAAAACTGTATTAATTTTACATTACCA 8230        8240        8250        8260        8270        8280
        *           *           *           *           *           *
AAAAAAAGAACTGTATTAATTTTACTGTATTATGTTTATGCCAACTCTCATTTCCATGT 8290        8300        8310        8320        8330        8340
        *           *           *           *           *           *
GTTCTCTTTTATCCAATTCAGTGGAGAAGGTGTATTTCCTGAACGATTGGAGGAATACCG 8350        8360        8370        8380        8390        8400
        *           *           *           *           *           *
ATTGTTCGTTCATTCTTACCAAGATGAAATTGATCTGTGGCGCCCATCTCGCTCTAATGT
```

```
      8410       8420       8430       8440       8450       8460
        *          *          *          *          *          *
CCGATCTTTACTATTCAATGCAATTGATCCAGATAACTTGTTATGGCCGCGTGATATCTC 8470       8480       8490       8500       8510       8520
        *          *          *          *          *          *
CTTCATTTTTGAGAGCTTCAAGCTTGTTAAAGTGTTGGATTTGGAATCATTCAACATTGG 8530       8540       8550       8560       8570       8580
        *          *          *          *          *          *
TGGTACTTTCCCACTGAAATACAATATCTAATTCAGATGAAGTACTTTGCGGCCCAAAC 8590       8600       8610       8620       8630       8640
        *          *          *          *          *          *
TGATGCAAATTCAATTCCTTCATCTATAGCTAAGCTTGAAAATCTTGAGACTTTTGTCGT 8650       8660       8670       8680       8690       8700
        *          *          *          *          *          *
AAGAGGATTGGGAGGAGAGATGATATTACCTTGTTCACTTCTGAAGATGGTGAAATTGAG 8710       8720       8730       8740       8750       8760
        *          *          *          *          *          *
GCATATACATGTAAATGATCGGGTTTCTTTTGGTTTGCATGAGAACATGGATGTTTTAAC 8770       8780       8790       8800       8810       8820
        *          *          *          *          *          *
TGGTAACTCACAATTACCTAATTTGGAAACCTTTTCTACTCCACGTCTCTTTTATGGTAA 8830       8840       8850       8860       8870       8880
        *          *          *          *          *          *
AGACGCAGAGAAGGTTTTGAGGAAGATGCCAAAATTGAGAAAATTGAGTTGCATATTTTC 8890       8900       8910       8920       8930       8940
        *          *          *          *          *          *
AGGGACATTTGGTTATTCAAGGAAATTGAAGGGTAGGTGTGTTCGTTTTCCCAGATTAGA 8950       8960       8970       8980       8990       9000
        *          *          *          *          *          *
TTTTCTAAGTCACCTTGAGTCCCTCAAGCTGGTTTCGAACAGCTATCCAGCCAAACTTCC 9010       9020       9030       9040       9050       9060
        *          *          *          *          *          *
TCACAAGTTCAATTTCCCCTCGCAACTAAGGGAACTGACTTTATCAAAGTTCCGTCTACC 9070       9080       9090       9100       9110       9120
        *          *          *          *          *          *
TTGGACCCAAATTTCGATCATTGCAGAACTGCCCAACTTGGTAATTCTTAAGTTATTGCT 9130       9140       9150       9160       9170       9180
        *          *          *          *          *          *
CAGAGCCTTTGAAGGGGATCACTGGGAAGTGAAAGATTCAGAGTTCCTAGAACTCAAATA 9190       9200       9210       9220       9230       9240
        *          *          *          *          *          *
CTTAAAACTGGACAACCTCAAAGTTGTACAATGGTCCATCTCTGATGATGCTTTTCCTAA
```

```
9250       9260       9270       9280       9290       9300
  *          *          *          *          *          *
GCTTGAACATTTGGTTTTAACGAAATGTAAGCATCTTGAGAAAATCCCTTCTCGTTTTGA 9310       9320       9330       9340       9350       9360
  *          *          *          *          *          *
AGATGCTGTTTGCCTAAATAGAGTTGAGGTGAACTGGTGCAACTGGAATGTTGCCAATTC 9370       9380       9390       9400       9410       9420
  *          *          *          *          *          *
AGCCCAAGATATTCAAACTATGCAACATGAAGTTATAGCAAATGATTCATTCACAGTTAC 9430       9440       9450       9460       9470       9480
  *          *          *          *          *          *
TATACAGCCTCCAGATTGGTCTAAAGAACAGCCCCTTGACTCTTAGCAAAGGTTTGTTCT 9490       9500       9510       9520       9530       9540
  *          *          *          *          *          *
TGCTGTGTTCATCCAAGTACATTTAACATTTATTCATTTTGTTTTGCACCAGAACATGTT 9550       9560       9570       9580       9590       9600
  *          *          *          *          *          *
TGTTTTGCTAGTATTACTTGATACATTAAAAGAAATCGAACTCATATTTCTGCTACAGTC 9610       9620       9630       9640       9650       9660
  *          *          *          *          *          *
TTAACTTTTCTTGGGCTTACTCGAGGTCTAGATTAGATCAATGGTTCATGTAATTCTTAA 9670       9680       9690       9700       9710       9720
  *          *          *          *          *          *
TTCACTGTTTCATTCAACTGTCTTATCATAGTTGTGAAATGACAATATTGTTATCCCTAG 9730       9740       9750       9760       9770       9780
  *          *          *          *          *          *
CCAAATTTATTATGTTCAAATGAAAACTGATGTCACAACTACTTTTTTGTGAAATGTTTT 9790       9800       9810       9820       9830       9840
  *          *          *          *          *          *
TGAATTTTTTGCTATAAAATTGACGAATTGACAGGCTTCTATTTTGTCAGCTAAACTCT 9850       9860       9870       9880       9890       9900
  *          *          *          *          *          *
TTGTCACCAGAGGTGTATTTAGAATTACTGTGGTTTTATGAAAGATTTTTATAGAATTTT 9910       9920       9930       9940       9950       9960
  *          *          *          *          *          *
ATGCTTTTGCAGAATCTTAAGTTTCTAGTTTAAAACAACAGCACTTTTCTGTTTCAGAGG 9970       9980       9990      10000      10010      10020
  *          *          *          *          *          *
TAGCAGCAGCTAAAGTTCAAGGCATTTTGTTTATTTCTAGAACAAGGGGAGTTCTTACGT 10030      10040      10050      10060      10070      10080
  *          *          *          *          *          *
TGAATTCTTGAAAAGAAGAAGAATCAGGAGCAGGTAAAGATTATCTCTTTTTCTGTTTTT
```

```
        10090       10100       10110       10120       10130       10140
          *           *           *           *           *           *
    CTTCTTTTAGATGTTATTTCTTCATCTTGAACGTGAACACCGCTGAAAGCATTTTAATAA 10150       10160       10170       10180       10190       10200
          *           *           *           *           *           *
    AACCGGAGAAATAAATAAGATCTTTTTATATAAAGCATTATCATGTAAATATGCCTAAAT 10210       10220       10230       10240       10250       10260
          *           *           *           *           *           *
    CCATATGGTACAACTGTTTGACAAATGATAGAGAGGGGAGACTGATGCAAGTTTTATAGT 10270       10280       10290       10300       10310       10320
          *           *           *           *           *           *
    ATAAGTAAAACAGGATTGAGAAAAAAATCCTTGCACGATTTTCAATTTCTGGCCACATCA 10330       10340       10350       10360       10370       10380
          *           *           *           *           *           *
    CAATGTGTGTCAAAGTTCCCCTCTTTAAGTGGAACAAGCAATCAGAAAAGCACATTCTTA 10390       10400       10410       10420       10430       10440
          *           *           *           *           *           *
    TCGGTGACTTACCAATACCAGCTGACTGTCTCATCTTGGTTAACTTAGCCTTGCTTACTT 10450       10460       10470       10480       10490       10500
          *           *           *           *           *           *
    AGACTATTAGATTAGTTACTAATGAGCTGGTAAATTGGAACCAAATGTAGTTAGCTTGAT 10510       10520       10530       10540       10550       10560
          *           *           *           *           *           *
    GAGCTGGTAGATATGTATGTATGAAGATACACGCGTAACTTTAGTCAATGGTTAATTTTT 10570       10580       10590       10600       10610       10620
          *           *           *           *           *           *
    CATTTTGTATTTTTTCTTCACAGAGTATATATGACGCGAGAATACTTGGCCTAAAAGTT 10630       10640       10650       10660       10670       10680
          *           *           *           *           *           *
    TTTGCTTCACTAATTTAACTATTGCCGTGGATGAAACAAGCATGGCAACATTTTCAACAA 10690       10700       10710       10720       10730       10740
          *           *           *           *           *           *
    CTATCACTCAAGCAATGTAAAAAAGGAGGTTCTACGAGTGGTACATGTAAGAGTTTTGT 10750       10760       10770       10780       10790       10800
          *           *           *           *           *           *
    GCACACAAGAGGTTCTGAGACTTGAACCATCCATGTCCAAGGCAGTTCAGATGCTAGTAA 10810       10820       10830       10840       10850       10860
          *           *           *           *           *           *
    AGAAAGAAGAAGATGAACCTGCACTAATTAATCCTCCCTTTATGAATAAGAGAATGAGAA 10870       10880       10890       10900       10910       10920
          *           *           *           *           *           *
    AAAGATGGAGCTTCATGAACCAAAAGTTACCTTTTTTTTTTTAATGGCATTACTTTGAA
```

```
       10930      10940      10950      10960
         *          *          *          *
    GCACATGTTTGTTAGTTGTAAATTGTAATGGTGAAGTGTTTGTAAATA
```

```
MAKECRDAIGTINLVKGQHLDRRTTNQLEDAIKHLTHVAVFLTNLEKRHPANGISIHLRP    60
LFLEAHDGFSLMCSHPPRSQFTVKLDNIAEKFKSSKASRSTRQVIPELLQIIEPENIAKR   120
IKASKPSRSSSPITVDMVGFIESLLGSVHRALFFISAGPPVSMLDKKLRHLQVFFRLISK   180
RGIEHESMKDLFYHVEDVAYTAAQLCVLGSSCHMDDEFSKFLERISRPFSPGLRQVYLNA   240
LIGLNSSRSKTTMNAKYMLDFVSALQDDLRLRCDNRIRWLQRGLSYLCRFLRDIESYPVS   300
HRQLISLQLNMEDLAIGSANAIYSYDEDMDKTSEIDHELFHLQMKFNYVKVEVDLIRLQN   360
IQGTIIVPMKDLIDYVWEELMFFRSYFMDAFDQFKEQTRITVILNYIQSAVSQAWSVCDS   420
LCHDLNQNDLAREINCLHFQLLLKFKFIKVAIRQMCPSISASSTPDHPMIDLLNFLPMNF   480
EAIDSYSSMLKASCPSSSHRPNRDAESPNTSFLCGPNTDVYSFYSSSSRIPKMDEILKRF   540
HEYILVNLLRKDETNLTFTIADEVKKFYEGLLLMVTYLIEPPVPHTECRKQNDLSMRHEA   600
VAIEAESAVCLHYEDNMNNNSREINQVLQFLTVTFWLIKSEGNLMDLLKHKSTLGNQVLD   660
LIESAHEELILLRSILMDLLRKKLYRLDDLLMHAEVTAKRLAIFSGSCYEYFMNGSSTEK   720
MRPLLSDFLQEIESVKVEFRNVCLQVLDISPFSLTDGEGLVNFLLKNQAKVPNDDAVSSD   780
GSLEDASSTEKMGLPSDFLREIESVEIKEARKLYDQVLDATHCETSKTDGKSFINIMLTQ   840
QDKLPDYDAGSVSYLLNQISVVKDKLLHIGSLLVDIVQYRNMHIELTDLAERVQDKNYIC   900
FFSVKGYIPAWYYTLYLSDVKQLLKFVEAEVKIICLKVPDSSSYSFPKTNGLGYLNCFLG   960
KLEELLRSKLDLIIDLKHQIESVKEGLLCLRSFIDHFSESYDEHDEACGLIARVSVMAYK  1020
AEYVIDSCLAYSHPLWYKVLWISEVLENIKLVNKVVGETCERRNIEVTVHEVAKTTTYVA  1080
PSFSAYTQRANEEMEGFQDTIDELKDKLLGGSPELDVISIVGMPGLGKTTLAKKIYNDPE  1140
VTSRFDVHAQCVVTQLYSWRELLLTILNDVLEPSDRNEKEDGEIADELRRFLLTKRFLIL  1200
IDDVWDYKVWDNLCMCFSDVSNRSRIILTTRLNDVAEYVKCESDPHHLRLFRDDESWTLL  1260
QKEVFQGESCPPELEDVGFEISKSCRGLPLSVVLAGVLKQKKKTLDSWKVVEQSLSSQR   1320
IGSLEESISIIGFSYKNLPHYLKPCFLYFGGFLQGKDIHVSKMTKLWVAEGFVQANNEKG  1380
QEDTAQGFLDDLIGRNVVMAMEKRPNTKVKTCRIHDLLHKFCMEKAKQEDFLLQINSGEG  1440
VFPERLEEYRLFVHSYQDEIDLWRPSRSNVRSLLFNAIDPDNLLWPRDISFIFESFKLVK  1500
VLDLESFNIGGTFPTEIQYLIQMKYFAAQTDANSIPSSIAKLENLETFVVRGLGGEMILP  1560
CSLLKMVKLRHIHVNDRVSFGLHENMDVLTGNSQLPNLETFSTPRLFYGKDAEKVLRKMP  1620
KLRKLSCIFSGTFGYSRKLKGRCVRFPRLDFLSHLESLKLVSNSYPAKLPHKFNFPSQLR  1680
ELTLSKFRLPWTQISIIAELPNLVILKLLLRAFEGDHWEVKDSEFLELKYLKLDNLKVVQ  1740
WSISDDAFPKLEHLVLTKCKHLEKIPSRFEDAVCLNRVEVNWCNWNVANSAQDIQTMQHE  1800
VIANDSFTVTIQPPDWSKEQPLDS
```

FIG. 11

| | |
|---|---|
| 1398 | VMAMEKRPNTKVKTCRIHDLLHKF |
| 1422 | CMEKAKQEDFLLQINSGEGVFPER |
| 1446 | LEEYRLFVHSYQDEIDLWRPSRSN |
| 1470 | VRSL LFNAIDPDNLLWPRDISFI |
| 1493 | FESFKLVKVLDLESFNIGGTFPTE |
| 1517 | IQYLIQMKYFAAQTD ANSIPSS |
| 1539 | IAKLENLETFVVRGLGGEMILPCS |
| 1563 | LLKMVKLRHIHV |
| 1575 | NDRVSFGLHENMDVLTGNSQLPN |
| 1598 | LETFSTPRLFYGKDAEKVLRKMPK |
| 1622 | LRKLSCIFSGTFGYSRKLKGRCVRFPR |
| 1649 | LDFLSHLESLKLVSNSYPAKLPHK |
| 1673 | FNFPSQLRELTLSKFRLPWTQISI |
| 1697 | IAELPNLVILKLLLRAFEGDHWEVK |
| 1722 | DSEFLELKYLKLDNLKVVQWSIS |
| 1745 | DDAFPKLEHLVLTKCKHLEKIPSR |
| 1769 | FEDAVCLNRVEVNWCNWN VANS |
| 1791 | AQDIQTMQHEVIANDSFTVTIQPP |
| | |
| CONS | LXXLXXLXXLXLXXN/CXXLXXIPSX |

FIG. 12

716-786    SSTEKMRPLLSDFLQEIESVKV.EFRNVCLQVLDI..SPFSLTDGEGLVNFLLKNQAKVPNDDAVSSDGSLEDA 787-858    SSTEKM.GLPSDFLREIESVEIKEARKLYDQVLDATHCETSKTDGKSFINIMLTQQDKLPDYDAGSVSYLLNQ.

FIG. 13

PRF PROTEIN AND NUCLEIC ACID
SEQUENCES: COMPOSITIONS AND
METHODS FOR PLANT PATHOGEN
RESISTANCE

CROSS REFERENCE TO RELATED CASES

This application is a continuation-in-part of U.S. patent application Ser. No. 08/310,912, filed Sep. 22, 1994, which is a continuation-in-part of U.S. patent application Ser. No. 08/227,360, filed Apr. 13, 1994, now abandoned, both of which are incorporated herein by reference.

ACKNOWLEDGMENT OF GOVERNMENT SUPPORT

This invention was made with Government support under a National Science Foundation (NSF) Cooperative Agreement BIR-8920216 to CEPRAP, a NSF Science and Technology Center. The Government has certain rights to this invention.

BACKGROUND OF THE INVENTION

This invention relates to plant disease resistance, in particular to plant genes conferring pathogen resistance.

Whether a plant is resistant or susceptible to attack by a given pathogen is frequently under the control of a single, dominant resistance gene (Flor, *Annu. Rev. Phytopathol.* 9:275–296, 1971). Resistance gene products are thought to recognize signal molecules produced by the pathogen and respond by initiating rapid changes in host cell physiology and metabolism that directly inhibit pathogen growth.

A well-studied model for interactions of plant pathogens with their hosts is that between tomato (*Lycopersicon esculentum*) and *Pseudomonas syringae* pv. tomato (Pst; Carland and Staskawicz, *Mol. Gen. Genet.* 239:17–27, 1993; Martin et al., *Mol. Plant-Microbe Interact.* 6:26–34, 1993). Two genes required for the tomato signaling pathway that leads to resistance to Pst strains that express the avirulence gene avrPto (Ronald et al., *J. Bacteriol.* 174:1604–1611, 1992; Salmeron and Staskawicz, *Mol. Gen. Genet.* 239:6–16, 1993) have been identified through analyses of naturally-occurring resistant and susceptible tomato lines (Pitblado and MacNeill, *Canad. J. Plant Pathol.* 5:251–255, 1983) and by mutational studies (Salmeron et al., *Plant Cell* 6:511–520, 1994).

The Pto gene (Pitblado and MacNeill, *Canad. J. Plant Pathol.* 5:251–255, 1983) encodes a serine/threonine protein kinase with a potential amino-terminal myristoylation site (Martin et al., *Science* 262:1432–1436, 1993) that lacks additional motifs such as a leucine-rich repeat. Pto is a member of a tightly clustered family of five genes located on the short arm of chromosome five. It encodes a protein highly similar to the cytoplasmic domain of the Brassica self-incompatibility gene SRK and the mammalian signaling factor Raf (Martin et al., *Science* 262:1432–1436, 1993).

The identification of Pto as a protein kinase suggests that intracellular phosphorylation events are important in the response of tomato to pathogen strains expressing avrPto. The tomato Ptil protein is a substrate for Pto (Zhou et al., *Cell* 83:925–935, 1995) and Ptil itself is predicted to be a serine/threonine protein kinase (Zhou et al., *Cell* 83:925–935, 1995). Therefore, the pathway for defense against Pst may incorporate a protein kinase cascade similar to those employed in numerous other eukaryotic signaling pathways (Hunter, *Cell* 80:225–236, 1995).

The second gene required for resistance of tomato to Pst, designated Prf, was identified through a mutational approach and shown to be tightly linked to Pto (Salmeron et al., *Plant Cell* 6:511–520, 1994). Analysis of prf mutant alleles suggested that in addition to its role in disease resistance, the Prf protein also functions in the response of tomato to the organophosphate insecticide Fenthion (Salmeron et al., *Plant Cell* 6:511–520, 1994), a trait that co-segregates with Pto in genetic crosses (Carland and Staskawicz, *Mol. Gen. Genet.* 239:17–27, 1993). In sensitive tomato lines, Fenthion induces rapid necrosis that mimics the hypersensitive response observed after inoculation with Pst strains expressing avrPto (Laterrot and Philouze, *Tomato Genet. Research Coop. Newsletter* 35:6, 1985). This observation suggests that Fenthion mimics an elicitor produced under control of the avrPto gene in Pst.

Necrosis in response to Fenthion does not appear to require the Pto kinase (Martin et al., *Science* 262:1432–1436, 1993; Salmeron et al., *Plant Cell* 6:511–520, 1994), but rather is conferred by another member of the Pto gene cluster, designated Fen. Fen encodes a protein kinase 80% identical in amino acid sequence to Pto (Martin et al., *Plant Cell* 6:1543–1552, 1994; Rommens et al., *Plant Cell* 7:249–257, 1995). Thus, Prf is involved with two similar but distinct kinases, Pto and Fen, to induce hypersensitive-like necrosis in response to pathogen elicitor and Fenthion signals, respectively.

SUMMARY OF THE INVENTION

The tomato Prf genomic and cDNA sequences have been cloned and the corresponding DNA and amino acid sequences are provided herein. Expression of the Prf gene in transgenic plants confers resistance to Pst and, surprisingly, to a broad variety of unrelated pathogens. Also encompassed by the present invention are such transgenic plants. The tomato Prf gene hybridizes to homologous sequences from a variety of other plant species under moderately stringent hybridization conditions, and probes and primers based on the tomato Prf sequence can be used to isolate such Prf homologs. Based on these discoveries, the present invention provides compositions and methods related to the isolated tomato Prf gene.

For example, the present invention provides nucleic acid sequences that hybridize specifically to a native Prf sequence under at least moderately stringent conditions, preferably including at least 15 contiguous nucleotides of a native tomato Prf nucleic acid sequence (SEQ ID NO: 1). Such sequences are useful, for example, as probes and primers for isolating Prf homologs from other plant species. When expressed in transgenic plants (or plant cells or tissues), longer portions of the native Prf nucleic acid sequence, including all or a significant portion of the Prf coding region, confer pathogen resistence and/or Fenthion sensitivity.

The present invention also provides, for example, the native tomato Prf promoter sequence, which is useful, for example, for expressing a Prf gene or a heterologous gene in plant cells.

Also provided are sequences corresponding to various functional domains of the tomato Prf polypeptide (SEQ ID NO: 3), including, for example: (1) three motifs comprising the predicted ATP/GTP binding site, the "P-loop" domain occurring at residues 1120–1132, followed by the companion kinase domains 2 and 3a at 1195–1205 and 1224–1231, respectively; (2) sequences resembling leucine-rich repeat domains with approximately fourteen to eighteen imperfect copies of the leucine-rich repeat motif with a consensus sequence of LXXLXXLXXLXLXXN/CXXLXXIPSX (SEQ ID NO: 4), beginning at residue 1398; (3) a leucine zipper spanning residues 959–994; (4) a block of residues from 716–858 that includes two copies of a direct repeat, with 49% amino acid identity between the two copies; and (5) a string of seven amino acids (1058–1064) that corresponds precisely to one half of the binding site for interleukin-8 in the mammalian interleukin-8 receptor.

Armed with the disclosed tomato Prf nucleotide and amino acid sequences and taking advantage of the degeneracy of the genetic code, it is possible to design nucleic acids that are similar to the tomato Prf gene and that encode functional Prf polypeptides. Preferably, such nucleic acids include only silent or conservative changes to the native tomato Prf gene sequence. The present invention therefore also provides isolated nucleic acids that include a sequence that encodes a polypeptide that is at least about 70% homologous to a native tomato Prf polypeptide and that has Prf activity. That is, when expressed in a transgenic plant (or plant cell or tissue), the nucleic acid encodes a polypeptide that confers pathogen resistance or Fenthion sensitivity.

The present invention also encompasses cells, tissues, or transgenic plants comprising such nucleic acids.

The present invention also provides isolated Prf polypeptides comprising the at least 10 consecutive amino acids of a native tomato Prf polypeptide. Such polypeptides are useful for a number of purposes, including raising Prf-specific antibodies that can be used to purify Prf polypeptides, in immunoassays, or for expression cloning efforts.

Also provided by the present invention are related methods of producing Prf polypeptides, methods of producing pathogen-resistant transgenic plants, and methods of obtaining Prf genes from various plant species (and Prf homologs obtained thereby).

The foregoing and other aspects of the invention will become more apparent from the following detailed description and accompanying drawings.

BRIEF DESCRIPTION OF THE DRAWINGS

FIG. 1 shows corresponding genetic and physical maps of the tomato genomic region containing the Prf, Pto and Fen genes. (A) Restriction fragment length polymorphism (RFLP) markers tightly linked to Pto and within a distance to which Prf had been genetically mapped relative to Pto. (B) YACs from which a contig of approximately 400 kb was constructed. The horizontal dotted line indicates that marker VC168S was obtained by homology to the left end of YAC VC5.C2. (C) Cosmid contig of the region containing Prf constructed from VC168.G12. The 5.3 kb EcoRI fragment (SOR2) spanning the 1.1 kb deletion in tomato mutant prf-3 is indicated. Cosmid SOR2-7 complemented the prf-3 mutation (+) when transformed into prf-3 tomatoes, whereas SOR1-3 did not (–). (D) EcoRI restriction map of YAC clone RG269.D3 from the Tanskley tomato YAC library showing the locations of Pto, Fen and Prf.

FIG. 2 shows a Southern blot of DNA from resistant tomato line 76R, susceptible line 76S, and susceptible line prf-3 that was restricted with EcoRI and hybridized to the 5.3 kb SOR2 probe. M=molecular weight standards.

FIGS. 3A–3F shows the reactions of tomato plants transformed with pSOR2-7 to Fenthion and Pst strains expressing avrpto. (A) Wild-type 76R inoculated with T1(avrPto). (B) Mutant prf-3 inoculated with T1(avrPto). (C) Mutant prf-3 transformed with pSOR2-7 and inoculated with T1(avrPto). (D) Wild-type 76R treated with fenthion. (E) Mutant prf-3 treated with fenthion. (F) Mutant prf-3 transformed with pSOR2-7 and treated with fenthion.

FIG. 4 shows the kinetics of bacterial growth in prf-3 plants transformed with pSOR2-7. Data points represent the mean of three replicate experiments±standard error.

FIG. 5 shows DNA gel blot analysis of the Prf locus in the prf-3 plant transformed with pSOR2-7. Genomic DNA was digested with XbaI, separated on a 0.75% agarose gel, and transferred to a Hybond N membrane. The blot was hybridized with a $^{32}$P-labeled probe corresponding to SOR2. Arrows indicate the sizes of molecular weight markers. M=molecular weight standards.

FIG. 6 shows segregation of resistance to Pst strains expressing avrPto and T-DNA in prf-3 mutant lines transformed with pSOR2-7. Genomic DNAs were digested with BglII, separated on an 0.75% agarose gel, and transferred to a Hybond N membrane. The blots were hybridized with the 2.5 kb BglII fragment of pCDL04541. Plants were screened for resistance to T1(avrPto) by dipping in a solution of 10 mM $MgCl_2$, 0.05% Silwet L-77 (Union Carbide) containing 2×10 cfu/mL of T1(avrPto) and scored after five days. R=plants resistant to T1(avrPto); S=plants susceptible to T1(avrPto). The increased intensity of the band in the prf-3 pSOR2-7 lane is due to the amount of DNA loaded.

FIGS. 7A–7B show the results of RNA gel blot analysis of Prf. Approximately 10 $\mu$g of total RNA was separated on a 1.2% agarose gel containing 3.7% formaldehyde and transferred to a Hybond N membrane. (A) Membrane probed with the insert of pBS-Prf. (B) Membrane probed with DNA coding for the 18S rRNA.

FIG. 8 shows the physical structure of the Prf gene, including locations of lesions in prf mutations. Top shows an EcoRI restriction map of resistant tomato (76R) DNA in the vicinity of the Prf gene. The diagram below represents the Prf transcript, with exons indicated by straight horizontal lines and introns indicated by lines angled downward. The initiator (ATG) and termination (TAG) codons are indicated, as is the location of the 1.1 kb deletion in mutant prf-3. The locations and amino acid changes of three sequenced missense mutations are indicated by the downward pointing arrows.

FIG. 9 shows the nucleotide sequence of the Prf cDNA protein-coding region (SEQ ID NO: 1).

FIG. 10 shows the nucleotide sequence of a Prf genomic clone (SEQ ID NO: 2). The start of the protein coding sequence is at nucleotide 3879 and the stop is at nucleotide 9459.

FIG. 11 shows the predicted amino acid sequence of the Prf gene product (SEQ ID NO: 3). Residues underlined indicate regions of significance, as described in the text below.

FIG. 12 shows the primary structure of the Prf leucine-rich repeat, with consensus listed at bottom (SEQ ID NO: 4). Numbers on the left indicate the positions of residues in the Prf amino acid sequence.

FIG. 13 shows a region of internal repetition within the amino-terminal half of the Prf protein (SEQ ID NO: 3). Numbers on the left indicate the positions of residues in the Prf amino acid sequence.

FIG. 14 shows that homologs of the Prf gene exist in numerous plant species. A fragment encoding most of the Prf leucine-rich repeat was used to probe EcoRI digests of DNAs from the indicated species.

FIGS. 15A–15B show growth of (A) Pst strain T1 and (B) *Xanthomonas campestris* pv. *vesicatoria* p38 in pSOR2-7-transformed plant prf-3 pSOR2-7 #3 (T#3). Data points represent the mean of three replicate experiments. Error bars show standard error.

DETAILED DESCRIPTION OF THE PREFERRED EMBODIMENTS

Figure 1:
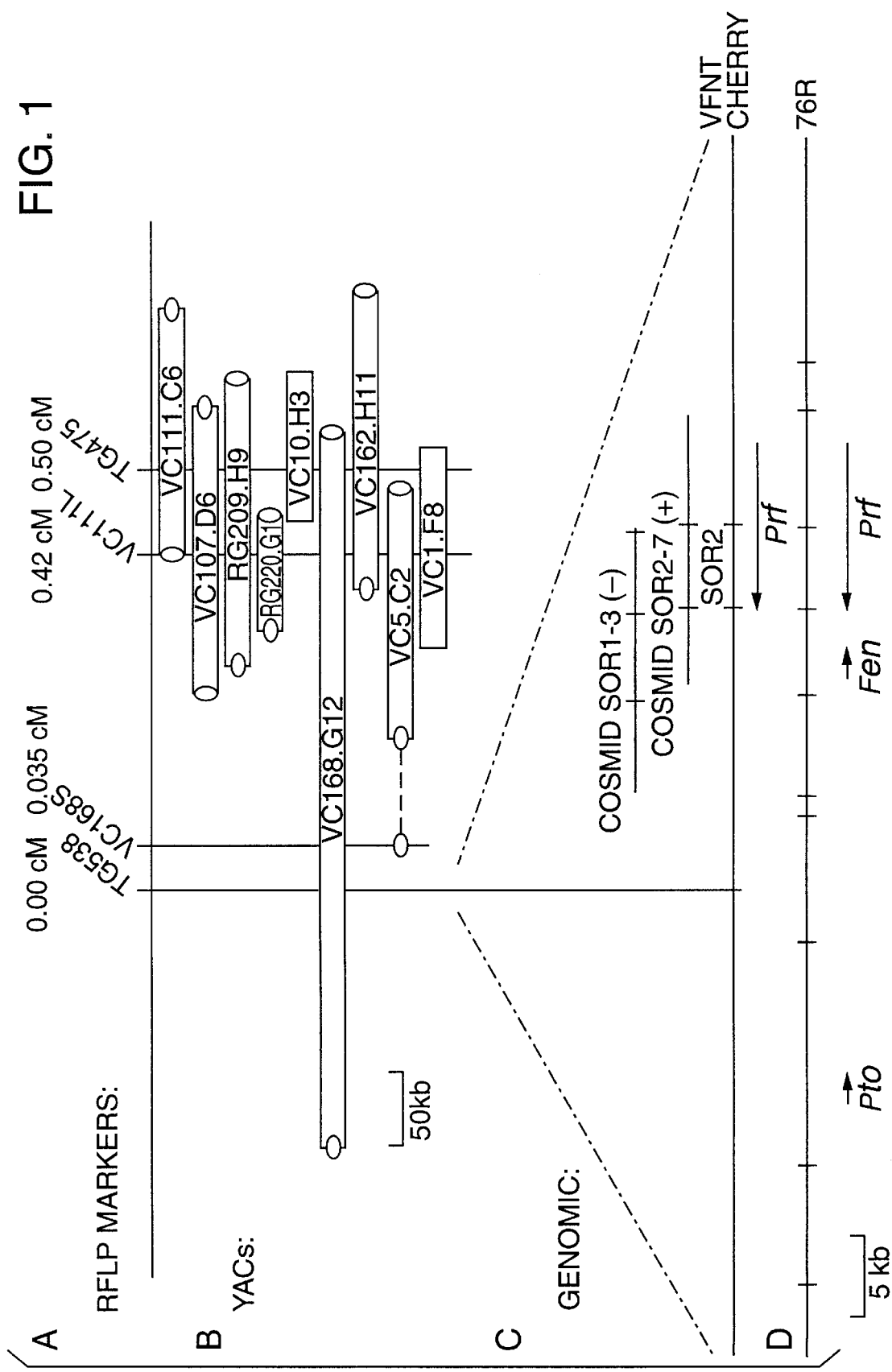

It has been discovered that the Prf gene is located within the Pto gene cluster. Prf encodes a protein with leucine-rich repeat, nucleotide binding, and leucine zipper motifs, which identifies it as a member of the resistance gene class that includes RPS2, RPM1, N and L6 (Staskawicz et al., *Science* 268:661–667, 1995; Dangl, *Cell* 80:383–386, 1995). Significantly, the cloned Prf gene (SEQ ID NO: 1) complements a tomato prf mutant for both disease resistance and Fenthion sensitivity, demonstrating that Prf, like Arabidopsis RPM1, is a common component for transduction of distinct signals. The finding that the Prf protein contains LRRs demonstrates that, at least for the tomato-Pst system, the two major classes of plant disease resistance proteins, LRR-containing proteins and protein kinases, are components of the same signaling pathway.

Surprisingly, it has been demonstrated that transgenic plants that express the Prf gene display resistance not only to Pst but also to unrelated pathogens, including, but not limited to, *Xanthomonas campestris* pv. *vesicatoria*.

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994. The nomenclature for DNA bases as set forth at 37 CFR § 1.822 is used. The standard one- and three-letter nomenclature for amino acid residues is used.

The Genetic Basis for Resistance to Pathogens

Following the invasion of a plant by a potential pathogen, the pathogen either successfully proliferates in the host, causing associated disease symptoms, or its growth is halted by the defenses of the host plant. One such defense is the hypersensitive response (HR), a rapid cellular necrosis near the site of the infection that correlates with the generation of activated oxygen species, production of antimicrobial compounds, and reinforcement of host cell walls (Dixon and Lamb, *Annu. Rev. Plant Physiol. Plant Mol. Biol.* 41:339–367, 1990). Other defenses include systemic acquired resistance, which effectively protects the plant against subsequent attack by a broad range of pathogens (Ryals et al., *Proc. Natl. Acad. Sci. USA* 92:4202–4205, 1995).

Pathogens that elicit an HR on a given host are "avirulent" on that host, the host is "resistant," and the plant-pathogen interaction is "incompatible." If a pathogen proliferates and causes disease on the host, the pathogen is "virulent," the host is "susceptible," and the plant-pathogen interaction is "compatible."

In many cases in which a strains ("races") of a particular fungal or bacterial pathogen differ regarding virulence on a various cultivars (or wild accessions) of a particular host species, avirulent strains of the pathogen, but not virulent strains, possess one or more avirulence (avr) genes corresponding to "resistance" genes in the host. This observation is the basis for the "gene-for-gene" model of plant disease resistance (Crute et al., pp. 197–309 in *Mechanisms of Resistance to Plant Disease*, Fraser, ed., 1985; Ellingboe, *Annu. Rev. Phytopathol.* 19:125–143, 1981; Flor, *Annu. Rev. Phytopathol.* 9:275–296, 1971; and Keen et al., in *Application of Biotechnology to Plant Pathogen Control*, Chet, ed., John Wiley & Sons, 1993, pp. 65–88).

Normally avirulence and resistance genes are organized in functional pairs. A given resistance gene is generally effective only against pathogen strains that express a specific cognate avirulence gene (Flor, *Annu. Rev. Phytopathol.* 9:275–296, 1971; Keen, *Annu. Rev. Genet.* 24:447–463, 1990). However, exceptions to this rule exist. For example the Arabidopsis RPM1 gene product (Grant et al., *Science* 269:843–846, 1995) is involved in the recognition of elicitors produced by *P. syringae* expressing the avirulence genes avrRpm1 or avrB (Bisgrove et al., *Plant Cell* 6:927–933, 1994), suggesting that resistance gene products may function as common points in transduction of distinct pathogen signals.

Resistance gene products are activated in response to pathogen signal molecules termed elicitors, production of which is controlled by pathogen avirulence genes.

A number of avirulence genes have been cloned (Long and Staskawicz, *Cell* 73:921–935, 1993; Dangl, in *Bacterial Pathogenesis of Plants and Animals*, Dangl, ed., Springer-Verlag, 1994, pp. 99–118; Innes et al., *J. Bacteriol.* 175:4859–4869, 1993; Dong, et al., *Plant Cell* 3:61–72, 1991; Whelan et al., *Plant Cell* 3:49–59, 1991; Staskawicz et al., *J. Bacteriol.* 169:5789–5794, 1987; Gabriel et al., *Proc. Natl. Acad. Sci. USA* 83:6415–6419, 1986; Keen and Staskawicz, *Annu. Rev. Microbiol.* 42:421–440, 1988; Kobayashi et al., *Mol. Plant-Microbe Interact.* 3:94–102 and 3:103–111, 1990). Many cloned avirulence genes have been shown to correspond to individual resistance genes in the cognate host plants and confer an avirulent phenotype when transferred to an otherwise virulent strain.

Examples of known signals to which plants respond when infected by pathogens include harpins from Erwinia (Wei et al., *Science* 257:85–88, 1992) and Pseudomonas (He et al., *Cell* 73:1255–1266, 1993); avr4 (Joosten et al., *Nature* 367:384–386, 1994) and avr9 peptides (van den Ackerveken et al., *Plant J.* 2:359–366, 1992) from Cladosporium; PopA1 from Pseudomonas (Arlat et al., *EMBO J.* 13:543–553, 1994); avrD-generated lipopolysaccharide (Midland et al., *J. Org. Chem.* 58:2940–2945, 1993); and NIP1 from Rhynchosporium (Hahn et al., *Mol. Plant-Microbe Interact.* 6:745–754, 1993).

A number of plant disease resistance genes have also been cloned (Bent et al., *Science* 265:1856–1860, 1994; Grant et al., *Science* 269:843–846, 1995; Jones et al., *Science* 266:789–792, 1994; Martin et al., *Science* 262:1432–1436, 1993; Mindrinos et al., *Cell* 78:1089–1099, 1994; Song et al., *Science* 270:1804–1806, 1995; Whitham et al., *Cell* 78:1101–1115, 1994).

Similar features have been discovered among many of these resistance genes, in spite of the diversity of pathogens against which they act. These features include a leucine-rich-repeat (LRR), a motif found in a multitude of eukaryotic proteins with roles in signal transduction (Kobe and Deisenhofer, *Trends Biochem. Sci.* 19:415–421, 1994). The LRR motif is thought to be involved in protein-protein interactions and may allow interaction with other proteins that are involved in plant disease resistance. In addition, sequences predicted to encode nucleotide binding sites and leucine zippers are shared among many resistance genes (Dangl, *Cell* 80:383–386, 1995; Staskawicz et al., *Science* 268:661–667, 1995). These motifs are present and similarly organized among resistance gene products from plants as diverse as tobacco, tomato, rice, flax, and Arabidopsis, suggesting a common mechanism underlying disease resistance signal transduction throughout the plant kingdom.

A race-specific resistance gene from *Zea mays* (corn), Hm1 (Johal and Briggs, *Science* 258:985–987, 1992), confers resistance against specific races of the fungal pathogen *Cochliobolus carbonum* by controlling degradation of a fungal toxin. This strategy is mechanistically distinct from the avirulence-gene specific resistance of the Prf-avrPto resistance mechanism.

Nucleic Acids

"Prf Gene". The term "Prf gene" or "Prf" refers to a native Prf-encoding nucleic acid sequence or a fragment thereof, e.g., the native tomato Prf cDNA (SEQ ID NO: 1) or genomic (SEQ ID NO: 2) sequences and alleles and homologs thereof. The term also encompasses variant forms of a native Prf nucleic acid sequence or fragment thereof as discussed below, preferably a nucleic acid that encodes a polypeptide having Prf biological activity. Native Prf sequences include cDNA sequences and the corresponding genomic sequences (including flanking or internal sequences operably linked thereto, including regulatory elements and/or intron sequences).

"Disease Resistance Gene". The term "disease resistance gene" refers to a plant gene such as Prf that encodes a polypeptide capable of triggering the defense response of a plant cell or tissue.

"Native". The term "native" refers to a naturally-occurring ("wild-type") nucleic acid or polypeptide.

"Homolog". A "homolog" of a tomato Prf gene is a gene sequence encoding a Prf polypeptide isolated from a plant other than tomato.

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, Probes, and Primers. A fragment of a Prf nucleic acid is a portion of a Prf nucleic acid that is less than full-length and comprises at least a minimum length capable of hybridizing specifically with a native Prf nucleic acid under stringent hybridization conditions. The length of such a fragment is preferably at least 15 nucleotides, more preferably at least 20 nucleotides, and most preferably at least 30 nucleotides of a native Prf nucleic acid sequence.

Nucleic acid probes and primers can be prepared based on a native Prf gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to the tomato Prf sequence (SEQ ID NO: 2) under high stringency hybridization conditions and hybridize specifically to a native Prf sequence of another species under at least moderately stringent conditions. Preferably, probes and primers according to the present invention have complete sequence similarity with the native tomato Pfr sequence, although probes differing from the tomato Pfr sequence and that retain the ability to hybridize to native Prf sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992); and Innis et al., *PCR Protocols: A Guide to Methods and Applications,* Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the native tomato Prf sequences disclosed herein can be used to confirm (and, if necessary, to correct) the disclosed Prf sequences by conventional methods, e.g., by re-cloning and sequencing a tomato Prf cDNA or genomic sequence.

Substantial Similarity. A first nucleic acid is "substantially similar" to a second nucleic acid if, when optimally aligned (with appropriate nucleotide insertions or deletions) with the other nucleic acid (or its complementary strand), there is at least about 75% nucleotide sequence identity, preferably at least about 80% identity, more preferably at least about 85% identity, and most preferably at least about 90% identity. Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic-acid manipulation are well-known (see, e.g., Sambrook et al., 1989, and Ausubel et al., 1992). Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic acids; Vectors, Transformation. Host cells. Natural or synthetic nucleic acids according to the present invention can be incorporated into recombinant nucleic-acid constructs, typically DNA constructs, capable of introduction into and replication in a host cell. Such a construct preferably is a vector that includes a replication system and sequences that are capable of transcription and translation of a polypeptide-encoding sequence in a given host cell.

For the practice of the present invention, conventional compositions and methods for preparing and using vectors and host cells are employed, as discussed, inter alia, in Sambrook et al., 1989, or Ausubel et al., 1992.

A cell, tissue, organ, or organism into which has been introduced a foreign nucleic acid, such as a recombinant vector, is considered "transformed", "transfected", or "transgenic." A "transgenic" or "transformed" cell or organism also includes progeny of the cell or organism and progeny produced from a breeding program employing such a "transgenic" plant as a parent in a cross and exhibiting an altered phenotype resulting from the presence of a recombinant Prf nucleic acid construct.

A number of vectors suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A function Prf gene can be expressed in plant cells under the control of the tomato Prf promoter sequence disclosed herein, for example.

Examples of constitutive plant promoters useful for expressing Prf genes include, constitutive plant promoters, including, but not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989).

A variety of plant gene promoters that are regulated in response to environmental, hormonal, chemical, and/or developmental signals, also can be used for expression of Prf in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or cholorphyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell i:961, 1989); or (5) chemicals such as methyl jasminate, salicylic acid, or Safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989).

Plant expression vectors optionally include RNA processing signals, e.g., introns, which may be positioned upstream or downstream of an Prf polypeptide-encoding sequence in the transgene. In addition, the expression vectors may also include additional regulatory sequences from the 3'-untranslated region of plant genes (Thornburg et al., Proc. Natl. Acad. Sci. USA 84:744 (1987); An et al., Plant Cell 1:115 (1989), e.g., a 3' terminator region to increase mRNA stability of the mRNA, such as the PI-II terminator region of potato or the octopine or nopaline synthase 3' terminator regions.

Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I–III, Laboratory Procedures and Their Applications Academic Press, New York, 1984.

Nucleic-Acid Hybridization; "Stringent Conditions"; "Specific". The nucleic-acid probes and primers of the present invention hybridize under stringent conditions to a target DNA sequence, e.g., to a Prf gene.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, Nucl. Acids Res. 12:203–213, 1984; and Wetmur and Davidson, J. Mol. Biol. 31:349–370, 1968.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product.

For hybridization of a tomato Prf probe to a nucleic acid of another plant species in order to identify Prf homologs, preferred hybridization and washing conditions are described in the Examples below.

The term "specific for (a target sequence)" indicates that a probe or primer hybridizes under given hybridization conditions only to the target sequence in a sample comprising the target sequence.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990.

Nucleotide-Sequence Variants of Native Prf Nucleic Acids and Amino Acid Sequence Variants of Native Prf Proteins. Using the nucleotide and the amino-acid sequence of the Prf polypeptides disclosed herein, those skilled in the art can create DNA molecules and polypeptides that have minor variations in their nucleotide or amino acid sequence.

"Variant" DNA molecules are DNA molecules containing minor changes in a native Prf sequence, i.e., changes in which one or more nucleotides of a native Prf sequence is deleted, added, and/or substituted, preferably while substantially maintaining a Prf biological activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in Prf biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native Prf sequence or a homolog thereof in which there has been a substitution of one or more base pairs but no change in the amino-acid sequence of the polypeptide encoded by the sequence. "Conservative" variants are variants of the native Prf sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed below. In addition, one or more codons encoding cysteine residues can be substituted for, resulting in a loss of a cysteine residue and affecting disulfide linkages in the Prf polypeptide.

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Nucleic Acids Attached to a Solid Support. The nucleic acids of the present invention can be free in solution or covalently or noncovalently attached by conventional means to a solid support, such as a hybridization membrane (e.g., nitrocellulose or nylon), a bead, etc.

Polypeptides

"Prf Protein". The term "Prf protein" (or polypeptide) refers to a protein encoded by a Prf nucleic acid, including alleles, homologs, and variants of a native Prf nucleic acid (SEQ ID NO: 3), for example. A Prf polypeptide can be produced by the expression of a recombinant Prf nucleic acid or be chemically synthesized. Techniques for chemical synthesis of polypeptides are described, for example, in Merrifield, *J. Amer. Chem. Soc.* 85:2149–2156, 1963.

Polypeptide Sequence Homology. Ordinarily, Prf polypeptides encompassed by the present invention are at least about 70% homologous to a native Prf polypeptide, preferably at least about 80% homologous, and more preferably at least about 95% homologous. Such homology is considered to be "substantial homology," although more important than shared amino-acid sequence homology can be the common possession of characteristic structural features and the retention of biological activity that is characteristic of Prf, preferably Prf catalytic activity.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated." "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. Various methods of protein purification are described, e.g., in *Guide to Protein Purification*, ed. Deutscher, *Meth. Enzymol.* 185, Academic Press, San Diego, 1990; and Scopes, *Protein Purification: Principles and Practice*, Springer Verlag, New York, 1982.

Variant and Modified Forms of Prf Polypeptides. Encompassed by the Prf polypeptides of the present invention are variant polypeptides in which there have been substitutions, deletions, insertions or other modifications of a native Prf polypeptide. The variants substantially retain structural characteristics and biological activities of a corresponding native Prf polypeptide and are preferably silent or conservative substitutions of one or a small number of contiguous amino acid residues.

A native Prf polypeptide sequence can be modified by conventional methods, e.g., by acetylation, carboxylation, phosphorylation, glycosylation, ubiquitination, and labeling, whether accomplished by in vivo or in vitro enzymatic treatment of a Prf polypeptide or by the synthesis of a Prf polypeptide using modified amino acids.

Labeling. There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel et al., 1992.

Polypeptide Fragments. The present invention also encompasses fragments of a Prf polypeptide that lacks at least one residue of a native full-length Prf polypeptide. Preferably, such a fragment retains the ability to confer resistance to Pst or sensitivity to Fenthion when expressed as a transgene in a plant or possession of a characteristic functional domain, or an immunological determinant characteristic of a native Prf polypeptide. Immunologically active fragments typically have a minimum size of 7 to 17 or more amino acids.

The terms "biological activity", "biologically active", "activity" and "active" refer primarily to the characteristic biological activity or activities of a native Prf polypeptide, including, but not limited to, the ability to confer Pst resistance or Fenthion sensitivity to a transgenic plant.

Fusion Polypeptides. The present invention also provides fusion polypeptides including, for example, heterologous fusion polypeptides in which a Prf polypeptide sequence is joined to a fusion partner. Such fusion polypeptides can exhibit biological properties (such as substrate or ligand binding, enzymatic activity, antigenic determinants, etc.) derived from each of the fused sequences. Any conventional fusion partner can be used, including, for example, β-glucuronidase, beta galactosidase, etc. Fusion polypeptides are preferably made by the expression of recombinant nucleic acids produced by standard techniques.

Polypeptide Sequence Determination. The sequence of a polypeptide of the present invention can be determined by any of the various methods known in the art.

Polypeptide Coupling to a Solid Phase Support. The polypeptides of the present invention can be free in solution or coupled to a solid-phase support, e.g., nitrocellulose, nylon, column packing materials (e.g., Sepharose beads), magnetic beads, or glass wool, by conventional methods.

Antibodies

The present invention also encompasses polyclonal and/or monoclonal antibodies capable of specifically binding to a Prf polypeptide and/or fragments thereof. Such antibodies are raised against a Prf polypeptide or fragment thereof and are capable of distinguishing a Prf polypeptide from other polypeptides, i.e., are Prf-specific.

For the preparation and use of antibodies according to the present invention, including various immunoassay techniques and applications, see, e.g., Goding, *Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, N.Y., 1988. Prf-specific antibodies are useful, for example in: purifying a Prf polypeptide from a biological sample, such as a host cell expressing recombinant a Prf polypeptide; in cloning a Prf allele or homolog from an expression library; as antibody probes for protein blots and immunoassays; etc.

Prf polypeptides and antibodies can be labeled by any of a variety of conventional methods. Suitable labels include, but are not limited to, radionuclides, enzymes, substrates, cofactors, inhibitors, fluorescent agents, chemiluminescent agents, magnetic particles, etc.

Obtaining Alleles and Homologs of Tomato Prf.

As discussed in the Examples below, fragment(s) homologous to Prf exist in many plant species. Using moderately high stringency hybridization conditions, most species tested showed one or two homologous fragments, while a large homologous gene family of approximately nine members was detected in tobacco. Based upon the availability of the tomato Prf cDNA and genomic sequences as disclosed herein (SEQ ID NO: 1 and 2 respectively), alleles of the cloned tomato Prf gene and homologs from other plant species can be obtained by conventional methods, e.g., by screening a cDNA or genomic library with a probe that specifically hybridizes to a native Prf sequence under at least moderately stringent conditions (e.g., the tomato Prf cDNA, SEQ ID NO: 1, or a fragment thereof), by PCR or another amplification method using a primer or primers that specifically hybridize to a native Prf sequence under at least moderately stringent conditions, or by identification of Prf alleles or homologs in an expression library using Prf-specific antibodies.

Probes and primers based on the tomato Prf sequence disclosed herein (SEQ ID NO: 1 or 2) can also be used to obtain other plant disease resistance genes having substantial similarity to tomato Prf by conventional methods.

Plant Transformation and Regeneration

Various nucleic acid constructs that include a Prf nucleic acid are useful for producing pathogen-resistant plants.

Prf nucleic acids can be expressed in plants or plant cells under the control of a suitable operably linked promoter that is capable of expression in a cell of a particular plant. Any well-known method can be employed for plant cell transformation, culture, and regeneration in the practice of the present invention with regard to a particular plant species. Conventional methods for introduction of foreign DNA into plant cells include, but are not limited to: (1) Agrobacterium-mediated transformation (Lichtenstein and Fuller In: *Genetic Engineering,* Vol 6, Rigby, ed., London, Academic Press, 1987; and Lichtenstein and Draper, in: *DNA Cloning,* Vol II, Glover, ed., Oxford, IRI Press, 1985); (2) particle delivery (see, e.g., Gordon-Kamm et al., *Plant Cell* 2:603, 1990; or BioRad Technical Bulletin 1687), (3) microinjection (see, e.g., Green et al., *Plant Tissue and Cell Culture,* Academic Press, New York, 1987), (4) polyethylene glycol (PEG) procedures (see, e.g., Draper et al., *Plant Cell Physiol.* 23:451, 1982); Zhang and Wu, *Theor. Appl. Genet.* 76:835, 1988), (5) liposome-mediated DNA uptake (see, e.g., Freeman et al., *Plant Cell Physiol.* 25:1353, 1984), (6) electroporation (see, e.g., Fromm et al., *Nature* 319:791 (1986)); and (7) vortexing method (see, e.g., Kindle, *Proc. Natl. Acad. Sci. USA* 87:1228 (1990)).

The term "plant" encompasses any higher plant and progeny thereof, including monocots (e.g., lily, corn, rice, wheat, barley, etc.), dicots (e.g., tomato, potato, soybean, cotton, tobacco, etc.), and includes parts of plants, including reproductive units of a plant (e.g., seeds), fruit, flowers, etc.

A "reproductive unit" of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

A Prf transgene is useful for conferring disease resistance on plants that would otherwise be susceptible to plant pathogens carrying the avirulence gene, avrPto, e.g., Pst. Several cloned plant host resistance genes confer disease resistance to transgenic plants. For example, the N gene of tobacco confers resistance to a viral pathogen (TMV) (Whitham et al., *Cell* 78:1101–1115, 1994); the RPM1 gene of Arabidopsis confers resistance to *Pseudomonas syringae* strains carrying the avrRpm1 avirulence gene (Grant et al., *Science* 269:843–846, 1995; and the L6 gene of flax confers resistance to flax rust, a fungal pathogen (Lawrence et al., *Plant Cell* 7:1195–1206, 1995).

As demonstrated in the Examples below, expression of Prf in transgenic plants can confer resistance not only to Pst but also to *Xanthomonas campestris* pv. *vesicatoria* and to a wide variety of other phytopathogens, including, but not limited to, bacteria, viruses (e.g., tobacco mosaic virus, potato virus X, etc.), fungi (e.g., *Phytophthora infestans*, Fusarium spp., etc.), and nematodes (e.g., root knot nematode, etc.). To confer such broad-spectrum pathogen resistance, it is preferable to express a Prf transgene at high levels, e.g., through expression of multiple copies of the Prf transgene and/or the use of strong promoters to drive Prf expression. Expression of a Prf transgene in plant cells at a sufficiently high level may initiate the plant defense response constitutively in the absence of signals from the pathogen. The level of Prf mRNA and polypeptide expression can be determined by conventional methods. Prf transgene expression can be driven by its own promoter or by a heterologous promoter. An inducible, or tissue-specific promoter, for example, can be used to limit the temporal and tissue expression of a defense response.

The Prf gene can be co-expressed in a plant cell with the avrPto gene to mimic the production of gene products associated with the initiation of the plant defense response and provide resistance to pathogens in the absence of specific resistance gene-avirulence gene corresponding pairs in the host plant and pathogen.

The invention will be better understood by reference to the following Examples, which are intended to merely illustrate the best mode now known for practicing the invention. The scope of the invention is not to be considered limited thereto.

EXAMPLES

Experimental Procedures

Mapping the Prf Gene. To map the Prf gene relative to Pto, $F_2$ progeny from crosses of prf mutant plants (prf Pto/prf Pto) to tomato line 76S (Prf pto/Prf pto; Carland and Staskawicz, *Mol. Gen. Genet.* 239:17–27, 1993) were analyzed for the presence of recombinant chromosomes carrying wild-type alleles of both genes. Out of 413 progeny, tested by scoring for resistance to transconjugants of Pst strain T1 containing the avrPto plasmid pPtE6 (Ronald et al., *J. Bacteriol.* 174:1604–1611, 1992), none were recombinant, indicating a maximal genetic distance between Prf and Pto of 0.12 cM.

Construction of YAC and Cosmid Contigs Spanning the Prf/Pto Region. All plasmid and cosmid manipulations, preparation of bacterial and yeast media, and hybridization techniques were performed using standard protocols (Ausubel et al., 1992). Tomato RFLP clones TG538 and TG475, which had been previously mapped to the Prf/Pto region (Martin et al., *Mol. Plant-Microbe Interact.* 6:26–34, 1993), were obtained from Dr. Steven Tanksley (Cornell University). In addition, YAC clones corresponding to TG475, VC111.C6 and VC107.D6 (Martin et al., *Mol. Plant-Microbe Interact.* 6:26–34, 1993), were obtained independently from Drs. Steven Tanksley and Valerie Williamson (University of California, Davis). Ends of these two YACs were isolated and used to identify polymorphic bands between near-isogenic lines 76R (Prf Pto/Prf Pto) and 76S (Prf pto/Prf pto), which differ in the presence or absence of the Pto gene. The markers could then be mapped relative to Pto by probing a mapping population of 1414 $F_2$ individuals from a cross of 76R to 76S. This revealed that the left end of YAC VC111.C6 was closer to Pto than TG475. TG538 and this YAC end were sequenced and oligonucleotides synthesized to create primer pairs corresponding to each marker. Primers for TG538 were:

5'-CCAAGTGCAGAGAGTACTGGA-3'  (SEQ ID NO: 5) and
5'-TGAATGAACATGATCAAAGTATGC-3'  (SEQ ID NO: 6)

primers for the left end of YAC VC111.C6 were:

5'-ACTCCAGAACCAATGATTGCATA-3'  (SEQ ID NO: 7) and
5'-GGAATTTAAATCTAGAATATCTC-3'  (SEQ ID NO: 8)

Primers pairs were used to screen a copy of the Tanskley tomato YAC library obtained from the NSF Center for Engineering Plants for Resistance Against Pathogens. YAC clones RG209.H9, RG220.G1, VC168.G12, VC162.H11, VC5.2, and VC1.F8 were found to contain the left end of VC111.C6, and clones VC168.G12, RG269.D3, RG669.C9 and RG675.C2 were found to contain TG538. YAC ends were subcloned and mapped relative to other YACs and to the Pto gene to construct a contig across the Prf/Pto region (FIG. 1B). Additional markers tightly linked to Pto were derived by subcloning fragments from the contig and mapped by probing the 76R×76S $F_2$ population. In this way, RFLP marker VC168S (a copy of the repetitive right end of YAC VC5.2) was mapped to 0.035 cM from Pto and marker TG538 was mapped to 0.00 cM of Pto.

To form cosmid contigs across the Pto/Prf locus, libraries of 10–20 kb insert size were constructed in pCDL04541 (Jones et al., *Transgenic Research* 1:285–297, 1992) from yeast containing either of VC168.G12 or RG269.D3. VC168S and TG538 were used as probes to isolate corresponding clones from the cosmid libraries. Cosmid ends were cloned and used in recurrent probing of libraries to eventually form contigs of 167 kb (VC168.G12) spanning VC168S and TG538 and 80 kb (RG269.D3). Cosmids pSOR1-3 and pSOR2-7, from VC168.G12, bear the 5 kb EcoRI fragment SOR2 that contains most of the Prf coding sequence. SOR2 was identified as Prf by a mutational alteration within the fragment, as discussed below.

Cloning the Prf Gene. To construct the tomato cDNA library, line 76R was vacuum infiltrated with a solution of Pst strain T1 (avrPto) at a concentration of $5 \times 10^7$ cfu/mL. Leaf tissue was harvested after 6 hr incubation at room temperature and the library was constructed using a ZAP-cDNA Synthesis kit (Stratagene). The cDNA library of VFNT Cherry was provided by Dr. Wilhelm Gruissem. Approximately $1.6 \times 10^6$ clones were screened from the 76R library, with five hybridizing plaques obtained, and $2 \times 10^5$ clones from the VFNT Cherry library with three hybridizing plaques obtained. The longest cDNA (1.2 kb) was designated Cdr1. As an initial step to obtain a full-length cDNA for Prf, primers throughout the SOR2 region were used in combination with a primer corresponding to the trailer mRNA of Cdr1 in PCR reactions using 76R mRNA as template and a Stratascript kit (Stratagene). The longest clone was obtained using 5'-CCTTCTATTCATCATCC-3' (SEQ ID NO: 9) and 5'-CTGCTCCTGATTCTTCT-3' (SEQ ID NO: 10) as amplification primers. This 4.0 kb band was cloned into the XhoI and XbaI sites of pBluescript-KS(+) (Stratagene) to form pBS-Prf.

5' RACE analysis (Frohman et al., *Proc. Nat. Acad. Sci. USA* 85:8998–9002, 1988) was performed to identify the 5' end of the Prf transcript. The Life Technologies 5'RACE kit (Cat. No. 18374–025) was used as specified by the manufacturer, except that first strand cDNAs were tailed with DATP instead of dCTP. The primer "T Prime" (5'-TTGCATTGACGTCGACTATCCAGGTTTTTTTTTTTT-3'(SEQ ID NO: 11)) was substituted for the primer supplied with the kit in all the subsequent PCR amplifications. In each RACE experiment, first strand cDNA was synthesized from 0.25mg of poly-A$^+$ RNA isolated from tomato cultivar 76R. Two separate RACE reactions were performed to confirm the 5' end of the Prf transcript. The first experiment used a Prf-specific primer PrfPX1 (5'-TAAGATATGTAACCATGAGCAACAACCCTTC-3'(SEQ ID NO: 12)) to prime cDNA synthesis. The sequence of PrfPX1 was chosen from analysis of the pBS-Prf insert. After dATP tailing, primers T Prime and PrfPX2 (5'-GACCTCATCTGCAATAGTA-3'(SEQ ID NO: 13)) were used for PCR amplification. The reaction yielded a 2.0 kb product which was captured in the vector pCRII (Invitrogen). Two clones from this PCR amplification, SS071.7 and SS071.11, were sequenced and indicated transcripts with 5' ends 5648 nucleotides and 5640 nucleotides, respectively, upstream from the codon terminating the Prf ORF. The second 5' RACE experiment was performed using Prf-specific primers closer to the 5' ends mapped by the first RACE reaction. Primer PrfPX1B (5'-AGGCCCTGCACTGATAAAGAACAA-3'(SEQ ID NO: 14)) was used to prime cDNA synthesis, and primer PrfPX2B (5'-AGCAGCTCTGGGATCACTTGCCTT-3' (SEQ ID NO: 15)) was used with T Prime for the PCR amplification. This reaction resulted in a 0.53 kb amplification product which was also cloned in PCRII. Five clones were sequenced. The longest two clones (SS074.3 and SS074.12) indicated transcripts with 5' ends 5638 and 5677 bp, respectively, upstream of the termination codon.

DNA Sequencing. The insert of pBS-Prf along with the 5' RACE products were sequenced either with Sequenase (United States Biochemical Corporation) by the dideoxy-nucleotide method, or using an Applied Biosystems 373 DNA Sequencer or a Licor DNA sequencer. Sequence data was compiled and analyzed using the Sequencher software (GeneCodes, Inc.). To obtain the sequence of the Prf genomic clones, the 5 kb SOR2 fragment was excised from cosmids R207 (from resistant tomato) and pSOR2-7 (susceptible tomato), cut with HindIII, subcloned into pBluescript KS-(+), and sequenced as described above. Subclones of mutant prf alleles were amplified from genomic DNAs using Prf-specific primers, ligated into pCRII (Invitrogen), and sequenced.

Complementation. Cosmid pSOR2-7 was introduced into tomato mutant line prf-3 by Agrobacterium-mediated transformation of excised cotyledons essentially as described by McCormick et al., 1986. Transgenic plants were identified by resistance to kanamycin (50 µg/ml) and confirmed by DNA gel blot analysis. Transformants were analyzed by inoculation with Pst strain T1(avrPto) and exposure to Fenthion as described previously (Carland and Staskawicz, *Mol. Gen. Genet.* 239:17–27, 1993).

Gel Blot Analysis. DNA and RNA gel blot analysis was performed using standard procedures (Ausubel et al., 1992). In the RNA gel blot analysis, hybridization was performed in the presence of 10% dextran sulfate. For testing for homologs to Prf in other plant species, hybridization was performed using a radiolabelled 1.4 kb HindIII fragment from pSOR2-7, corresponding to nucleotides 3150–4494 of Prf (SEQ ID NO: 1), under conditions of 65° C., 6XSSC. Washing was performed for 1 hour in 0.5XSSC, 0.5% SDS at 65° C. The molecular weight standards used were the 1-kb Ladder (Bethesda Research Laboratories) and the 0.24–9.5-kb RNA Ladder (Gibco BRL).

Results

Construction of YAC and Cosmid Contigs Across the Prf/Pto Locus. There is tight linkage between the Prf and Pto genes, as shown through analysis of F$_2$ progeny from crosses of prf mutant plants to pto mutant lines (Salmeron et al., *Plant Cell* 6:511–520, 1994). Analysis of additional prf×pto F$_2$ individuals allowed us to assign Prf to a distance of no more than 0.12 cM from Pto. Given the estimated ratio of 220 kb/cM for the region around Pto, as derived from analysis of a YAC clone spanning the Pto gene (Martin et al., *Science* 262:1432–1436, 1993), we employed molecular markers in the vicinity of the Pto locus (Martin et al., *Mol. Plant-Microbe Interact.* 6:26–34, 1993) to expedite cloning of the Prf gene. FIG. 1A shows RFLP markers that are tightly linked to the Pto gene and that lie within a distance to which Prf had been genetically mapped relative to Pto.

Initially, we constructed a contig of approximately 400 kb that included eleven YACs in the vicinity of Pto by probing available YAC libraries with Pto-linked markers (FIG. 1B; Martin et al., *Mol. Plant-Microbe Interact.* 6:26–34, 1993). Positioning the ends of these YACs on the genetic map led us to focus on two markers, VC168S and TG538, which mapped to 0.04 and 0.00 cM from the Pto locus (FIG. 1A). These markers were used as probes to isolate corresponding cosmids from libraries of 76R (Pto Prf/Pto Prf) and VFNT Cherry (pto Prf/pto Prf) DNAs. Cosmid walking from these starting points resulted in the construction of contigs which span 80 kb (76R DNA) and 167 kb (VFNT Cherry DNA).

Localization of the Prf Gene Within Cosmid Contigs. Mutations in the prf gene had been isolated with fast neutrons and diepoxybutane, agents that were known to cause deletion mutations in other eukaryotic systems (Reardon et al., *Genetics* 115:323–331, 1987; Sun et al., *Plant Cell* 4:119–128, 1992). Given the tight linkage between the Prf and Pto genes, and the availability of cosmids from the Pto region, we decided to test for the presence of deletions in prf mutant plants that could be used to localize the Prf gene. Single-copy probes were identified throughout the cosmid contigs and hybridized to gel blots of prf mutant DNAs. A 5.3 kb EcoRI fragment, designated SOR2 (FIG. 1C), detected a 1.1 kb alteration in mutant line prf-3 (FIG. 2), a plant isolated by fast neutron bombardment (Salmeron et al., *Plant Cell* 6:511–520, 1994). Fragments adjacent to SOR2 detected no alteration in prf-3, suggesting that prf-3 comprised a simple deletion within the SOR2 fragment. No additional alterations were observed with other probes or in DNAs from other prf mutant lines.

Figure 3A:
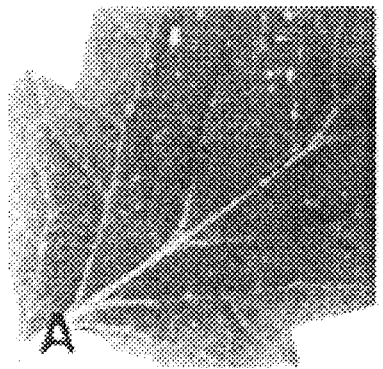
Figure 3B:
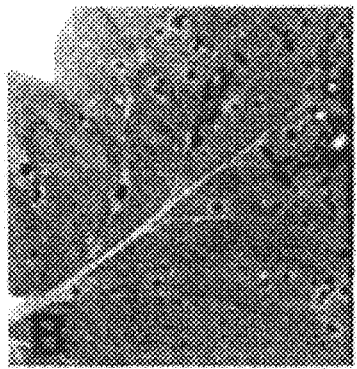
Figure 3C:
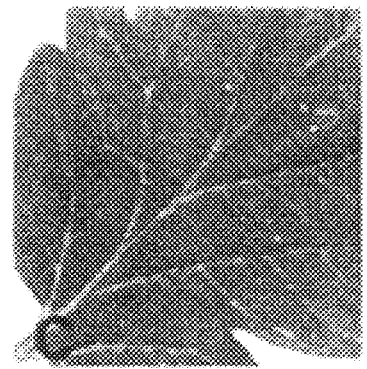

Complementation of the prf-3 Mutation by Cosmids Containing 80R2. To directly test whether the region surrounding SOR2 encodes Prf activity, cosmids containing SOR2 were introduced into the tomato mutant prf-3 by Agrobacterium-mediated transformation. Transgenic plants, selected for kanamycin resistance, were inoculated with Pst strain T1 (normally virulent on Pto Prf tomatoes) and a transconjugant, T1 (avrPto), that expresses the avrPto avirulence gene and is recognized by tomatoes expressing the Prf and Pto genes (Ronald et al., *J. Bacteriol.* 174:1604–1611, 1992). Plants were dipped in a solution of 10 mM MgCl$_2$, 0.05% Silwet L77 (Union Carbide) containing 2×10$^8$ cfu/mL of Pst strain T1(avrPto) (Ronald et al., *J. Bacteriol.* 174:1604–1611, 1992) and photographed after five days (FIGS. 3A–C).

Figure 4:
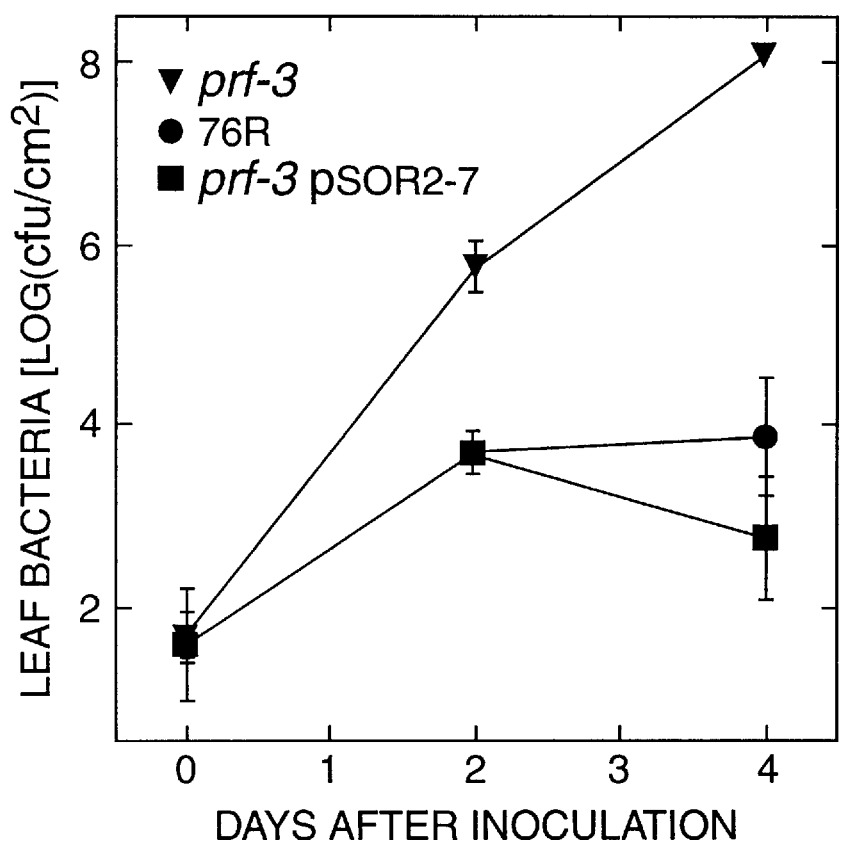

DNA gel blot analysis of the Prf locus in the prf-3 plant transformed with pSOR2-7 was also performed (FIG. 4). Genomic DNA was digested with XbaI, separated on a 0.75% agarose gel, and transferred to a Hybond N membrane. The blot was hybridized with a $^{32}$P-labeled probe corresponding to SOR2.

The results shown in FIG. 3A–C and FIG. 4 indicate that one SOR2-containing cosmid, pSOR2-7 complemented the prf-3 mutation, while pSOR1-3 did not complement the prf-3 mutation. As expected, resistance exhibited by the transgenic plants was strictly dependent upon the presence of the avrPto gene in the pathogen, as strain T1 caused disease on the plants transformed with pSOR2-7. However, poor disease symptoms were observed on the pSOR2-7 #3 plant, which exhibits non-specific disease resistance, as discussed below.

Figure 5:
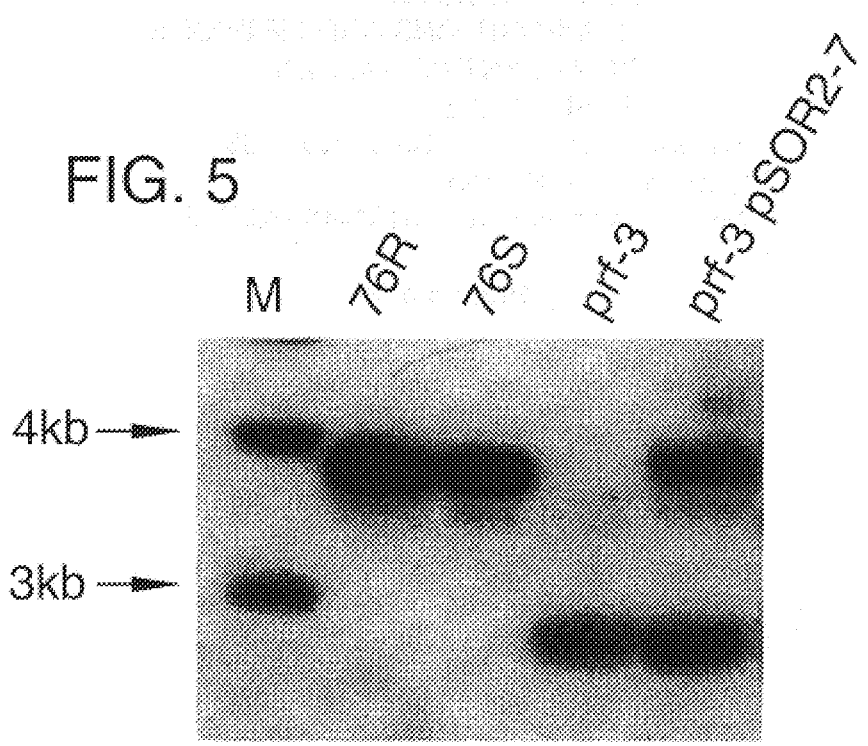

To quantify the level of resistance conferred by pSOR2-7, we monitored the kinetics of growth of T1 (avrPto) bacteria in prf-3 plants transformed with pSOR2-7 and vacuum infiltrated with T1(avrPto) at a concentration of $5 \times 10^4$ cfu/mL. Bacterial concentrations in plant leaves were assayed after 0, 2 and 4 days. Transgenic plants containing pSOR2-7 displayed a 1000-fold reduction in bacterial growth relative to untransformed prf-3 plants (FIG. 5). This level of resistance is comparable to that observed between the wild-type resistant line 76R and the mutant line prf-3 (Salmeron et al., *Plant Cell* 6:511–520, 1994).

Figure 3D:
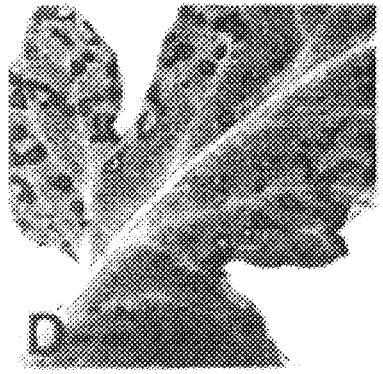
Figure 3E:
Figure 3F:
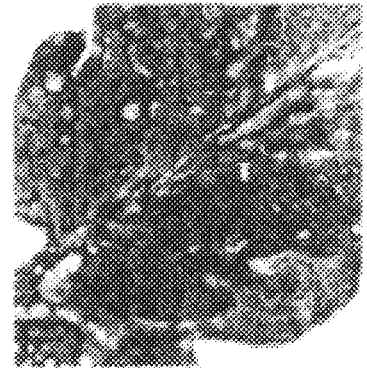

If pSOR2-7 contained the Prf gene, then it would also be predicted to confer Fenthion sensitivity to prf-3 tomatoes. Plants were dipped in a 4 mL/L solution of fenthion (Baytex 4; Mobay Chemicals, Kansas City, Mo.) and photographed after three days. Whereas prf-3 tomatoes and pSOR1-3 transformants showed no symptoms following Fenthion treatment, pSOR2-7 transformants developed necrotic specks at least as severe as those observed on wild-type 76R plants (FIG. 3D and F). These results indicate that pSOR2-7 contains a gene or genes conferring both Pst(avrPto) resistance and Fenthion sensitivity in tomato.

Figure 6:
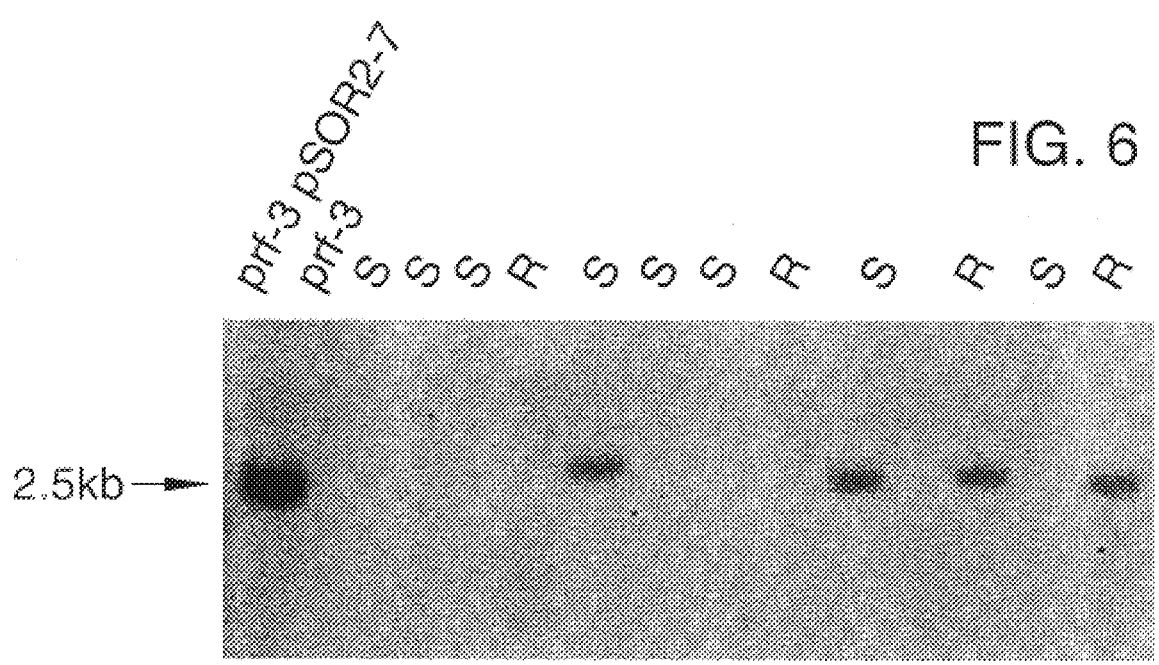

To confirm that disease resistance and Fenthion sensitivity in the transgenic plants was conferred by pSOR2-7, pSOR2-7 transformants were test-crossed to prf-3 mutant plants. Genomic DNAs from prf-3 mutant lines transformed with pSOR2-7 were digested with BglII, separated on an 0.75%.agarose gel, and transferred to a Hybond N membrane. The blots were hybridized with the 2.5 kb BglII fragment of pCDL04541. Plants were screened for resistance to T1 (avrPto) by dipping in a solution of 10 mM $MgCl_2$, 0.05% Silwet L-77 (Union Carbide) containing $2 \times 10^8$ cfu/mL of T1(avrPto) and scored after five days. Progeny were analyzed for resistance to Pst strains expressing avrpto, and inheritance of transformed DNA from the vector pCDL04541. A strict correlation between the two traits was observed, indicating that the phenotypes of the transformants were conferred by the introduced cosmid DNA (FIG. 6).

Molecular Cloning of the Prf Gene. Complementation of prf-3 by pSOR2-7 and mapping of the 1-kb deletion in prf-3 to SOR2 provided strong evidence that the Prf coding region lies at least partially within SOR2. To identify genes expressed from the SOR2 region that would be candidates for the Prf gene, cDNA libraries constructed from lines 76R and VFNT Cherry were probed with SOR2. Clones of 1.1 and 1.2 kb, respectively, were the longest isolated from each library and were selected as candidate clones for the Prf gene.

Analysis of the CDNA clones indicated that the 3' ends mapped within a 3.8 kb EcoRI fragment downstream of SOR2, and that the clones were partial cDNAs each containing a single open reading frame extending completely to the 5' end of the insert. Therefore, we sequenced the entire SOR2 fragment plus 1.05 kb downstream (to a point corresponding to the ends of the CDNA clones) from both 76R and VFNT Cherry DNAs. Primers corresponding to sequences throughout SOR2 were then used to amplify the complete transcribed region of Prf from reverse-transcribed 76R mRNA using both RT-PCR and 5' RACE approaches (Experimental Procedures). The longest clone obtained from RT-PCR was 4.0 kb in length and was designated pBS-Prf, while the RACE analysis indicated a transcript of 5.7 kb in length. After adding the sequence of the Prf 3'-untranslated region as determined from sequencing the shorter cDNA clones (most of this was not incorporated into the RT-PCR products) the full length of the Prf mRNA was predicted to be 6.2 kb.

Figure 7A:
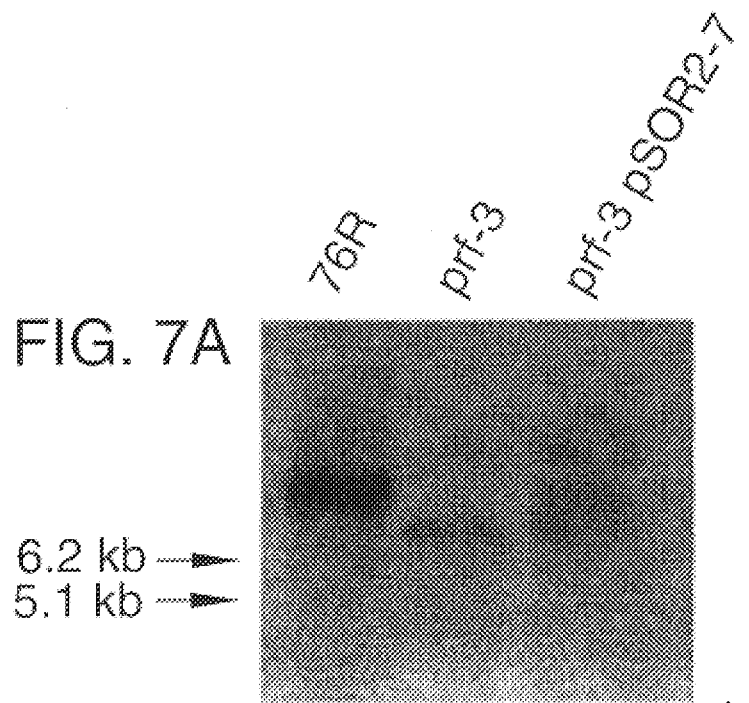
Figure 7B:
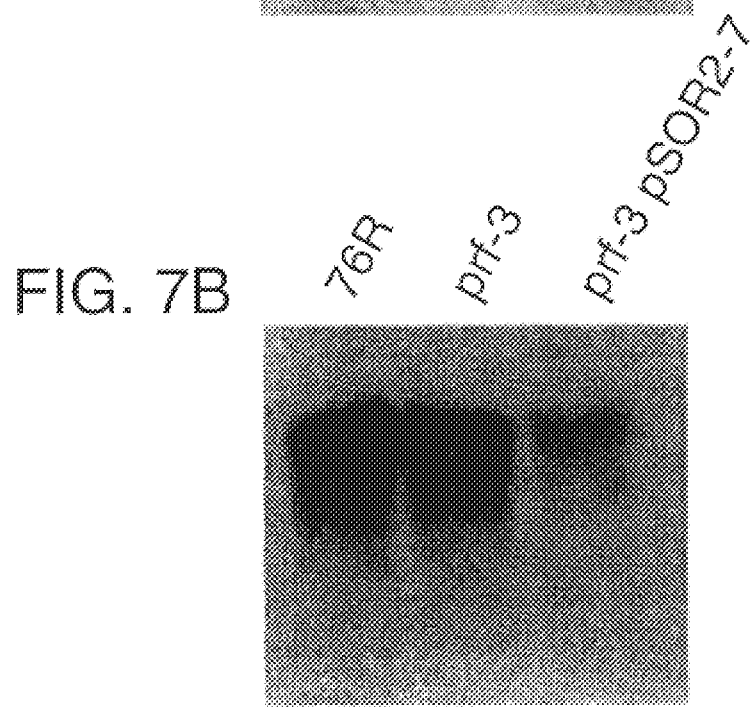

The size of the Prf mRNA was confirmed by RNA gel blot analysis. Hybridization to the radiolabeled insert of pBS-Prf reveals a mRNA of approximately 6.2 kb in wild-type 76R leaf tissue (FIG. 7, lane 1). This message is approximately 1.1 kb shorter in the prf-3 mutant (lane 2). Transformants of prf-3 containing pSOR2-7 express both sizes of mRNA (lane 3). Since RNA for this experiment was taken from uninoculated plant tissue, induction by pathogen attack is not required for expression of the Prf gene in tomato.

Nucleotide Sequence of the Prf Gene and Analysis of Mutant Alleles. The insert of the pBS-Prf cDNA along with the 5' RACE products were sequenced (FIG. 9 (SEQ ID NO: 1)) and found to encode a 1824 amino acid protein of 209.7 kDa (FIG. 11 (SEQ ID NO: 3)). Analysis of the Prf amino acid sequence shows that the protein falls into the class of resistance gene products recently identified in numerous plant species that contain putative nucleotide binding sites and leucine-rich-repeats. Of the three motifs comprising the predicted ATP/GTP binding site, the "P-loop" domain (Saraste et al., *Trends Biochem. Sci.* 15:430–434, 1990) occurs at residues 1120–1132, followed by the companion kinase domains 2 and 3a at 1195–1205 and 1224–1231, respectively. Beginning at residue 1398 is a sequence resembling leucine-rich repeat domains with approximately fourteen to eighteen imperfect copies of the leucine-rich repeat motif with a consensus sequence of LXXLXXLXXLXLXXN/CXXLXXIPSX (FIG. 12 (SEQ ID NO: 4)). Other notable features of the Prf protein that are shared by other resistance gene products include a leucine zipper (Roxrigues and Park, *Mol. Cell Biol.* 13:6711–6722, 1993) spanning residues 959–994. The block of residues from 716–858 comprise two copies of a direct repeat, with 49% amino acid identity between the two copies (FIG. 13). Also present is a string of seven amino acids (1058–1064) that corresponds precisely to one half of the binding site for interleukin-8 in the mammalian interleukin-8 receptor (Hébert et al., *J. Biol. Chem.* 268:18549–18553, 1993).

Figure 8:
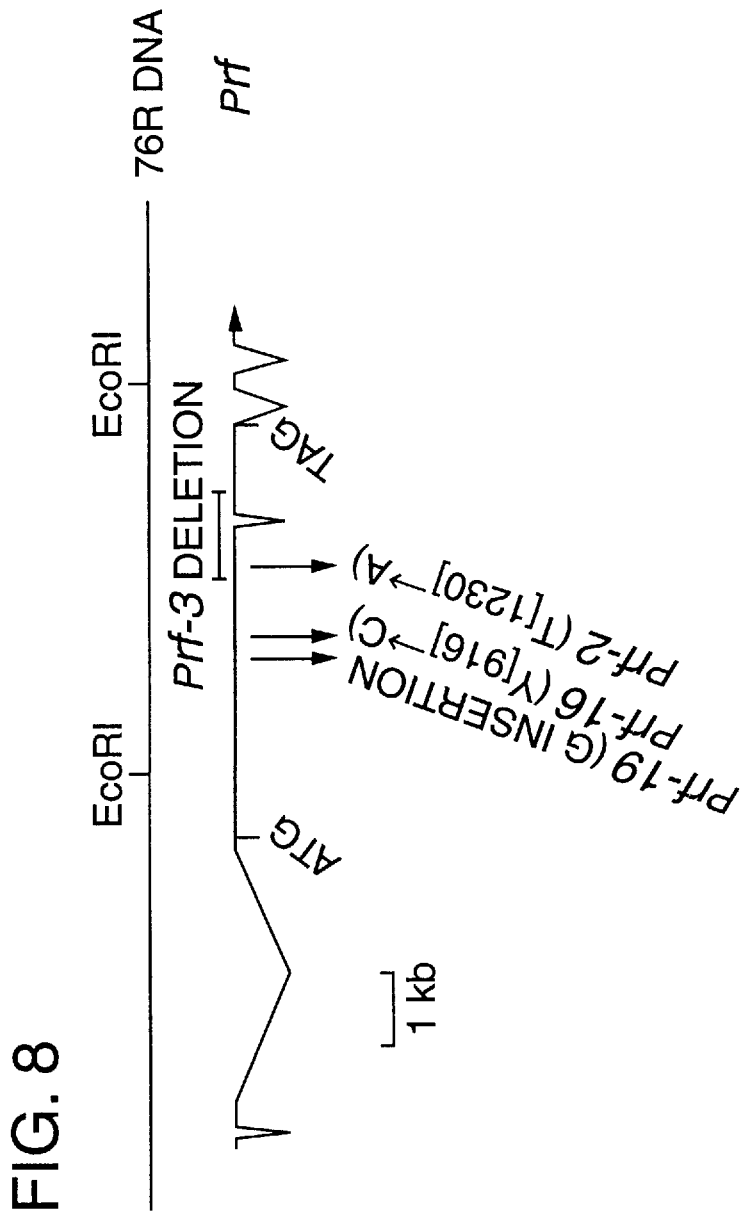

Analysis of the genomic sequence of Prf from 76R (FIG. 10 (SEQ ID NO: 2)) revealed the presence of five introns. Two lie within the leader MRNA, including a large 3.6 kb intron occurring 43 nucleotides upstream of the initiator ATG. A third intron occurs between the regions encoding the P-loop and leucine-rich repeat motifs and sits between residues 1436–1437, and an additional two introns occur in the trailer mRNA (FIG. 8). A comparison of portions of the genomic Prf alleles from 76R and VFNT Cherry revealed extremely high similarity, with the encoded proteins 99.2% identical at the amino acid level across the carboxy-terminal 1128 amino acids. This is consistent with genetic evidence showing that naturally-occurring lines of tomato that do not carry a functional Pto, do carry functional copies of Prf (Salmeron et al., *Plant Cell* 6:511–520, 1994).

The mutant alleles from four prf plants were amplified from genomic DNAs using Prf-specific primers. Partial sequences were determined and compared to the wild-type gene to identify the genetic alterations in the prf mutant plants. It was confirmed that the prf-3 mutant carries a simple 1.1 kb deletion between the coding regions for the nucleotide binding site and leucine-rich-repeat motifs (FIG. 2), which deletion results in a truncated protein of approximately 1160 amino acids. Two other mutants (prf-2 and prf-16) carried single base changes which resulted in encoded proteins with single amino acid alterations relative to the wild-type sequence. The Prf-2 protein carries a Thr to Ala change at position 1230 that eliminates a residue conserved in the third portion of the nucleotide binding motif, while the Prf-16 protein carries a Tyr to cys alteration at residue 916. Finally, the prf-19 allele was found to carry an insertion of a G residue, resulting in a frameshift. The protein encoded by prf-19 contains a wild-type sequence to amino acid 860, continuing thereafter with Gly and Ser residues before terminating (FIG. 8). These results were based on the nucleotide sequence of the SOR2 region and did not include the entire 5' end of the gene. It is possible that other mutations also lie within this region. In combination with the complementation data described above, the identification of genetic alterations in four prf mutant alleles provides additional evidence that the cDNA we have isolated corresponds to the Prf gene.

Figure 14:
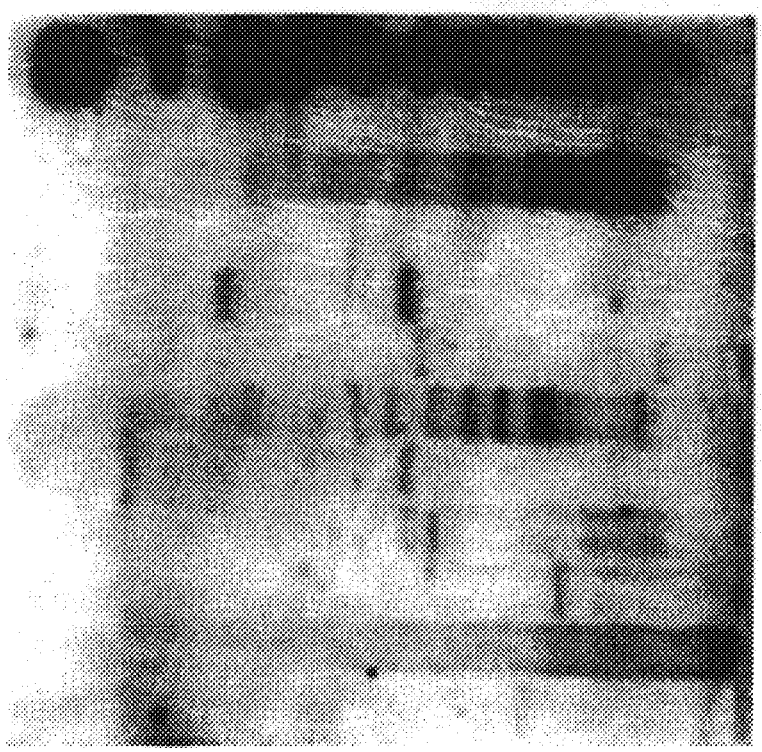

Homology of Prf to Genes in Other Plants. DNA gel blot analysis indicated that fragment(s) homologous to Prf exist in many plant species (FIG. 14). Using moderately high stringency hybridization conditions (see Experimental Procedures), most species tested showed one or two homologous fragments, while a large homologous gene family of approximately nine members was detected in tobacco. Multiple homologous bands were also detected in DNA from resistant tomato plants, indicating that Prf is a member of a gene family of approximately eight members.

Positioning Prf Relative to the Pto and Fen Genes. We were interested in determining the physical arrangement of the Prf, Pto and Fen genes within the Prf/Pto region. Cosmids containing the Pto and Fen genes were identified from the 76R contig (FIG. 1D) by PCR amplification of the respective genes from cosmid DNAs using gene-specific primers. Genes were assigned to individual restriction fragments by probing restricted cosmid DNAs with both the resulting PCR fragments and the cloned Pto and Fen genes. These data have recently been confirmed by preliminary sequence analysis of the Prf/Pto region. The summary of our results is depicted in FIG. 1D. The 3' end of the Prf cDNA is located approximately 500 bp from the ORF of the Fen gene and approximately 24 kb from the ORF of the Pto gene.

Broad-Spectrum Resistance to Plant Pathogens. A prf-3 mutant tomato plant was transformed with a cosmid clone that contained a wild-type copy of the Prf gene. One of the transformants, prf-3 pSOR2-7 #3 was resistant to Pst strain T1 (avrPto) and sensitive to fenthion, as expected. However, in contrast to another transformant, pSOR2-7 #3 was extremely sensitive to fenthion applications.

Figure 15A:
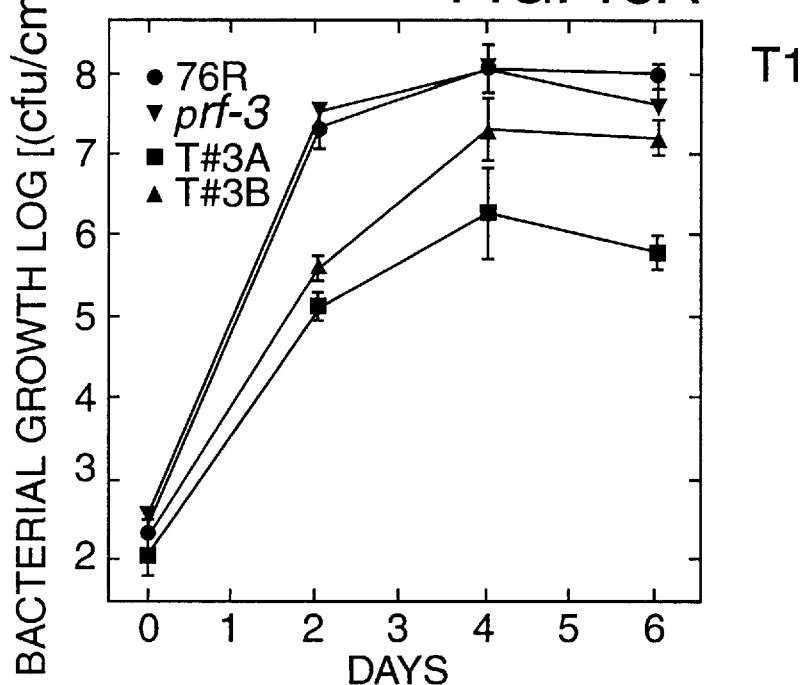
Figure 15B:
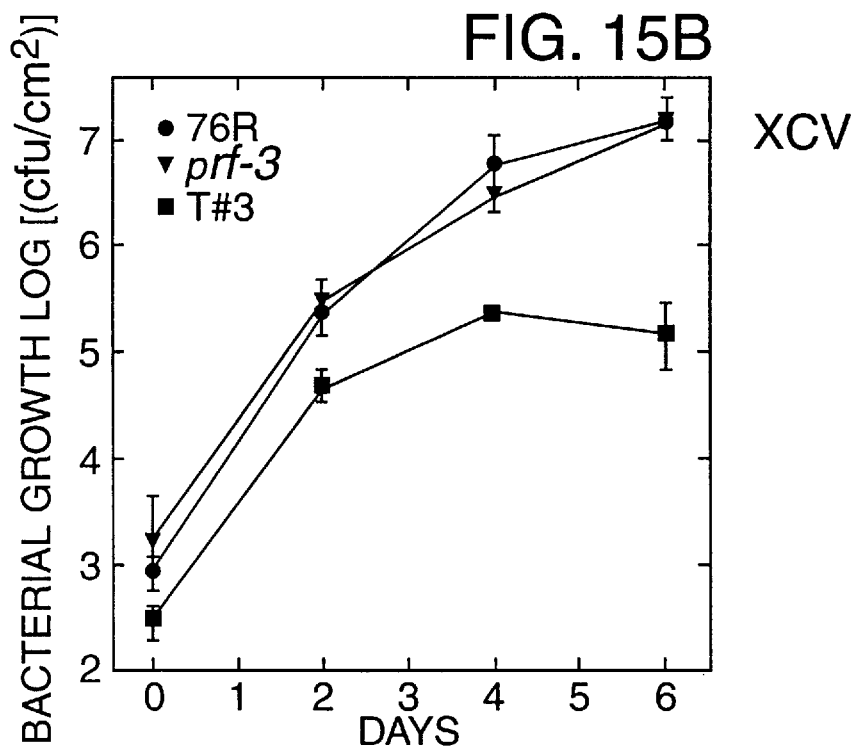

The prf-3 pSOR2-7 #3 transgenic plant was inoculated by vacuum filtration with *Xanthomonas campestris* pv. *vesicatoria* strain p38, and bacterial concentrations in plant leaves were assayed after 0, 2, 4, and 6 days. As shown in FIG. 15, pSOR2-7 #3 was resistant not only to Pst strain T1 lacking the avrPto gene but also to *Xanthomonas campestris* pv. *vesicatoria* strain p38. These results suggest that plants expressing the Prf transgene may be resistant to a wide variety of plant pathogens, including bacteria, viruses, fungi, and nematodes.

Additional characterization of pSOR2-7 #3 suggests that this plant contains more than one copy of the T-DNA. High-level expression of the Prf gene is likely responsible for the broad-spectrum resistance to phytopathogens observed in plants expressing the Prf transgene.

Discussion

The cloning of plant disease resistance genes has demonstrated that diverse plant species utilize proteins with a shared organization of structural motifs for defense against a wide range of pathogens (Staskawicz et al., Science 268:661–667, 1995). These motifs include a "P-loop" region that serves as part of a nucleotide triphosphate binding site, and a "leucine-rich repeat" (LRR) thought to form a site for interaction with other proteins (Kobe and Deisenhofer, Trends Biochem. Sci. 19:415–421, 1994). LRR-type plant disease resistance gene products form two subclasses (Jones et al., Science 266:789–792, 1994). Proteins in the first subclass contain the P-loop in the N-terminal half of the protein and the LRR near the carboxyl terminus. In these proteins the repeats within the LRR tend to be poorly conserved, and most closely match the repeat consensus found in yeast adenylate cyclase (Kataoka et al., Cell 43:493–505, 1985). These proteins do not contain signal sequences and thus may localize to the plant cytoplasm. The second subclass of resistance gene products lack an apparent nucleotide binding site but contain a signal sequence that may function to target the protein to the cytoplasmic membrane. The repeats within the LRR, found in the amino-terminal portion of the protein, are well-conserved and most closely resemble those found in plant polygalacturonase inhibitor proteins (Stotz et al., Plant Mol. Biol. 25:607–617, 1994).

Prf falls into the first protein subclass. Two other proteins that function in resistance to strains of Pseudomonas syringae, the Arabidopsis RPS2 and RPM1 proteins (Bent et al., Science 265:1856–1860, 1994; Grant et al., Science 269:843–846, 1995; Mindrinos et al., Cell 78:1089–1099, 1994), are also members of the first protein subclass, perhaps reflecting a common mechanism by which the elicitors produced under control of the corresponding avirulence genes are presented or perceived.

Construction of chimeras between different cloned resistance genes, and analysis of naturally-occurring and engineered mutant alleles can be used, for example, to identify domains that provide the specificity of recognition. For the Cf-9 and Prf genes, the availability of elicitors or elicitor-like molecules (Fenthion) (Carland and Staskawicz, Mol. Gen. Genet. 239:17–27, 1993; van Kan et al., Mol. Plant-Microbe Interact. 4:52–59, 1991) facilitates these and other studies addressing the roles of resistance gene products in ligand binding and signal transduction.

In tomato, the Pto and Fen kinases are required for transduction of pathogen elicitor and Fenthion signals to induce, in the case of Pto, disease resistance with associated hypersensitivity (Martin et al., Science 262:1432–1436, 1993), and in the case of Fen, a hypersensitive-like necrosis (Martin et al., Plant Cell 6:1543–1552, 1994; Rommens et al., Plant Cell 7:249–257, 1995). Since Prf is required for both these phenotypes (Salmeron et al., Plant Cell 6:511–520, 1994), the Prf protein must be a component common in the signaling pathways containing the Pto and Fen kinases. By analogy to some mammalian hormone receptors (Braun et al., EMBO J. 10:1885–1890, 1991) and to the Drosophila Toll protein (Hashimoto et al., Cell 52, 269–279, 1988), to which the tobacco N resistance gene product is similar (Whitham et al., Cell 78:1101–1115, 1994), Prf may function as a receptor that binds the pathogen elicitor or Fenthion and transduces the signal directly to either of the kinases, which may be membrane-associated. Alternatively, other proteins may serve as intermediaries between Prf and Pto/Fen or Prf may lie downstream of Pto and Fen in their respective signaling pathways. It has been shown that the Ptil protein kinase acts downstream of Pto (Zhou et al., *Cell* 83:925–935, 1995). If Prf is a downstream component in the tomato resistance pathway, it is likely that Prf is the recipient of a signal transduced by one or more protein kinase cascades.

The pathway involved in resistance of rice to bacterial blight, in which the Xa21 gene confers resistance to *Xanthomonas oryzae*, is the only pathway other than the Prf/Pto pathway demonstrated to involve both an LRR-containing protein and a protein kinase (Song et al., *Science* 270:1804–1806, 1995). Remarkably, the LRR and kinase domains both reside on the Xa21 protein (Song et al., *Science* 270:1804–1806, 1995). The Prf and Pto proteins may be derived from an ancestral tomato resistance factor in which the LRR and protein kinase domains were fused. The physical proximity between the Prf and Pto genes suggests the possibility of such an evolutionary relationship.

Although the Prf/Pto and Xa21 pathways may be unique in involving protein kinases in disease resistance signaling, it is more likely that the corresponding protein kinases in other systems have not yet been identified, perhaps due to functional redundancy. Most mutations at the Pto locus are weak alleles that cause only partial susceptibility to Pst strains that express avrpto. Mutations at Prf completely abolish resistance (Salmeron et al., *Plant Cell* 6:511–520, 1994). This may reflect a functional redundancy among members of the Pto gene family in wild-type plants. Homologs of Pto exist in many plant species (Martin et al., *Science* 262:1432–1436, 1993). If these homologs function in disease resistance pathways in their respective hosts, they may also exist as gene families with multiple functional members.

Figure 2:
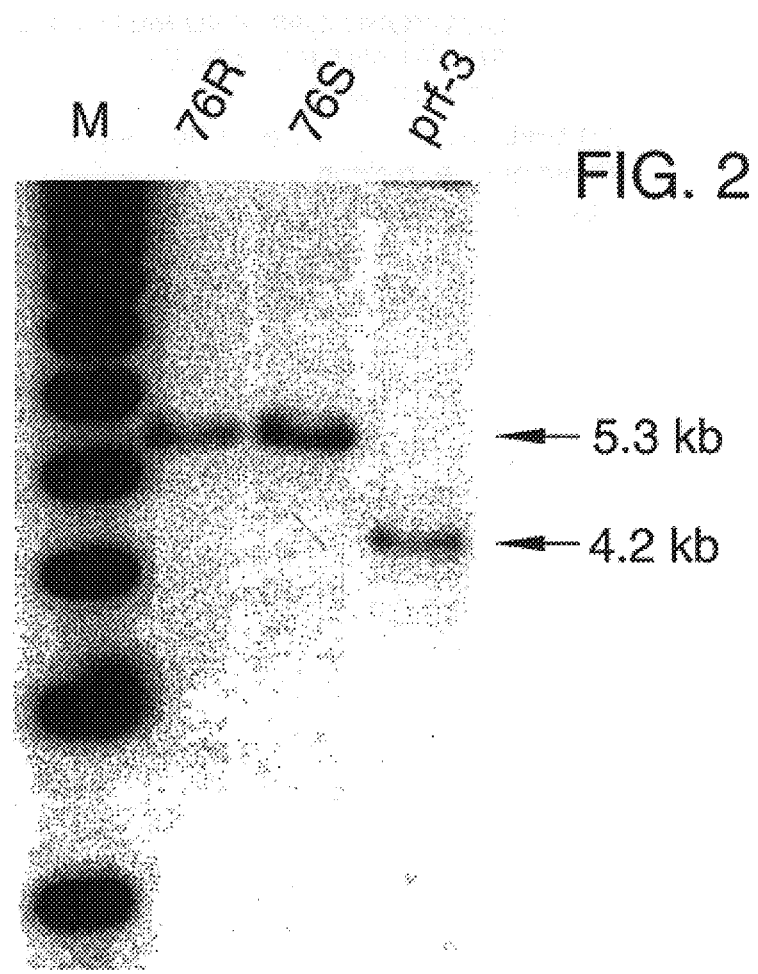

The Prf gene is located within the Pto gene cluster, immediately adjacent to the Fen gene (FIG. 1). The proximity of Prf to Pto and Fen, genes with which Prf cooperates in disease resistance signaling, is reminiscent of Brassica species in which two genes that control self-incompatibility, SLG and SRK, lie within a distance of 200 kb (Boyes and Nasrallah, *Mol. Gen. Genet.* 236:369–373, 1993). By further analogy, the SRK gene encodes a receptor kinase proposed to interact with the SLG-encoded glycoprotein in initiating the self-incompatibility reaction (Stein et al., *Proc. Natl. Acad. Sci. USA* 88:8816–8820, 1991), which, like the plant defense response, involves restricting the growth of an invading organism (in this case, the pollen tube).

The potential for Prf to couple with distinct kinases in transduction of different signal molecules may be important in lending the flexibility required by the host to counteract ongoing pathogen evolution. The avrPto gene appears to be dispensable for growth of Pst in cell culture and in infected plants (Ronald et al., *J. Bacteriol.* 174:1604–1611, 1992). Pst strains lacking avrPto are known to arise in fields heavily planted with Pto cultivars. It would be advantageous for the host to be able to recognize altered forms of pathogen elicitors, which may be most easily achieved through differential coupling of distinct but related signaling components. The occurrence of Pto and Prf as members of multi-gene families may allow for additional diversity through recombinational processes (Sudapak et al., *Genetics* 133:119–125, 1993) that could prove advantageous to tomato lines in the face of an ever-changing Pst population.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. An isolated nucleic acid molecule encoding a protein comprising an amino acid sequence as shown in SEQ ID NO: 3.

2. The nucleic acid molecule according to claim 1 wherein the molecule comprises a nucleic acid sequence selected from the group consisting of SEQ ID NOS: 1 and 2.

3. A recombinant nucleic acid molecule comprising a promoter sequence operably linked to the nucleic acid molecule according to claim 1.

4. A cell transformed with the recombinant nucleic acid molecule according to claim 3.

5. A transgenic plant comprising the recombinant nucleic acid molecule according to claim 3.

6. An oligonucleotide comprising at least 20 contiguous nucleotides of a sequence selected from the group consisting of SEQ ID NOS: 1 and 2.

7. The oligonucleotide according to claim 6 wherein the oligonucleotide comprises at least 30 contiguous nucleotides of a sequence selected from the group consisting of SEQ ID NOS: 1 and 2.

8. An oligonucleotide comprising at least 20 contiguous nucleotides of SEQ ID NO:2.

9. The oligonucleotide according to claim 8 wherein the oligonucleotide comprises at least 30 contiguous nucleotides of SEQ ID NO:2.

10. An isolated nucleic acid molecule encoding a polypeptide comprising an amino acid sequence selected from the group consisting of:

(a) the sequence set forth in SEQ ID NO:3; and (b) a sequence that differs from the sequence set forth in SEQ ID NO:3 by one or more conservative amino acid substitutions, and wherein the polypeptide has Prf biological activity.

11. A recombinant nucleic acid molecule comprising a promoter sequence operably linked to the nucleic acid molecule according to claim 10.

12. A cell transformed with the recombinant nucleic acid molecule according to claim 11.

13. A transgenic plant comprising the recombinant nucleic acid molecule according to claim 11.

14. An isolated nucleic acid molecule that:

(a) hybridizes with a nucleic acid probe comprising nucleotides 3150–4494 of SEQ ID NO:1 under wash conditions of 65° C., 0.5XSSC and 0.5% SDS for 1 hour; and (b) encodes a protein having Prf biological activity.

15. A recombinant nucleic acid molecule comprising a promoter sequence operably linked to the nucleic acid molecule according to claim 14.

16. A cell transformed with the recombinant nucleic acid molecule according to claim 15.

17. A transgenic plant comprising the recombinant nucleic acid molecule according to claim 15.

18. An isolated nucleic acid molecule that:

(a) hybridizes with a nucleic acid probe comprising the sequence shown in SEQ ID NO:2 under wash conditions of 65° C., 0.5XSSC and 0.5% SDS for 1 hour; and (b) encodes a protein having Prf biological activity.

19. A recombinant nucleic acid molecule comprising a promoter sequence operably linked to the nucleic acid molecule according to claim 18.

20. A cell transformed with the recombinant nucleic acid molecule according to claim 19.

21. A transgenic plant comprising the recombinant nucleic acid molecule according to claim 19.

22. An isolated nucleic acid molecule encoding a tomato Prf protein.

23. A recombinant nucleic acid molecule comprising a promoter sequence operably linked to the nucleic acid molecule according to claim 22.

24. A cell transformed with the recombinant nucleic acid molecule according to claim 23.

25. A transgenic plant comprising the recombinant nucleic acid molecule according to claim 23.

\* \* \* \* \*

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
( A ) LENGTH: 5475 base pairs
( B ) TYPE: nucleic acid
( C ) STRANDEDNESS: double stranded
( D ) TOPOLOGY: linear ( x i ) SEQUENCE DESCRIPTION: SEQ ID NO:1:

```
ATGGCCAAGG  AGTGTCGCGA  TGCAATAGGT  ACTATAAACC  TTGTGAAGGG  CCAGCATTTA      60

GACAGAAGGA  CCACTAATCA  ATTGGAGGAT  GCTATAAAGC  ACCTAACACA  TGTTGCTGTA     120

TTTCTCACAA  ATCTGGAGAA  GCGTCACCCT  GCTAATGGAA  TATCTATACA  TCTTAGGCCT     180

CTATTTTTAG  AAGCTCATGA  TGGCTTTTCT  CTGATGTGTT  CTCATCCTCC  TCGTTCTCAG     240

TTTACCGTTA  AACTGGATAA  CATTGCTGAG  AAATTCAAAT  CTTCAAAGGC  GTCAAGATCA     300

ACAAGGCAAG  TGATCCCAGA  GCTGCTGCAA  ATAATTGAAC  CCGAGAATAT  TGCTAAGCGA     360

ATCAAAGCTT  CAAAGCCATC  AAGATCATCT  AGCCCAATCA  CTGTGGATAT  GGTGGGGTTT     420

ATCGAATCCT  TGCTTGGTTC  TGTTCATCGT  GCATTGTTCT  TTATCAGTGC  AGGGCCTCCT     480
```

```
GTGTCTATGC  TTGACAAGAA  GCTTCGACAT  CTACAAGTCT  TCTTTAGACT  AATTTCAAAG   540
CGGGGCATTG  AGCATGAGAG  TATGAAGGAT  CTCTTCTACC  ATGTTGAGGA  TGTAGCTTAC   600
ACTGCAGCAC  AACTATGTGT  CTTGGGGTCG  AGCTGCCATA  TGGATGACGA  GTTCTCTAAA   660
TTTCTGGAAA  GGATAAGTCG  TCCTTTTAGC  CCAGGATTGA  GGCAGGTTTA  TCTCAATGCC   720
TTGATAGGGT  TAAATTCATC  AAGATCAAAG  ACTACAATGA  ATGCCAAATA  TATGCTTGAT   780
TTTGTTAGTG  CTCTCCAAGA  TGATCTGAGA  CTAAGATGTG  ATAATCGAAT  TCGATGGCTC   840
CAACGAGGAC  TTTCTTACCT  TTGTCGATTC  CTCAGGGACA  TAGAATCTTA  TCCTGTTTCA   900
CATCGACAAC  TGATTTCTCT  TCAATTGAAT  ATGGAAGATC  TGGCTATTGG  GTCTGCAAAT   960
GCCATCTACT  CCTATGATGA  GGATATGGAT  AAGACTAGTG  AAATAGACCA  TGAGCTTTTT  1020
CATTTGCAAA  TGAAGTTTAA  TTATGTTAAA  GTAGAGGTTG  ATCTGATTCG  TCTACAAAAC  1080
ATTCAAGGCA  CCATAATAGT  TCCTATGAAA  GATCTGATCG  ACTATGTTTG  GAAGAGCTG   1140
ATGTTCTTTA  GAAGTTATTT  CATGGATGCA  TTCGACCAGT  TTAAAGAGCA  GACCAGGATA  1200
ACTGTTATTT  TGAACTATAT  TCAGTCTGCA  GTTAGTCAAG  CATGGTCAGT  CTGTGATTCT  1260
CTTTGTCATG  ACTTGAATCA  AAATGACTTG  GCCAGGGAAA  TTAATTGCTT  GCATTTTCAA  1320
TTGCTTCTTA  AGTTCAAGTT  TATCAAGGTC  GCTATTAGAC  AGATGTGTCC  CAGCATTTCT  1380
GCATCATCAA  CACCAGACCA  TCCAATGATA  GATCTGCTGA  ACTTCTTCC   CATGAACTTT  1440
GAGGCCATTG  ATTCCTATTC  CAGCATGCTA  AAAGCCTCCT  GTCCATCTTC  CTCACATCGT  1500
CCTAATAGGG  ATGCGGAATC  CCCCAATACA  TCATTCTTAT  GTGGTCCCAA  TACAGATGTG  1560
TACTCCTTCT  ATTCATCATC  CTCACGTATT  CCCAAGATGG  ATGAGATATT  GAAGAGGTTT  1620
CATGAATATA  TTCTTGTCAA  TCTGCTACGG  AAGGATGAAA  CCAATTTGAC  ATTTACTATT  1680
GCAGATGAGG  TCAAAAAGTT  TTATGAAGGG  TTGTTGCTCA  TGGTTACATA  TCTTATTGAA  1740
CCTCCAGTTC  CTCACACTGA  ATGCAGGAAG  CAAAATGATC  TCTCAATGCG  ACATGAAGCT  1800
GTTGCAATTG  AGGCGGAATC  TGCTGTGTGT  TTACATTATG  AGGATAATAT  GAATAACAAC  1860
AGTAGGGAGA  TCAATCAGGT  ACTTCAGTTT  TTGACTGTGA  CTTTCTGGCT  TATCAAGTCT  1920
GAGGGTAACT  TGATGGATCT  ACTGAAGCAC  AAATCCACTT  TGGGAAATCA  AGTTCTAGAT  1980
CTGATTGAGA  GTGCTCATGA  AGAGCTTATT  CTCCTTAGAT  CTATTCTCAT  GGATCTTCTT  2040
AGGAAAAAGC  TTTACAGATT  GGATGATCTC  TTAATGCATG  CTGAGGTGAC  TGCAAAAAGG  2100
TTAGCAATAT  TCAGTGGTTC  TTGTTATGAA  TATTTCATGA  ACGGAAGCAG  CACTGAGAAA  2160
ATGAGGCCCT  TGTTATCTGA  TTTTCTGCAA  GAGATTGAGT  CTGTCAAGGT  AGAGTTCAGA  2220
AATGTTTGCT  TGCAAGTTCT  GGATATATCA  CCTTTTTCCC  TGACAGATGG  AGAAGGCTT   2280
GTTAATTTCT  TATTAAAAAA  CCAGGCCAAG  GTGCCGAATG  ATGATGCTGT  TTCTTCTGAT  2340
GGAAGTTTAG  AGGATGCAAG  CAGCACTGAG  AAAATGGGAC  TTCCATCTGA  TTTTCTCCGA  2400
GAGATTGAGT  CTGTTGAGAT  AAAGGAGGCC  AGAAAATTAT  ATGATCAAGT  TTTGGATGCA  2460
ACACATTGTG  AGACGAGTAA  GACAGATGGA  AAAAGCTTTA  TCAACATTAT  GTTAACCCAA  2520
CAGGACAAGT  TGCCGGACTA  TGATGCTGGT  TCAGTCTCTT  ATCTTCTTAA  CCAAATATCA  2580
GTAGTTAAAG  ACAAATTATT  GCACATTGGC  TCTTTACTTG  TAGATATTGT  ACAGTACCGG  2640
AATATGCATA  TAGAACTTAC  AGATCTCGCT  GAACGTGTTC  AAGATAAAAA  CTACATTTGT  2700
TTCTTCTCTG  TCAAGGGTTA  TATTCCTGCT  TGGTATTACA  CACTATATCT  CTCTGATGTC  2760
AAGCAATTGC  TTAAGTTTGT  TGAGGCAGAG  GTAAAGATTA  TTTGTCTGAA  AGTACCAGAT  2820
TCTTCAAGTT  ATAGCTTCCC  TAAGACAAAT  GGATTAGGAT  ATCTCAATTG  CTTTTTAGGC  2880
```

| | | | | | | |
|---|---|---|---|---|---|---|
| AAATTGGAGG | AGCTTTTACG | TTCTAAGCTC | GATTTGATAA | TCGACTTAAA | ACATCAGATT | 2940 |
| GAATCAGTCA | AGGAGGGCTT | ATTGTGCCTA | AGATCATTCA | TTGATCATTT | TTCAGAAAGC | 3000 |
| TATGATGAGC | ATGATGAAGC | TTGTGGTCTT | ATAGCAAGAG | TTTCTGTAAT | GGCATACAAG | 3060 |
| GCTGAGTATG | TCATTGACTC | ATGCTTGGCC | TATTCTCATC | CACTCTGGTA | CAAAGTTCTT | 3120 |
| TGGATTTCTG | AAGTTCTTGA | GAATATTAAG | CTTGTAAATA | AAGTTGTTGG | TGAGACATGT | 3180 |
| GAAAGAAGGA | ACATTGAAGT | TACTGTGCAT | GAAGTTGCAA | AGACTACCAC | TTATGTAGCA | 3240 |
| CCATCTTTTT | CAGCTTATAC | TCAAAGAGCA | AACGAAGAAA | TGGAGGGTTT | TCAGGATACA | 3300 |
| ATAGATGAAT | TAAAGGATAA | ACTACTTGGA | GGATCACCTG | AGCTTGATGT | CATCTCAATC | 3360 |
| GTTGGCATGC | CAGGATTGGG | CAAGACTACA | CTAGCAAAGA | AGATTTACAA | TGATCCAGAA | 3420 |
| GTCACCTCTC | GCTTCGATGT | CCATGCTCAA | TGTGTTGTGA | CTCAATTATA | TTCATGGAGA | 3480 |
| GAGTTGTTGC | TCACCATTTT | GAATGATGTC | CTTGAGCCTT | CTGATCGCAA | TGAAAAGAA | 3540 |
| GATGGTGAAA | TAGCTGATGA | GTTACGCCGA | TTTTTGTTGA | CCAAGAGATT | CTTGATTCTC | 3600 |
| ATTGATGATG | TGTGGGACTA | TAAAGTGTGG | GACAATCTAT | GTATGTGCTT | CAGTGATGTT | 3660 |
| TCAAATAGGA | GTAGAATTAT | CCTAACAACC | CGCTTGAATG | ATGTCGCCGA | ATATGTCAAA | 3720 |
| TGTGAAAGTG | ATCCCCATCA | TCTTCGTTTA | TTCAGAGATG | ACGAGAGTTG | GACATTATTA | 3780 |
| CAGAAAGAAG | TCTTTCAAGG | AGAGAGCTGT | CCACCTGAAC | TTGAAGATGT | GGGATTTGAA | 3840 |
| ATATCAAAAA | GTTGTAGAGG | GTTGCCTCTC | TCAGTTGTGT | TAGTAGCTGG | TGTTCTGAAA | 3900 |
| CAGAAAAAGA | AGACACTAGA | TTCATGGAAA | GTAGTAGAAC | AAAGTCTAAG | TTCCCAGAGG | 3960 |
| ATTGGCAGCT | TGGAAGAGAG | CATATCTATA | ATTGGATTCA | GTTACAAGAA | TTTACCACAC | 4020 |
| TATCTTAAGC | CTTGTTTTCT | CTATTTTGGA | GGATTTTGC | AGGGAAAGGA | TATTCATGTC | 4080 |
| TCAAAAATGA | CCAAGTTGTG | GGTAGCTGAA | GGGTTTGTAC | AAGCAAACAA | CGAAAAAGGA | 4140 |
| CAAGAAGATA | CCGCACAAGG | TTTCTTGGAC | GATCTTATTG | GTAGGAATGT | AGTGATGGCC | 4200 |
| ATGGAGAAGA | GACCTAATAC | CAAGGTGAAA | ACGTGCCGCA | TTCATGATTT | GTTGCATAAA | 4260 |
| TTCTGCATGG | AAAAGGCCAA | ACAAGAGGAT | TTTCTTCTCC | AAATCAATAG | TGGAGAAGGT | 4320 |
| GTATTTCCTG | AACGATTGGA | GGAATACCGA | TTGTTCGTTC | ATTCTTACCA | AGATGAAATT | 4380 |
| GATCTGTGGC | GCCCATCTCG | CTCTAATGTC | CGATCTTTAC | TATTCAATGC | AATTGATCCA | 4440 |
| GATAACTTGT | TATGGCCGCG | TGATATCTCC | TTCATTTTTG | AGAGCTTCAA | GCTTGTTAAA | 4500 |
| GTGTTGGATT | TGGAATCATT | CAACATTGGT | GGTACTTTTC | CCACTGAAAT | ACAATATCTA | 4560 |
| ATTCAGATGA | AGTACTTTGC | GGCCCAAACT | GATGCAAATT | CAATTCCTTC | ATCTATAGCT | 4620 |
| AAGCTTGAAA | ATCTTGAGAC | TTTTGTCGTA | AGAGGATTGG | GAGGAGAGAT | GATATTACCT | 4680 |
| TGTTCACTTC | TGAAGATGGT | GAAATTGAGG | CATATACATG | TAAATGATCG | GGTTTCTTTT | 4740 |
| GGTTTGCATG | AGAACATGGA | TGTTTTAACT | GGTAACTCAC | AATTACCTAA | TTTGGAAACC | 4800 |
| TTTTCTACTC | CACGTCTCTT | TTATGGTAAA | GACGCAGAGA | AGGTTTTGAG | GAAGATGCCA | 4860 |
| AAATTGAGAA | AATTGAGTTG | CATATTTTCA | GGGACATTTG | GTTATTCAAG | GAAATTGAAG | 4920 |
| GGTAGGTGTG | TTCGTTTTCC | CAGATTAGAT | TTTCTAAGTC | ACCTTGAGTC | CCTCAAGCTG | 4980 |
| GTTTCGAACA | GCTATCCAGC | CAAACTTCCT | CACAAGTTCA | ATTTCCCCTC | GCAACTAAGG | 5040 |
| GAACTGACTT | TATCAAAGTT | CCGTCTACCT | TGGACCCAAA | TTTCGATCAT | TGCAGAACTG | 5100 |
| CCCAACTTGG | TAATTCTTAA | GTTATTGCTC | AGAGCCTTTG | AAGGGGATCA | CTGGGAAGTG | 5160 |
| AAAGATTCAG | AGTTCCTAGA | ACTCAAATAC | TTAAAACTGG | ACAACCTCAA | AGTTGTACAA | 5220 |
| TGGTCCATCT | CTGATGATGC | TTTTCCTAAG | CTTGAACATT | TGGTTTTAAC | GAAATGTAAG | 5280 |

| | | | | | |
|---|---|---|---|---|---|
| CATCTTGAGA | AAATCCCTTC | TCGTTTTGAA | GATGCTGTTT | GCCTAAATAG | AGTTGAGGTG | 5340 |
| AACTGGTGCA | ACTGGAATGT | TGCCAATTCA | GCCCAAGATA | TTCAAACTAT | GCAACATGAA | 5400 |
| GTTATAGCAA | ATGATTCATT | CACAGTTACT | ATACAGCCTC | CAGATTGGTC | TAAAGAACAG | 5460 |
| CCCCTTGACT | CTTAG | | | | | 5475 |

( 2 ) INFORMATION FOR SEQ ID NO: 2:

( i ) SEQUENCE CHARACTERISTICS:
    ( A ) LENGTH: 10968 base pairs
    ( B ) TYPE: nucleic acid
    ( C ) STRANDEDNESS: double stranded
    ( D ) TOPOLOGY: linear ( x i ) SEQUENCE DESCRIPTION: SEQ ID NO:2:

| | | | | | |
|---|---|---|---|---|---|
| AATATTATAA | CTGTTGGAAA | ATGAACTCAA | CCATTCATCA | ATTATCTCAA | GAAGAAGACC | 60 |
| AGTATGAACT | CTAAGCTTAT | GGGTAAGTAA | TTTCTCTCTG | ATTTTCATAA | AATGAAAGAA | 120 |
| GAAATTGCAA | GTATTTACCT | TCATTTGCTT | TGTTAATTGC | AGGCAGCTAG | GACTTAAAAA | 180 |
| AAAATCATTG | AAGAAAGAG | TTTTCTGTTA | GATTTCAACC | ATCAAACACT | AAACGAAAAG | 240 |
| TAGTAAGTTG | TTTATTTTCC | TCTCTCATTT | ACTCAATATT | CTTAACTATA | AACTAATTGC | 300 |
| ATCTTATAAC | ACAGATCTGC | ATCCGTTTTT | GTTTTAAAT | TTTGAGAAAA | TGGTTAAAGC | 360 |
| CCCCTCCAAT | TACAAGCTCG | TACTTCACGG | GTGTCCTATC | ACTTTCCTGA | ACTGTTTAAT | 420 |
| GCAAGAATTA | TTACACTCCT | AAAACGTCAT | AACCACATCT | ATGCTAATGA | GTGAGACTCA | 480 |
| CTCTTTGCAG | AAATTTTATT | TAAAACTTTT | TTAATTCAT | TTTCCTTTTT | GATTTATTAT | 540 |
| TTAAAAAACA | ATTAATATC | AAAAGTTAA | AGTTTATGAA | TGTATTTGT | ATCTTCAATT | 600 |
| TGAAACATAT | TGTTGATAAC | ATAGATGGTT | GTTAATTATT | TGAAGTTGAA | TATATTGAAT | 660 |
| TTATGAATGT | GATATTCAAA | TTAAAGAGAC | GCCCGAAATT | TTATGGAAAT | CGATAAGCTT | 720 |
| GAAATAACAA | TTTGACTTGC | CACAAATGAC | CACCATTTTG | AGTGGGTAAT | ATATCAAAAA | 780 |
| GTTGGAAACA | CTGAGAGAAG | CTTATATCTA | AAATTTAAGG | AAATCTGGAG | ATGATTTAGG | 840 |
| GTGGTTTTGC | ATCAAATTTC | AAAGCAATGG | AATGAAGAAG | ATGAAGAACA | TAAACTAACT | 900 |
| TTTCAGATGC | GTAGGAAAAG | GAAAAGTTAT | TAAAATTAGT | CATGGATTTG | TTGGGTATTA | 960 |
| AATATAAGAT | AAAAATTTAT | CTTAATATTC | AAAGTTTATT | GAAGAAAATC | ATTTGGGTGT | 1020 |
| TCATATATTT | TTTTAAAAAA | AAATTGGTGC | ATATATCAAA | GATTTTTAT | ATACAGTTCT | 1080 |
| TGATTTTGGA | GAGTAATGGA | TGAAATTGCT | ATAAATAATT | TGGTGTATC | AATTAAAGTA | 1140 |
| GTGATAGGAA | TGATTTCAAG | ATGGTGAAGA | ACTTTGGTGG | TGCCATATTT | ATGTTGTGAA | 1200 |
| GTTGAAAGAA | AATTAATAAC | TAAAAATACA | CATTTATTAT | TTGTGTTGGT | TCAAACTCTA | 1260 |
| TTACCGAGAG | TGAGATACAC | TCACTATACC | ACAATGTGCC | ACGTAAGCGT | CTAGGGAGTA | 1320 |
| AATTATTTTT | AGTTTAAAT | AATTCAGGGA | GTGATAGGAC | ATCCGTGAAG | TTGAAGTATG | 1380 |
| TAGTTGAGAT | TTCGGGTATA | GATTGGGGGG | CTTTAGACCA | TTGGATTTGA | TCTAAGTATC | 1440 |
| TATTTCAATT | TATATGATGT | AATTTGACTT | GACACGAAAT | TTAAGACGAA | GAAAAAAGA | 1500 |
| CTAAGTACTT | CCACTGTCAA | ACAATATTTG | TCCACTACTA | TTTTACACAA | TTAGTAAGAA | 1560 |
| ACTATACCCT | TTGAATTTAA | TAAATACAAT | CTCTTGAAAA | ATGTAATAGT | GAAATGACTA | 1620 |
| TAATTAATGA | TAAAAGTACA | TCAGGAACTA | AGTGTAAAAT | TATCAATTCA | TTTTATAAAG | 1680 |
| TAGACAAGTA | TTGTTGGACA | TCCTAAAATA | GTATAGTTGA | CAACTATTAT | TGAATAGAGG | 1740 |
| GAGTATCTCT | GTGTGACTAT | ACATTTTTT | AAAATTAAAA | TTACTAAATA | TAGAGAATTA | 1800 |
| AAAATGTGTT | ATTTCCCCCT | TTTTAGAATG | ATTAAAAAGA | AATCCGAGTC | TTATTTTAGA | 1860 |

```
GAGATTTAAA  TTGTTTCACT  AAATTTTTAT  CAAGTTAAAA  ATGCTTATTT  TAGAGAGTTG   1920
AGTTATTTGG  CCATGTTTTT  AGAAAAAAAA  AGTGATTGTG  AGTATTGAGA  GAAACTATTT   1980
TTCAATAGTT  ACAAAAAAAT  TTGGTTTAGT  TTTTACTGTG  TTTTTCCTCC  ATGGTTTCCA   2040
ACACTTGACT  CTAGGCTTCT  GTGCTATTTC  GAAGCACTCT  ATAGTCTGTA  TCAGGGGCGG   2100
AGCCAGCTTG  AATCCCTTCG  GCGAAAAATA  TAACTATTTC  TATATCGTAA  AAATTATTCT   2160
TTATGTATTT  ATAGTAGATA  TTTAACCCCC  CTCGGTTAGT  CCGTGTGTTT  AGTTCTTCAG   2220
ATTTTGAACC  CCCCTAAATC  CGCCACTGGT  CTATACGCTT  GATGTCAACT  TGGTAACCTC   2280
CATTATCAAA  GGTGTCTTCT  TGAACTAAGA  TAACCAATGC  TTCAAAGTGA  AGATCACATA   2340
TTACACCATT  GATTATATGA  TCATTAGGTG  AAACTAAGCC  ACCCCCGATT  TCTAGATTTT   2400
GATACATTCC  CTCAAGCACA  AAGACACACA  CAATCATGCA  TAAGAAGAAA  ATAGTAGTGA   2460
AAAGTTCATG  ATTACATTTA  TGCCCGATAC  TTCTATAACC  TACTGCAAAT  TATACACTTT   2520
TATGGTATAG  CTATAGCCA   AGTATCATGA  TAAACAACAA  ATACTGAAGT  TCGCAACAAC   2580
CACAATAAGT  TGGTTAGGAG  GAAGATAATA  ATCACTAAGA  CTATAACTGT  CGTCGAACTT   2640
CCAAATGTAA  GCAACTTTAT  GATAAGCTAG  TCATCACAAC  ATTCAATAAA  GATCAATATC   2700
CCAAGAGAGT  TAGTATGCAA  TTGGATTAGA  AGACGAACAG  TATCTGATAA  AATAAAGGAG   2760
CCTATAAATT  CAAAAGACAA  TGCTTGTATG  CTCATATTAT  CCCTATTACC  TTTTTGCGCT   2820
AAAACACACT  TCCAACTCAA  GTTGTTGGAT  ATAATTCATT  TTGCAAGATT  CACAAGAAAT   2880
GTCAATTTTG  AGCTACCAAA  CTAGTCCATC  ATCTCGTTGG  TTATCTTCCA  TTTATCAAAC   2940
AAAGAATCAC  ATCCCCGGA   TCAAATACAA  ATCAAACCCC  AAACATCTCT  AAGAGCTCCA   3000
ACAATCACTT  CACATAGCAT  CTCAAATGGC  AAGTTTTAAG  AATAAACACA  AGTCATCACA   3060
TAGTTGCTGC  AACAAGTCTT  AAGATCGAGG  GACTTAACCT  TCATAGCTTT  AGAAAGCTCA   3120
AGCATAAGTG  TCAACCATTC  ATACAATACA  ATCTTGAACG  TAGAATATAT  TAAATAGTAA   3180
ATCCTAATGT  ATCCCAAGAT  AGTGCCTCCA  AACTTCTTAC  TTCCTTGTAG  TCTTTCCTGT   3240
GATGAACCTT  GATAATGAGT  CTGTAAGTTT  TGGTTCCAAA  ACTGTACGTT  CTTATTCATC   3300
TGTAGTGGTA  CAAATTTATA  GTAGAGAGAT  ATAAACTAGC  AATCAGATTT  CCTTAATTCA   3360
AGGAGATTTG  AGCATCAAGG  GAAGCTCTAA  TTTCCTAAAC  TATTTGATAG  CATATTAAAG   3420
CTAATTTTGT  CAGATCTATT  TATATCCTAT  AAAATCAGAT  CTGATCCTAG  CCAGATATTT   3480
ACAAATCAAC  ACTCCCCTTC  AAGTTGACAT  GTAAGTATTT  ATCATGCCTA  ACTTGCTTAC   3540
AAGAATTTCA  CATTTTGGTT  CAAACAAGCC  TTTTATGAAA  ATATCCACAA  TTTGCTGGTC   3600
TGTTGGGACG  AAAGACATAC  ACACACTTCA  TTTTTCAATC  TTCGTTTTTA  TGAAGTTTCT   3660
ATCATGTTGA  ACTGGATTGG  GAACAATACT  TATGGCGGCT  TTGTTGTCAC  ATTACAACTT   3720
TATTGGTAGA  GAAAATTTTC  AGTCCATCTT  CTTGAGCCAG  TTCATTTCGT  AGATCTGTAT   3780
TCAACTTTAG  CAATGCTACA  AGCGACATTC  GGACGATACT  GATTCATTAC  TTGCAGGATT   3840
TATTAACAAT  CACAGGAAAC  TTAAAGGTG   GAAGGGAGAT  GGCCAAGGAG  TGTCGCGATG   3900
CAATAGGTAC  TATAAACCTT  GTGAAGGGCC  AGCATTTAGA  CAGAAGGACC  ACTAATCAAT   3960
TGGAGGATGC  TATAAAGCAC  CTAACACATG  TTGCTGTATT  TCTCACAAAT  CTGGAGAAGC   4020
GTCACCCTGC  TAATGGAATA  TCTATACATC  TTAGGCCTCT  ATTTTAGAA   GCTCATGATG   4080
GCTTTTCTCT  GATGTGTTCT  CATCCTCCTC  GTTCTCAGTT  TACCGTTAAA  CTGGATAACA   4140
TTGCTGAGAA  ATTCAAATCT  TCAAAGGCGT  CAAGATCAAC  AAGGCAAGTG  ATCCCAGAGC   4200
TGCTGCAAAT  AATTGAACCC  GAGAATATTG  CTAAGCGAAT  CAAAGCTTCA  AAGCCATCAA   4260
```

```
GATCATCTAG CCCAATCACT GTGGATATGG TGGGGTTTAT CGAATCCTTG CTTGGTTCTG    4320
TTCATCGTGC ATTGTTCTTT ATCAGTGCAG GGCCTCCTGT GTCTATGCTT GACAAGAAGC    4380
TTCGACATCT ACAAGTCTTC TTTAGACTAA TTTCAAAGCG GGGCATTGAG CATGAGAGTA    4440
TGAAGGATCT CTTCTACCAT GTTGAGGATG TAGCTTACAC TGCAGCACAA CTATGTGTCT    4500
TGGGGTCGAG CTGCCATATG GATGACGAGT TCTCTAAATT TCTGGAAAGG ATAAGTCGTC    4560
CTTTTAGCCC AGGATTGAGG CAGGTTTATC TCAATGCCTT GATAGGGTTA AATTCATCAA    4620
GATCAAAGAC TACAATGAAT GCCAAATATA TGCTTGATTT TGTTAGTGCT CTCCAAGATG    4680
ATCTGAGACT AAGATGTGAT AATCGAATTC GATGGCTCCA ACGAGGACTT TCTTACCTTT    4740
GTCGATTCCT CAGGGACATA GAATCTTATC CTGTTTCACA TCGACAACTG ATTTCTCTTC    4800
AATTGAATAT GGAAGATCTG GCTATTGGGT CTGCAAATGC CATCTACTCC TATGATGAGG    4860
ATATGGATAA GACTAGTGAA ATAGACCATG AGCTTTTTCA TTTGCAAATG AAGTTTAATT    4920
ATGTTAAAGT AGAGGTTGAT CTGATTCGTC TACAAAACAT TCAAGGCACC ATAATAGTTC    4980
CTATGAAAGA TCTGATTGAC TATGTTTGGG AAGAGCTGAT GTTCTTAGA AGTTATTTCA    5040
TGGATGCATT CGACCAGTTT AAAGAGCAGA CCAGGATAAC TGTTATTTTG AACTATATTC    5100
AGTCTGCAGT TAGTCAAGCA TGGTCAGTCT GTGATTCTCT TTGTCATGAC TTGAATCAAA    5160
ATGACTTGGC CAGGGAAATT AATTGCTTGC ATTTTCAATT GCTTCTTAAG TTCAAGTTTA    5220
TCAAGGTCGC TATTAGACAG ATGTGTCCCA GCATTCTGC ATCATCAACA CCAGACCATC    5280
CAATGATAGA TCTGCTGAAC TTTCTTCCCA TGAACTTTGA GGCCATTGAT TCCTATTCCA    5340
GCATGCTAAA AGCCTCCTGT CCATCTTCCT CACATCGTCC TAATAGGGAT GCGGAATCCC    5400
CCAATACATC ATTCTTATGT GGTCCCAATA CAGATGTGTA CTCCTTCTAT TCATCATCCT    5460
CACGTATTCC CAAGATGGAT GAGATATTGA AGAGGTTTCA TGAATATATT CTTGTCAATC    5520
GTCTACGGAA GGATGAAACC AATTTGACAT TTACTATTGC AGATGAGGTC AAAAAGTTTT    5580
ATGATGGGTT GTTGCTCATG GTTACATATC TTATTGAACC TCCAGTTCCT CACACTGAAT    5640
GCAGGAAGCA AAATGATCTC TCAATGCGAC ATGAAGCTGT TGCAATTGAG GCGGAATCTG    5700
CTGTGTGTTT ACATTATGAG GATAATATGA ATAACAACAG TAGGGAGATC AATCAGGTAC    5760
TTCAGTTTTT GACTGTGACT TTCTGGCTTA TCAAGTCTGA GGGTAACTTG ATGGATCTAC    5820
TGAAGCACAA ATCCACTTTG GGAAATCAAG TTCTAGATCT GATTGAGAGT GCTCATGAAG    5880
AGCTTATTCT CCTTAGATCT ATTCTCATGG ATCTTCTTAG GAAAAGCTT TACAGATTGG    5940
ATGATCTCTT AATGCATGCT GAGGTGACTG CAAAAAGGTT AGCAATATTC AGTGGTTCTT    6000
GTTATGAATA TTTCATGAAC GGAAGCAGCA CTGAGAAAAT GAGGCCCTTG TTATCTGATT    6060
TTCTGCAAGA GATTGAGTCT GTCAAGGTAG AGTTCAGAAA TGTTTGCTTG CAAGTTCTGG    6120
ATATATCACC TTTTTCCCTG ACAGATGGAG AAGGCCTTGT TAATTTCTTA TTAAAAAACC    6180
AGGCCAAGGT GCCGAATGAT GATGCTGTTT CTTCTGATGG AAGTTTAGAG GATGCAAGCA    6240
GCACTGAGAA AATGGGACTT CCATCTGATT TTCTCCGAGA GATTGAGTCT GTTGAGATAA    6300
AGGAGGCCAG AAAATTATAT GATCAAGTTT TGGATGCAAC ACATTGTGAG ACGAGTAAGA    6360
CAGATGGAAA AAGCTTTATC AACATTATGT TAACCCAACA GGACAAGTTG CCGGACTATG    6420
ATGCTGGTTC AGTCTCTTAT CTTCTTAACC AAATATCAGT AGTTAAAGAC AAACTATTGC    6480
ACATTGGCTC TTTACTTGTA GATATTGTAC AGTACCGGAA TATGCATATA GAACTTACAG    6540
ATCTCGCTGA ACGTGTTCAA GATAAAAACT ACATTTGTTT CTTCTCTGTC AAGGGTTATA    6600
TTCCTGCTTG GTATTACACA CTATATCTCT CTGATGTCAA GCAATTGCTT AAGTTTGTTG    6660
```

```
AGGCAGAGGT AAAGATTATT TGTCTGAAAG TACCAGATTC TTCAAGTTAT AGCTTCCCTA    6720
AGACAAATGG ATTAGGATAT CTCAATTGCT TTTTAGGCAA ATTGGAGGAG CTTTTACGTT    6780
CTAAGCTCGA TTTGATAATC GACTTAAAAC ATCAGATTGA ATCAGTCAAG GAGGGCTTAT    6840
TGTGCCTAAG ATCATTCATT GATCATTTTT CAGAAAGCTA TGATGAGCAT GATGAAGCTT    6900
GTGGTCTTAT AGCAAGAGTT TCTGTAATGG CATACAAGGC TGAGTATGTC ATTGACTCAT    6960
GCTTGGCCTA TTCTCATCCA CTCTGGTACA AAGTTCTTTG GATTTCTGAA GTTCTTGAGA    7020
ATATTAAGCT TGTAAATAAA GTTGTTGGTG AGACATGTGA AAGAAGGAAC ATTGAAGTTA    7080
CTGTGCATGA AGTTGCAAAG ACTACCACTT ATGTAGCACC ATCTTTTTCA GCTTATACTC    7140
AAAGAGCAAA CGAAGAAATG GAGGGTTTTC AGGATACAAT AGATGAATTA AAGGATAAAC    7200
TACTTGGAGG ATCACCTGAG CTTGATGTCA TCTCAATCGT TGGCATGCCA GGATTGGGCA    7260
AGACTACACT AGCAAGAAG ATTACAATG ATCCAGAAGT CACCTCTCGC TTCGATGTCC    7320
ATGCTCAATG TGTTGTGACT CAATTATATT CATGGAGAGA GTTGTTGCTC ACCATTTGA    7380
ATGATGTCCT TGAGCCTTCT GATCGCAATG AAAAAGAAGA TGGTGAAATA GCTGATGAGT    7440
TACGCCGATT TTTGTTGACC AAGAGATTCT TGATTCTCAT TGATGATGTG TGGGACTATA    7500
AAGTGTGGGA CAATCTATGT ATGTGCTTCA GTGATGTTTC AAATAGGAGT AGAATTATCC    7560
TAACAACCCG CTTGAATGAT GTCGCCGAAT ATGTCAAATG TGAAAGTGAT CCCCATCATC    7620
TTCGTTTATT CAGAGATGAC GAGAGTTGGA CATTATTACA GAAAGAAGTC TTTCAAGGAG    7680
AGAGCTGTCC ACCTGAACTT GAAGATGTGG GATTTGAAAT ATCAAAAAGT TGTAGAGGGT    7740
TGCCTCTCTC AGTTGTGTTA GTAGCTGGTG TTCTGAAACA GAAAAGAAG ACACTAGATT    7800
CATGGAAAGT AGTAGAACAA AGTCTAAGTT CCCAGAGGAT TGGCAGCTTG GAAGAGAGCA    7860
TATCTATAAT TGGATTCAGT TACAAGAATT TACCACACTA TCTTAAGCCT TGTTTTCTCT    7920
ATTTTGGAGG ATTTTTGCAG GGAAAGGATA TTCATGTCTC AAAAATGACC AAGTTGTGGG    7980
TAGCTGAAGG GTTTGTACAA GCAAACAACG AAAAAGGACA AGAAGATACC GCACAAGGTT    8040
TCTTGGACGA TCTTATTGGT AGGAATGTAG TGATGGCCAT GGAGAAGAGA CCTAATACCA    8100
AGGTGAAAAC GTGCCGCATT CATGATTTGT TGCATAAATT CTGCATGGAA AAGGCCAAAC    8160
AAGAGGATTT TCTTCTCCAA ATCAATAGGT AAAAAAAACT GTATTAATTT TACATTACCA    8220
AAAAAAAAGA ACTGTATTAA TTTTACTGTA TTATGTTTAT GCCAACTCTC ATTTCCATGT    8280
GTTCTCTTTT ATCCAATTCA GTGGAGAAGG TGTATTTCCT GAACGATTGG AGGAATACCG    8340
ATTGTTCGTT CATTCTTACC AAGATGAAAT TGATCTGTGG CGCCCATCTC GCTCTAATGT    8400
CCGATCTTTA CTATTCAATG CAATTGATCC AGATAACTTG TTATGGCCGC GTGATATCTC    8460
CTTCATTTTT GAGAGCTTCA AGCTTGTTAA AGTGTTGGAT TTGGAATCAT TCAACATTGG    8520
TGGTACTTTT CCCACTGAAA TACAATATCT AATTCAGATG AAGTACTTTG CGGCCCAAAC    8580
TGATGCAAAT TCAATTCCTT CATCTATAGC TAAGCTTGAA AATCTTGAGA CTTTTGTCGT    8640
AAGAGGATTG GGAGGAGAGA TGATATTACC TTGTTCACTT CTGAAGATGG TGAAATTGAG    8700
GCATATACAT GTAAATGATC GGGTTTCTTT TGGTTTGCAT GAGAACATGG ATGTTTTAAC    8760
TGGTAACTCA CAATTACCTA ATTTGGAAAC CTTTTCTACT CCACGTCTCT TTTATGGTAA    8820
AGACGCAGAG AAGGTTTTGA GGAAGATGCC AAAATTGAGA AAATTGAGTT GCATATTTTC    8880
AGGGACATTT GGTTATTCAA GGAAATTGAA GGGTAGGTGT GTTCGTTTTC CCAGATTAGA    8940
TTTTCTAAGT CACCTTGAGT CCCTCAAGCT GGTTTCGAAC AGCTATCCAG CCAAACTTCC    9000
TCACAAGTTC AATTTCCCCT CGCAACTAAG GGAACTGACT TTATCAAAGT TCCGTCTACC    9060
```

|  |  |  |  |  |  |
|---|---|---|---|---|---|
| TTGGACCCAA | ATTTCGATCA | TTGCAGAACT | GCCCAACTTG | GTAATTCTTA | AGTTATTGCT | 9120 |
| CAGAGCCTTT | GAAGGGGATC | ACTGGGAAGT | GAAAGATTCA | GAGTTCCTAG | AACTCAAATA | 9180 |
| CTTAAAACTG | GACAACCTCA | AAGTTGTACA | ATGGTCCATC | TCTGATGATG | CTTTTCCTAA | 9240 |
| GCTTGAACAT | TTGGTTTTAA | CGAAATGTAA | GCATCTTGAG | AAAATCCCTT | CTCGTTTTGA | 9300 |
| AGATGCTGTT | TGCCTAAATA | GAGTTGAGGT | GAACTGGTGC | AACTGGAATG | TTGCCAATTC | 9360 |
| AGCCCAAGAT | ATTCAAACTA | TGCAACATGA | AGTTATAGCA | AATGATTCAT | TCACAGTTAC | 9420 |
| TATACAGCCT | CCAGATTGGT | CTAAAGAACA | GCCCCTTGAC | TCTTAGCAAA | GGTTGTTCT | 9480 |
| TGCTGTGTTC | ATCCAAGTAC | ATTTAACATT | TATTCATTTT | GTTTGCACC | AGAACATGTT | 9540 |
| TGTTTTGCTA | GTATTACTTG | ATACATTAAA | AGAAATCGAA | CTCATATTTC | TGCTACAGTC | 9600 |
| TTAACTTTTC | TTGGGCTTAC | TCGAGGTCTA | GATTAGATCA | ATGGTTCATG | TAATTCTTAA | 9660 |
| TTCACTGTTT | CATTCAACTG | TCTTATCATA | GTTGTGAAAT | GACAATATTG | TTATCCCTAG | 9720 |
| CCAAATTTAT | TATGTTCAAA | TGAAAACTGA | TGTCACAACT | ACTTTTTGT | GAAATGTTTT | 9780 |
| TGAATTTTTT | GCTATAAAAT | TGACGAATTG | ACAGGCTTCT | ATTTTGTCA | GCTAAACTCT | 9840 |
| TTGTCACCAG | AGGTGTATTT | AGAATTACTG | TGGTTTTATG | AAAGATTTTT | ATAGAATTTT | 9900 |
| ATGCTTTTGC | AGAATCTTAA | GTTTCTAGTT | TAAAACAACA | GCACTTTTCT | GTTTCAGAGG | 9960 |
| TAGCAGCAGC | TAAAGTTCAA | GGCATTTTGT | TTATTTCTAG | AACAAGGGGA | GTTCTTACGT | 10020 |
| TGAATTCTTG | AAAAGAAGAA | GAATCAGGAG | CAGGTAAAGA | TTATCTCTTT | TTCTGTTTTT | 10080 |
| CTTCTTTTAG | ATGTTATTTC | TTCATCTTGA | ACGTGAACAC | CGCTGAAAGC | ATTTTAATAA | 10140 |
| AACCGGAGAA | ATAAATAAGA | TCTTTTTATA | TAAAGCATTA | TCATGTAAAT | ATGCCTAAAT | 10200 |
| CCATATGGTA | CAACTGTTTG | ACAAATGATA | GAGAGGGGAG | ACTGATGCAA | GTTTATAGT | 10260 |
| ATAAGTAAAA | CAGGATTGAG | AAAAAAATCC | TTGCACGATT | TCAATTTCT | GGCCACATCA | 10320 |
| CAATGTGTGT | CAAAGTTCCC | CTCTTTAAGT | GGAACAAGCA | ATCAGAAAAG | CACATTCTTA | 10380 |
| TCGGTGACTT | ACCAATACCA | GCTGACTGTC | TCATCTTGGT | TAACTTAGCC | TTGCTTACTT | 10440 |
| AGACTATTAG | ATTAGTTACT | AATGAGCTGG | TAAATTGGAA | CCAAATGTAG | TTAGCTTGAT | 10500 |
| GAGCTGGTAG | ATATGTATGT | ATGAAGATAC | ACGCGTAACT | TTAGTCAATG | GTTAATTTTT | 10560 |
| CATTTGTAT | TTTTTCTTC | ACAGAGTATA | TATGACGCGA | GAATACTTGG | CCTAAAAGTT | 10620 |
| TTTGCTTCAC | TAATTTAACT | ATTGCCGTGG | ATGAAACAAG | CATGGCAACA | TTTTCAACAA | 10680 |
| CTATCACTCA | AGCAATGTAA | AAAAAGGAGG | TTCTACGAGT | GGTACATGTA | AGAGTTTTGT | 10740 |
| GCACACAAGA | GGTTCTGAGA | CTTGAACCAT | CCATGTCCAA | GGCAGTTCAG | ATGCTAGTAA | 10800 |
| AGAAAGAAGA | AGATGAACCT | GCACTAATTA | ATCCTCCCTT | TATGAATAAG | AGAATGAGAA | 10860 |
| AAAGATGGAG | CTTCATGAAC | CAAAAGTTAC | CTTTTTTTTT | TTTAATGGCA | TTACTTTGAA | 10920 |
| GCACATGTTT | GTTAGTTGTA | AATTGTAATG | GTGAAGTGTT | TGTAAATA |  | 10968 |

( 2 ) INFORMATION FOR SEQ ID NO: 3:

( i ) SEQUENCE CHARACTERISTICS:
            ( A ) LENGTH: 1824 amino acids
            ( B ) TYPE: amino acid
            ( D ) TOPOLOGY: linear ( x i ) SEQUENCE DESCRIPTION: SEQ ID NO:3:

Met Ala Lys Glu Cys Arg Asp Ala Ile Gly Thr Ile Asn Leu Val Lys
              5                   10               15

Gly Gln His Leu Asp Arg Arg Thr Thr Asn Gln Leu Glu Asp Ala Ile
         20                   25               30

-continued

```
Lys His Leu Thr His Val Ala Val Phe Leu Thr Asn Leu Glu Lys Arg
         35              40                  45

His Pro Ala Asn Gly Ile Ser Ile His Leu Arg Pro Leu Phe Leu Glu
         50              55              60

Ala His Asp Gly Phe Ser Leu Met Cys Ser His Pro Pro Arg Ser Gln
 65              70              75              80

Phe Thr Val Lys Leu Asp Asn Ile Ala Glu Lys Phe Lys Ser Ser Lys
                 85              90                  95

Ala Ser Arg Ser Thr Arg Gln Val Ile Pro Glu Leu Leu Gln Ile Ile
             100             105             110

Glu Pro Glu Asn Ile Ala Lys Arg Ile Lys Ala Ser Lys Pro Ser Arg
             115             120             125

Ser Ser Pro Ile Thr Val Asp Met Val Gly Phe Ile Glu Ser Leu
    130             135             140

Leu Gly Ser Val His Arg Ala Leu Phe Phe Ile Ser Ala Gly Pro Pro
145             150             155             160

Val Ser Met Leu Asp Lys Lys Leu Arg His Leu Gln Val Phe Phe Arg
             165             170             175

Leu Ile Ser Lys Arg Gly Ile Glu His Glu Ser Met Lys Asp Leu Phe
             180             185             190

Tyr His Val Glu Asp Val Ala Tyr Thr Ala Ala Gln Leu Cys Val Leu
         195             200             205

Gly Ser Ser Cys His Met Asp Asp Glu Phe Ser Lys Phe Leu Glu Arg
    210             215             220

Ile Ser Arg Pro Phe Ser Pro Gly Leu Arg Gln Val Tyr Leu Asn Ala
225             230             235             240

Leu Ile Gly Leu Asn Ser Ser Arg Ser Lys Thr Thr Met Asn Ala Lys
             245             250             255

Tyr Met Leu Asp Phe Val Ser Ala Leu Gln Asp Asp Leu Arg Leu Arg
             260             265             270

Cys Asp Asn Arg Ile Arg Trp Leu Gln Arg Gly Leu Ser Tyr Leu Cys
         275             280             285

Arg Phe Leu Arg Asp Ile Glu Ser Tyr Pro Val Ser His Arg Gln Leu
    290             295             300

Ile Ser Leu Gln Leu Asn Met Glu Asp Leu Ala Ile Gly Ser Ala Asn
305             310             315             320

Ala Ile Tyr Ser Tyr Asp Glu Asp Met Asp Lys Thr Ser Glu Ile Asp
             325             330             335

His Glu Leu Phe His Leu Gln Met Lys Phe Asn Tyr Val Lys Val Glu
             340             345             350

Val Asp Leu Ile Arg Leu Gln Asn Ile Gln Gly Thr Ile Ile Val Pro
         355             360             365

Met Lys Asp Leu Ile Asp Tyr Val Trp Glu Glu Leu Met Phe Phe Arg
    370             375             380

Ser Tyr Phe Met Asp Ala Phe Asp Gln Phe Lys Glu Gln Thr Arg Ile
385             390             395             400

Thr Val Ile Leu Asn Tyr Ile Gln Ser Ala Val Ser Gln Ala Trp Ser
             405             410             415

Val Cys Asp Ser Leu Cys His Asp Leu Asn Gln Asn Asp Leu Ala Arg
             420             425             430

Glu Ile Asn Cys Leu His Phe Gln Leu Leu Leu Lys Phe Lys Phe Ile
         435             440             445

Lys Val Ala Ile Arg Gln Met Cys Pro Ser Ile Ser Ala Ser Ser Thr
```

|  |  |  |  |  | 450 |  |  |  |  | 455 |  |  |  |  | 460 |  |  |  |  |
|---|---|---|---|---|---|---|---|---|---|---|---|---|---|---|---|---|---|---|---|---|

Pro Asp His Pro Met Ile Asp Leu Leu Asn Phe Leu Pro Met Asn Phe
465 470 475 480

Glu Ala Ile Asp Ser Tyr Ser Ser Met Leu Lys Ala Ser Cys Pro Ser
485 490 495

Ser Ser His Arg Pro Asn Arg Asp Ala Glu Ser Pro Asn Thr Ser Phe
500 505 510

Leu Cys Gly Pro Asn Thr Asp Val Tyr Ser Phe Tyr Ser Ser Ser Ser
515 520 525

Arg Ile Pro Lys Met Asp Glu Ile Leu Lys Arg Phe His Glu Tyr Ile
530 535 540

Leu Val Asn Leu Leu Arg Lys Asp Glu Thr Asn Leu Thr Phe Thr Ile
545 550 555 560

Ala Asp Glu Val Lys Lys Phe Tyr Glu Gly Leu Leu Leu Met Val Thr
565 570 575

Tyr Leu Ile Glu Pro Pro Val Pro His Thr Glu Cys Arg Lys Gln Asn
580 585 590

Asp Leu Ser Met Arg His Glu Ala Val Ala Ile Glu Ala Glu Ser Ala
595 600 605

Val Cys Leu His Tyr Glu Asp Asn Met Asn Asn Ser Arg Glu Ile
610 615 620

Asn Gln Val Leu Gln Phe Leu Thr Val Thr Phe Trp Leu Ile Lys Ser
625 630 635 640

Glu Gly Asn Leu Met Asp Leu Leu Lys His Lys Ser Thr Leu Gly Asn
645 650 655

Gln Val Leu Asp Leu Ile Glu Ser Ala His Glu Glu Leu Ile Leu Leu
660 665 670

Arg Ser Ile Leu Met Asp Leu Leu Arg Lys Lys Leu Tyr Arg Leu Asp
675 680 685

Asp Leu Leu Met His Ala Glu Val Thr Ala Lys Arg Leu Ala Ile Phe
690 695 700

Ser Gly Ser Cys Tyr Glu Tyr Phe Met Asn Gly Ser Ser Thr Glu Lys
705 710 715 720

Met Arg Pro Leu Leu Ser Asp Phe Leu Gln Glu Ile Glu Ser Val Lys
725 730 735

Val Glu Phe Arg Asn Val Cys Leu Gln Val Leu Asp Ile Ser Pro Phe
740 745 750

Ser Leu Thr Asp Gly Glu Gly Leu Asn Phe Leu Leu Lys Asn Gln
755 760 765

Ala Lys Val Pro Asn Asp Asp Ala Val Ser Ser Asp Gly Ser Leu Glu
770 775 780

Asp Ala Ser Ser Thr Glu Lys Met Gly Leu Pro Ser Asp Phe Leu Arg
785 790 795 800

Glu Ile Glu Ser Val Glu Ile Lys Glu Ala Arg Lys Leu Tyr Asp Gln
805 810 815

Val Leu Asp Ala Thr His Cys Glu Thr Ser Lys Thr Asp Gly Lys Ser
820 825 830

Phe Ile Asn Ile Met Leu Thr Gln Gln Asp Lys Leu Pro Asp Tyr Asp
835 840 845

Ala Gly Ser Val Ser Tyr Leu Leu Asn Gln Ile Ser Val Val Lys Asp
850 855 860

Lys Leu Leu His Ile Gly Ser Leu Leu Val Asp Ile Val Gln Tyr Arg
865 870 875 880

```
Asn Met His Ile Glu Leu Thr Asp Leu Ala Glu Arg Val Gln Asp Lys
            885                 890                 895
Asn Tyr Ile Cys Phe Phe Ser Val Lys Gly Tyr Ile Pro Ala Trp Tyr
            900                 905                 910
Tyr Thr Leu Tyr Leu Ser Asp Val Lys Gln Leu Leu Lys Phe Val Glu
            915                 920                 925
Ala Glu Val Lys Ile Ile Cys Leu Lys Val Pro Asp Ser Ser Ser Tyr
            930                 935                 940
Ser Phe Pro Lys Thr Asn Gly Leu Gly Tyr Leu Asn Cys Phe Leu Gly
945                 950                 955                 960
Lys Leu Glu Glu Leu Leu Arg Ser Lys Leu Asp Leu Ile Ile Asp Leu
                965                 970                 975
Lys His Gln Ile Glu Ser Val Lys Glu Gly Leu Leu Cys Leu Arg Ser
            980                 985                 990
Phe Ile Asp His Phe Ser Glu Ser Tyr Asp Glu His Asp Glu Ala Cys
            995                 1000                1005
Gly Leu Ile Ala Arg Val Ser Val Met Ala Tyr Lys Ala Glu Tyr Val
            1010                1015                1020
Ile Asp Ser Cys Leu Ala Tyr Ser His Pro Leu Trp Tyr Lys Val Leu
1025                1030                1035                1040
Trp Ile Ser Glu Val Leu Glu Asn Ile Lys Leu Val Asn Lys Val Val
                1045                1050                1055
Gly Glu Thr Cys Glu Arg Arg Asn Ile Glu Val Thr Val His Glu Val
            1060                1065                1070
Ala Lys Thr Thr Thr Tyr Val Ala Pro Ser Phe Ser Ala Tyr Thr Gln
            1075                1080                1085
Arg Ala Asn Glu Glu Met Glu Gly Phe Gln Asp Thr Ile Asp Glu Leu
            1090                1095                1100
Lys Asp Lys Leu Leu Gly Gly Ser Pro Glu Leu Asp Val Ile Ser Ile
1105                1110                1115                1120
Val Gly Met Pro Gly Leu Gly Lys Thr Thr Leu Ala Lys Lys Ile Tyr
                1125                1130                1135
Asn Asp Pro Glu Val Thr Ser Arg Phe Asp Val His Ala Gln Cys Val
            1140                1145                1150
Val Thr Gln Leu Tyr Ser Trp Arg Glu Leu Leu Leu Thr Ile Leu Asn
            1155                1160                1165
Asp Val Leu Glu Pro Ser Asp Arg Asn Glu Lys Glu Asp Gly Glu Ile
            1170                1175                1180
Ala Asp Glu Leu Arg Arg Phe Leu Leu Thr Lys Arg Phe Leu Ile Leu
1185                1190                1195                1200
Ile Asp Asp Val Trp Asp Tyr Lys Val Trp Asp Asn Leu Cys Met Cys
                1205                1210                1215
Phe Ser Asp Val Ser Asn Arg Ser Arg Ile Ile Leu Thr Thr Arg Leu
            1220                1225                1230
Asn Asp Val Ala Glu Tyr Val Lys Cys Glu Ser Asp Pro His His Leu
            1235                1240                1245
Arg Leu Phe Arg Asp Asp Glu Ser Trp Thr Leu Leu Gln Lys Glu Val
            1250                1255                1260
Phe Gln Gly Glu Ser Cys Pro Pro Glu Leu Glu Asp Val Gly Phe Glu
1265                1270                1275                1280
Ile Ser Lys Ser Cys Arg Gly Leu Pro Leu Ser Val Val Leu Val Ala
                1285                1290                1295
Gly Val Leu Lys Gln Lys Lys Lys Thr Leu Asp Ser Trp Lys Val Val
            1300                1305                1310
```

Glu Gln Ser Leu Ser Ser Gln Arg Ile Gly Ser Leu Glu Glu Ser Ile
                1315                1320                1325

Ser Ile Ile Gly Phe Ser Tyr Lys Asn Leu Pro His Tyr Leu Lys Pro
                1330                1335                1340

Cys Phe Leu Tyr Phe Gly Gly Phe Leu Gln Gly Lys Asp Ile His Val
1345                1350                1355                1360

Ser Lys Met Thr Lys Leu Trp Val Ala Glu Gly Phe Val Gln Ala Asn
                1365                1370                1375

Asn Glu Lys Gly Gln Glu Asp Thr Ala Gln Gly Phe Leu Asp Asp Leu
                1380                1385                1390

Ile Gly Arg Asn Val Val Met Ala Met Glu Lys Arg Pro Asn Thr Lys
                1395                1400                1405

Val Lys Thr Cys Arg Ile His Asp Leu Leu His Lys Phe Cys Met Glu
                1410                1415                1420

Lys Ala Lys Gln Glu Asp Phe Leu Leu Gln Ile Asn Ser Gly Glu Gly
1425                1430                1435                1440

Val Phe Pro Glu Arg Leu Glu Glu Tyr Arg Leu Phe Val His Ser Tyr
                1445                1450                1455

Gln Asp Glu Ile Asp Leu Trp Arg Pro Ser Arg Ser Asn Val Arg Ser
                1460                1465                1470

Leu Leu Phe Asn Ala Ile Asp Pro Asp Asn Leu Leu Trp Pro Arg Asp
                1475                1480                1485

Ile Ser Phe Ile Phe Glu Ser Phe Lys Leu Val Lys Val Leu Asp Leu
                1490                1495                1500

Glu Ser Phe Asn Ile Gly Gly Thr Phe Pro Thr Glu Ile Gln Tyr Leu
1505                1510                1515                1520

Ile Gln Met Lys Tyr Phe Ala Ala Gln Thr Asp Ala Asn Ser Ile Pro
                1525                1530                1535

Ser Ser Ile Ala Lys Leu Glu Asn Leu Glu Thr Phe Val Val Arg Gly
                1540                1545                1550

Leu Gly Gly Glu Met Ile Leu Pro Cys Ser Leu Leu Lys Met Val Lys
                1555                1560                1565

Leu Arg His Ile His Val Asn Asp Arg Val Ser Phe Gly Leu His Glu
                1570                1575                1580

Asn Met Asp Val Leu Thr Gly Asn Ser Gln Leu Pro Asn Leu Glu Thr
1585                1590                1595                1600

Phe Ser Thr Pro Arg Leu Phe Tyr Gly Lys Asp Ala Glu Lys Val Leu
                1605                1610                1615

Arg Lys Met Pro Lys Leu Arg Lys Leu Ser Cys Ile Phe Ser Gly Thr
                1620                1625                1630

Phe Gly Tyr Ser Arg Lys Leu Lys Gly Arg Cys Val Arg Phe Pro Arg
                1635                1640                1645

Leu Asp Phe Leu Ser His Leu Glu Ser Leu Lys Leu Val Ser Asn Ser
                1650                1655                1660

Tyr Pro Ala Lys Leu Pro His Lys Phe Asn Phe Pro Ser Gln Leu Arg
1665                1670                1675                1680

Glu Leu Thr Leu Ser Lys Phe Arg Leu Pro Trp Thr Gln Ile Ser Ile
                1685                1690                1695

Ile Ala Glu Leu Pro Asn Leu Val Ile Leu Lys Leu Leu Leu Arg Ala
                1700                1705                1710

Phe Glu Gly Asp His Trp Glu Val Lys Asp Ser Glu Phe Leu Glu Leu
                1715                1720                1725

Lys Tyr Leu Lys Leu Asp Asn Leu Lys Val Val Gln Trp Ser Ile Ser

-continued

```
                    1730                      1735                          1740

Asp  Asp  Ala  Phe  Pro  Lys  Leu  Glu  His  Leu  Val  Leu  Thr  Lys  Cys  Lys
1745                          1750                    1755                      1760

His  Leu  Glu  Lys  Ile  Pro  Ser  Arg  Phe  Glu  Asp  Ala  Val  Cys  Leu  Asn
                         1765                    1770                    1775

Arg  Val  Glu  Val  Asn  Trp  Cys  Asn  Trp  Asn  Val  Ala  Asn  Ser  Ala  Gln
                    1780                    1785                    1790

Asp  Ile  Gln  Thr  Met  Gln  His  Glu  Val  Ile  Ala  Asn  Asp  Ser  Phe  Thr
               1795                    1800                    1805

Val  Thr  Ile  Gln  Pro  Pro  Asp  Trp  Ser  Lys  Glu  Gln  Pro  Leu  Asp  Ser
1810                          1815                    1820
```

( 2 ) INFORMATION FOR SEQ ID NO: 4:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:4:

```
Leu  Xaa  Xaa  Leu  Xaa  Xaa  Leu  Xaa  Xaa  Leu  Xaa  Leu  Xaa  Xaa  Xaa  Xaa
                    5                         10                        15

Xaa  Leu  Xaa  Xaa  Ile  Pro  Ser  Xaa
               20
```

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

```
             CCAAGTGCAG  AGAGTACTGG  A                                        21
```

( 2 ) INFORMATION FOR SEQ ID NO: 6:

( i ) SEQUENCE CHARACTERISTICS:
        ( A ) LENGTH: 24 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:6:

```
             TGAATGAACA  TGATCAAAGT  ATGC                                     24
```

( 2 ) INFORMATION FOR SEQ ID NO: 7:

( i ) SEQUENCE CHARACTERISTICS:
        ( A ) LENGTH: 23 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

```
             ACTCCAGAAC  CAATGATTGC  ATA                                      23
```

( 2 ) INFORMATION FOR SEQ ID NO: 8:

( i ) SEQUENCE CHARACTERISTICS:
        ( A ) LENGTH: 23 base pairs
        ( B ) TYPE: nucleic acid
        ( C ) STRANDEDNESS: single stranded
        ( D ) TOPOLOGY: linear (xi) SEQUENCE DESCRIPTION: SEQ ID NO:8:

GGAATTTAAA TCTAGAATAT CTC    23

(2) INFORMATION FOR SEQ ID NO: 9:

(i) SEQUENCE CHARACTERISTICS:
      (A) LENGTH: 17 base pairs
      (B) TYPE: nucleic acid
      (C) STRANDEDNESS: single stranded
      (D) TOPOLOGY: linear (xi) SEQUENCE DESCRIPTION: SEQ ID NO:9:

CCTTCTATTC ATCATCC    17

(2) INFORMATION FOR SEQ ID NO: 10:

(i) SEQUENCE CHARACTERISTICS:
      (A) LENGTH: 17 base pairs
      (B) TYPE: nucleic acid
      (C) STRANDEDNESS: single stranded
      (D) TOPOLOGY: linear (xi) SEQUENCE DESCRIPTION: SEQ ID NO:10:

CTGCTCCTGA TTCTTCT    17

(2) INFORMATION FOR SEQ ID NO: 11:

(i) SEQUENCE CHARACTERISTICS:
      (A) LENGTH: 38 base pairs
      (B) TYPE: nucleic acid
      (C) STRANDEDNESS: single stranded
      (D) TOPOLOGY: linear (xi) SEQUENCE DESCRIPTION: SEQ ID NO:11:

TTGCATTGAC GTCGACTATC CAGGTTTTTT TTTTTTTT    38

(2) INFORMATION FOR SEQ ID NO: 12:

(i) SEQUENCE CHARACTERISTICS:
      (A) LENGTH: 31 base pairs
      (B) TYPE: nucleic acid
      (C) STRANDEDNESS: single stranded
      (D) TOPOLOGY: linear (xi) SEQUENCE DESCRIPTION: SEQ ID NO:12:

TAAGATATGT AACCATGAGC AACAACCCTT C    31

(2) INFORMATION FOR SEQ ID NO: 13:

(i) SEQUENCE CHARACTERISTICS:
      (A) LENGTH: 19 base pairs
      (B) TYPE: nucleic acid
      (C) STRANDEDNESS: single stranded
      (D) TOPOLOGY: linear (xi) SEQUENCE DESCRIPTION: SEQ ID NO:13:

GACCTCATCT GCAATAGTA    19

(2) INFORMATION FOR SEQ ID NO: 14:

(i) SEQUENCE CHARACTERISTICS:
      (A) LENGTH: 24 base pairs
      (B) TYPE: nucleic acid
      (C) STRANDEDNESS: single stranded
      (D) TOPOLOGY: linear (xi) SEQUENCE DESCRIPTION: SEQ ID NO:14:

```
                    AGGCCCTGCA CTGATAAAGA ACAA                                          24
```

( 2 ) INFORMATION FOR SEQ ID NO: 15:

( i ) SEQUENCE CHARACTERISTICS:
        ( A ) LENGTH: 24 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:15:

```
                    AGCAGCTCTG GGATCACTTG CCTT                                           24
```